(12) United States Patent
Vigh et al.

(10) Patent No.: US 9,689,841 B2
(45) Date of Patent: Jun. 27, 2017

(54) FLUORESCENT PI MARKERS FOR ISOELECTRIC FOCUSING SEPARATIONS AND FLUORESCENT LABELING

(75) Inventors: Gyula Vigh, Magnolia, TX (US); Ming-Chien Li, College Station, TX (US)

(73) Assignee: The Texas A&M University System, College Station, TX (US)

( * ) Notice: Subject to any disclaimer, the term of this patent is extended or adjusted under 35 U.S.C. 154(b) by 428 days.

(21) Appl. No.: 14/241,358

(22) PCT Filed: Aug. 27, 2012

(86) PCT No.: PCT/US2012/052579
§ 371 (c)(1),
(2), (4) Date: Aug. 15, 2014

(87) PCT Pub. No.: WO2013/033046
PCT Pub. Date: Mar. 7, 2013

(65) Prior Publication Data
US 2014/0377875 A1    Dec. 25, 2014

Related U.S. Application Data

(60) Provisional application No. 61/528,011, filed on Aug. 26, 2011.

(51) Int. Cl.
*C07C 311/32* (2006.01)
*G01N 27/447* (2006.01)
(Continued)

(52) U.S. Cl.
CPC ...... *G01N 27/44795* (2013.01); *C07C 311/32* (2013.01); *C07C 311/37* (2013.01); *C07C 311/42* (2013.01); *C07D 233/64* (2013.01);

*C07D 295/088* (2013.01); *C07D 295/13* (2013.01); *C07D 295/26* (2013.01); *C09K 11/06* (2013.01); *G01N 27/447* (2013.01); *G01N 33/582* (2013.01); *C07C 2103/50* (2013.01);
(Continued)

(58) Field of Classification Search
None
See application file for complete search history.

(56) References Cited

U.S. PATENT DOCUMENTS 5,066,676 A  * 11/1991 Caccia ................. C07D 311/86
                                                  514/562
6,923,896 B2    8/2005 Vigh
(Continued)

FOREIGN PATENT DOCUMENTS

WO    2010/116142 A2   10/2010
WO    2012/027717 A2    3/2012

OTHER PUBLICATIONS

Estrada, Roy Tonacao, "Fluorescent Labeling Reagents Optimized for Capillary Electrophoretic Separations", May 2010, pp. 1-290.*
(Continued)

*Primary Examiner* — Sudhakar Katakam
*Assistant Examiner* — Jennifer C Sawyer
(74) *Attorney, Agent, or Firm* — Christensen O'Connor Johnson Kindness PLLC

(57) ABSTRACT

UV-Absorbing and fluorescent pI markers for isoelectric focusing separations and fluorescent labeling, and methods for making and using the markers.

4 Claims, 40 Drawing Sheets

(51) Int. Cl.
*C09K 11/06* (2006.01)
*C07C 311/42* (2006.01)
*C07D 233/64* (2006.01)
*C07D 295/088* (2006.01)
*C07D 295/13* (2006.01)
*C07D 295/26* (2006.01)
*C07C 311/37* (2006.01)
*G01N 33/58* (2006.01)

(52) U.S. Cl.
CPC .......... *C09K 2211/1007* (2013.01); *C09K 2211/1011* (2013.01); *C09K 2211/1033* (2013.01); *C09K 2211/1044* (2013.01); *Y10T 436/143333* (2015.01)

(56) References Cited

U.S. PATENT DOCUMENTS

2003/0226752 A1 12/2003 Vigh
2006/0145091 A1 7/2006 Patel

OTHER PUBLICATIONS

International Preliminary Report on Patentability mailed Mar. 4, 2014, issued in corresponding International Application No. PCT/US2012/052579, filed Aug. 27, 2012, 8 pages.

International Search Report and Written Opinion mailed May 7, 2013, issued in corresponding International Application No. PCT/US2012/052579, filed Aug. 27, 2012, 11 pages.

Lalwani, S., and G. Vigh, "A Family of High-Buffering Capacity Diamino Sulfate Isoelectric Buffers fo pH-Biased Isoelectric Trapping Separations," Electrophoresis 26(1):3-9, Jan. 2005.

Lalwani, S., et al., "Synthesis and Characterization of Quaternary Ammonium Dicarboxylic Acid Isoelectric Buffers and Their Use in pH-Biased Isoelectric Trapping Separations," Electrophoresis 26(10):2047-2055, May 2005.

\* cited by examiner

Step 1

Step 2

Step 3

Step 1

Step 2

Step 3

Step 1

Step 2

Step 3

Step 1

Step 2

Step 3

HA: triprotic amino acid or aminosulfonic acid or aminophosphonic acid

US 9,689,841 B2

FLUORESCENT PI MARKERS FOR ISOELECTRIC FOCUSING SEPARATIONS AND FLUORESCENT LABELING

CROSS-REFERENCES TO RELATED APPLICATIONS

This application is the national stage of International Application No. PCT/US2012/052579, filed Aug. 27, 2012, which claims the benefit of U.S. Patent Application No. 61/528,011, filed Aug. 26, 2011. Each application is expressly incorporated herein by reference in its entirety.

BACKGROUND OF THE INVENTION

An ampholytic compound dissolved in an aqueous buffer can be present in the solution either as a cationic, isoelectric or anionic species, depending on the pH of the solution. In the presence of a nonalternating electric field, the cationic or anionic species migrate electrophoretically toward the cathode or the anode, respectively. At a certain solution pH where the ampholyte becomes isoelectric, the net electrophoretic migration of its band becomes zero. The numeric value of this solution pH is equal to the pI value (isoelectric point) of the ampholyte. The pI value of an ampholyte is a material characteristic that is determined by the structure of the ampholyte (the types and $pK_a$ values of its weak and strong electrolyte functional groups). When the ampholyte contains a single acidic group (characterized by $pK_a^{acid}$) and a single basic group (characterized by $pK_a^{conjugate\ acid}$ for this conjugate acid form), the pI value of the ampholyte can be calculated as $pI=(pK_a^{acid}+pK_a^{conjugate\ acid})/2$. When an ampholyte contains two acidic groups (characterized by $pK_a^{acid1}$ and $pK_a^{acid2}$) and one basic group (characterized by $pK_a^{conjugate\ acid}$ for its conjugate acid form) with $pK_a^{acid1}<pK_a^{acid2}<<pK_a^{conjugate\ acid}$, the pI of the ampholyte lies between $pK_a^{acid1}$ and $pK_a^{acid2}$ and is calculated as $pI=(pK_a^{acid1}\ pK_a^{acid2})/2$. In such cases, the acidic groups between which the pI lies are called the buffering groups, while the basic group is called the titrating group or charge balancing group. Similarly, when an ampholyte contains two basic groups (characterized by $pK_a^{conjugate\ acid1}$ and $pK_a^{conjugate\ acid2}$ for their conjugate acid forms) and one acidic group (characterized by $pK_a^{acid}$) with $pK_a^{acid}<<pK_a^{conjugate\ acid1}<pK_a^{conjugate\ acid2}$, the pI of the ampholyte lies between $pK_a^{conjugate\ acid1}$ and $pK_a^{conjugate\ acid2}$ and is calculated as $pI=(pK_a^{conjugate\ acid1},pK_a^{conjugate\ acid2})/2$. In such cases, the two basic groups between which the pI lies are called the buffering groups, while the acidic group is called the titrating group or charge balancing group. When the ampholyte contains multiple buffering groups and multiple titrating or charge balancing groups with relatively close $pK_a$ values, the charge contribution of each species needs to be evaluated in order to calculate the pI value. A general discussion of ampholytes, isoelectric points, pH gradients and isoelectric focusing can be found in the texts by Righetti, P. G., *Isoelectric Focusing: Theory, Methodology and Applications*; in Wood, T. S., Burdon, R. H., Eds.; *Laboratory Techniques in Biochemistry and Molecular Biology* 11; Elsevier Scientific: Amsterdam, 1983; Hjerten, S. in *Capillary Electrophoresis: Theory and Practice*; Grossman, P. D., Colburn, J. C., Eds.; Academic Press: San Diego, 1992; pp. 191-214; and Giddings, J. C., *Unified Separation Science*, Wiley-Interscience, New York, 1991, pp 180-182.

Ampholytes are often used in isoelectric focusing (IEF) or isoelectric trapping (IET) separations. Ampholytes whose presence can be detected due to their having a characteristic property—such as UV absorbance or fluorescence or radioactivity—that is different from the properties of the surrounding molecules can be used as pI markers in analytical and preparative-scale IEF separations. pI markers are used for the characterization of the pH gradient that effects the separation of ampholytic analytes. Once the shape of the pH gradient is known, one can determine the pI values of the separated analytes from their focusing position in the pH gradient. (For an excellent discussion of the characteristics and current availability of pI markers see M. Stastna, M. Travnicek and K. Slais, *Electrophoresis*, 2005, 26, 53-59.) Presently, among others, proteins, peptides, low-molecular weight aminophenols and azo dyes are used as pI markers. The main drawbacks of protein, oligopeptide and peptide pI markers include poor chemical (hydrolytic) stability and inadequate purity, often inadequate UV absorbance and, frequently, lack of fluorescence that can be excited by visible light. Certain peptide pI markers that lack visible light-excited fluorescence and are hydrolytically labile in low pH and high pH solutions are commercially available from Beckman-Coulter (250 South Kraemer Blvd, Brea, Calif. 92821-6232, USA). Fluorescently labeled oligopeptides have been used as pI markers (e.g., Shimura, K., Kasai, K., *Electrophoresis* 1995, 16, 1479-1484 and Shimura, K., Kamiya, K., Matsumoto, H., Kasai, K, *Anal. Chem.* 2002, 74, 1046-1053), but they still suffer of hydrolytic instability.

Therefore, synthetic, pure and stable low molecular weight, UV-absorbing and fluorescent pI markers are more desirable than pI markers that are proteins, oligopeptides or peptides. As an additional benefit, the structures of the low molecular weight synthetic pI markers are completely different from those of the separated proteins. Therefore, they are less likely to interfere with the post-IEF use or analysis of the separated protein fractions.

Certain low-molecular weight, UV absorbing pI markers are commercially available (e.g., from Bio-Rad Laboratories, 1000 Alfred Nobel Drive, Hercules, Calif. 94547, USA). The synthesis of other low-molecular weight, UV absorbing pI markers has been described (e.g., see the Stastna reference above). Certain low molecular weight fluorescent pI markers are commercially available (Fluka, Busch, Switzerland) and their use for capillary isoelectric focusing was described (Horka, M., Willimann, T., Blum, M., Nording, P., Friedl, Z., Slais, K., *J. Chromatogr. A* 2001, 916, 65-71). Unfortunately, their fluorescence had to be excited below 400 nm, outside of the wavelength range of visible light.

Undesirably, the known pI markers often have widely varying structural properties, variable (and often poor) aqueous solubilities (high octanol–water partition coefficients or log $P_{ow}$ values); their pI values cover only certain segments of the needed 3<pI<10 range; the $pK_a$ values of the functional groups that straddle the pI value on the acidic and basic sides and are closest to it ($pK_a^{closest}$) are often farther away from the pI value than 2 (i.e., $|pI-pK_a^{closest}|>2$), or, expressed in another way, the difference between the closest pKa values that straddle the pI value, $\Delta pK_a=(pK_a^{just\ above\ pI}-pK_a^{just\ below\ pI})>4$, the maximum values that still yield adequately (though not greatly) focusing ampholytes (H. Svensson, *Acta Chem. Scand.* 1962, 16, 456-466). The effective charge of the ampholyte as a function of pH, z(pH), is a material characteristic of the ampholyte. If an ampholyte is to be a rapidly focusing one, it must have a $[-dz(pH)/d(pH)]$ value in the vicinity of its isoelectric point, known as $[-dz(pH)/d(pH)_{pI}]$, that is as large as possible (Giddings, J. C., *Unified Separation Science*, Wiley-Interscience, New York, 1991, pp 180-182). According to Rilbe (Rilbe, H., *Ann. N.Y. Acad. Sci.* 209 (1973) 11), $[-dz(pH)/d(pH)_{pI}]=\ln 10/[1+0.5(10^{(pKa2-pKa1)/2})]$ and has a minimum required value of 0.045 in order to focus acceptably. Thus, in order to be an outstanding ampholyte, the pKa values that straddle the pI value need to be as close as possible. A few of the known non-peptide pI markers have $[-dz(pH)/d(pH)_{pI}]$ values in the 0.1 to 0.8 range (Slais, K., Friedl, Z., *J. Chromatogr. A* 661 (1994) 249-256, and Horka, M., Willimann, T., Blum, M., Nording, P., Friedl, Z., Slais, K., *J. Chromatogr. A* 916 (2001) 65-71), but very few have $[-dz(pH)/d(pH)_{pI}]$ values above 0.9 (Slais, K., Friedl, Z., *J. Chromatogr. A* 695 (1995) 113-122).

Thus, there is still an unfilled need for families of non-peptide ampholytes covering a wide range of pI values with $[-dz(pH)/d(pH)_{pI}]$ values greater than 0.9.

Additionally, up to now, compounds used as pI markers had to be selected by extensive, time consuming trial and error searches (e.g., Righetti, P. G., Gianazza, E., *J. Chromatogr.* 1977, 137, 171-181), because there were no known correlations between the structure of an ampholyte and its pI value. For example, the respective $pK_a$ values of pyridine-2-carboxylic acid (picolinic acid) are 1 and 5.21 yielding pI=3.105 and a $|pI-pK_a^{closest}|=2.1$; those of pyridine-3-carboxylic acid (nicotinic acid) are 2.07 and 4.66 yielding a pI=3.365 and a $|pI-pK_a^{closest}|=1.3$; while those of pyridine-4-carboxylic acid (isonicotinic acid) are 1.8 and 4.88 yielding a pI of 3.34 and a $|pI-pK_a^{closest}|=1.54$. The $pK_a$ values are often significantly different even when two identical functional groups are connected to the same core molecule: for example, the $pK_a$ values of the two carboxylic acid groups in 1,2-benzenedicarboxylic acid are 2.76 and 4.92, those in 1,4-benzenedicarboxylic acid are 3.60 and 4.50.

Thus, there is still an unfulfilled need for one or more families of small molecule nonpeptide pI markers that have pI values in the 3<pI<10 range, are characterized by small $|pI-pK_a^{closest}|$ values, small $\Delta pK_a=(pK_a^{just\ above\ pI}-pK_a^{just\ below\ pI})$ values and high $[-dz(pH)/d(pH)_{pI}]$ values assuring rapid focusing, have strong UV absorbance, have adequate fluorescence that can be excited by visible light (preferably by the commonly used, commercially available lasers or light emitting diodes, LEDs), have pH-independent fluorescence properties, have adequate water solubility and preferably, have a common core structure that controls light absorbance and fluorescence, and have substituents attached to the core that control the pI value of the ampholyte without altering the light absorption and fluorescence properties of the core. The present invention seeks to fulfill this need and provides further related advantages.

SUMMARY OF THE INVENTION

In one aspect, the invention provides pI markers. In one embodiment, the pI marker is a compound, comprising:
(a) an aryl core having at least three substituents;
(b) a first substituent comprising a first sulfonamido group, wherein the first sulfonamido group comprises a first weak electrolyte group;
(c) a second substituent comprising a second sulfonamido group, wherein the second sulfonamido group comprises a second weak electrolyte group; and
(d) a third substituent comprising a group selected from the group consisting of a charge-balancing group and a non-charged group.

Representative aryl cores include 1,3,5-trisubstituted benzene, 1,3,6-trisubstituted naphthalene, and 1,3,6-trisubstituted pyrene cores, wherein the 3- and 5-substituents of the benzene ring, the 1- and 6-substituents of the naphthalene ring, and the 1- and 3-substituents of the pyrene ring are the first and second substituents, respectively.

In certain embodiments, the aryl core is a 1,3,6-trisubstituted pyrene further comprising a fourth substituent at position 8 selected from the group consisting of amine, ether, and thioether. In certain embodiments, the fourth substituent further comprises a functional group effective for covalently coupling the compound to a second compound to provide a conjugate.

In one embodiment, the compound has the formula:

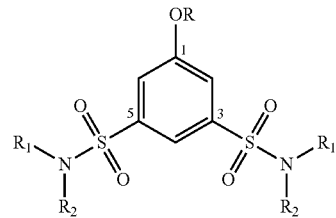

wherein
R is selected from the group consisting of
—$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20,
wherein each is coupled to hydrogen, a non-charged group, or at least one moiety selected from the group consisting of amino, secondary amine, tertiary amine, quaternary amine, azaaryl, hydroxyaryl, carboxylic acid or carboxylate, sulfonic acid or sulfonate, and hydrogensulfate or sulfate group; and
$R_1$ and $R_2$ at each occurrence are independently selected from the group consisting of
—$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20,
wherein each is coupled to hydrogen, a non-charged group, or at least one moiety selected from the group consisting of amino, secondary amine, tertiary amine, azaaryl, hydroxyaryl, and carboxylic acid group.

In another embodiment, the compound has the formula:

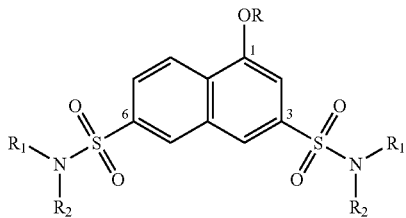

wherein
R is selected from the group consisting of
—$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20,
wherein each is coupled to hydrogen, a non-charged group, or at least one moiety selected from the group consisting of amino, secondary amine, tertiary amine, quaternary amine, azaaryl, hydroxyaryl, carboxylic acid or carboxylate, sulfonic acid or sulfonate, and or hydrogensulfate or sulfate group; and $R_1$ and $R_2$ at each occurrence are independently selected from the group consisting of
- $-(CH_2)_n-$ where n is from 1 to 12,
- $-(CH_2CH<)_n-$ where n is from 1 to 12,
- $-(CH_2CH_2O)_n-$ where n is from 1 to 20, and
- $-(CH_2CH(OH)CH_2O)_n-$ where n is from 1 to 20, wherein each is coupled to hydrogen, a non-charged group, or at least one moiety selected from the group consisting of amino, secondary amine, tertiary amine, azaaryl, hydroxyaryl, and carboxylic acid group.

In a further embodiment, the compound has the formula:

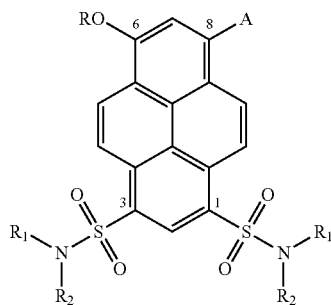

wherein

A is selected from the group consisting of $OR_3$, $SR_3$, and $N(R_4)(R_5)$, wherein $R_3$ is selected from the group consisting of
- $-(CH_2)_n-$ where n is from 1 to 12,
- $-(CH_2CH<)_n-$ where n is from 1 to 12,
- $-(CH_2CH_2O)_n-$ where n is from 1 to 20, and
- $-(CH_2CH(OH)CH_2O)_n-$ where n is from 1 to 20, wherein each is coupled to hydrogen, a non-charged group, or at least one moiety selected from the group consisting of amino, secondary amine, tertiary amine, quaternary amine, azaaryl, hydroxyaryl, and carboxylic acid group;

wherein $R_4$ and $R_5$ are independently selected from the group consisting of
hydrogen,
- $-(CH_2)_n-$ where n is from 1 to 12,
- $-(CH_2CH<)_n-$ where n is from 1 to 12,
- $-(CH_2CH_2O)_n-$ where n is from 1 to 20, and
- $-(CH_2CH(OH)CH_2O)_n-$ where n is from 1 to 20, wherein each of $-(CH_2)_n-$, $-(CH_2CH<)_n-$, $-(CH_2CH_2O)_n-$, and $-(CH_2CH(OH)CH_2O)_n-$ is coupled to hydrogen, a non-charged group, or at least one moiety selected from the group consisting of amino, secondary amine, tertiary amine, quaternary amine, azaaryl, hydroxyaryl, and carboxylic acid group;

R is selected from the group consisting of
- $-(CH_2)_n-$ where n is from 1 to 12,
- $-(CH_2CH<)_n-$ where n is from 1 to 12,
- $-(CH_2CH_2O)_n-$ where n is from 1 to 20, and
- $-(CH_2CH(OH)CH_2O)_n-$ where n is from 1 to 20, wherein each is coupled to hydrogen, a non-charged group, or at least one moiety selected from the group consisting of amino, secondary amine, tertiary amine, quaternary amine, azaaryl, hydroxyaryl, carboxylic acid or carboxylate, sulfonic acid or sulfonate, and or hydrogensulfate or sulfate group; and $R_1$ and $R_2$ at each occurrence are independently selected from the group consisting of
hydrogen,
- $-(CH_2)_n-$ where n is from 1 to 12,
- $-(CH_2CH<)_n-$ where n is from 1 to 12,
- $-(CH_2CH_2O)_n-$ where n is from 1 to 20, and
- $-(CH_2CH(OH)CH_2O)_n-$ where n is from 1 to 20, wherein each of $-(CH_2)_n-$, $-(CH_2CH<)_n-$, $-(CH_2CH_2O)_n-$, and $-(CH_2CH(OH)CH_2O)_n-$ is coupled to hydrogen, a non-charged group, or at least moiety selected from the group consisting of amino, secondary amine, tertiary amine, azaaryl, hydroxyaryl, and carboxylic acid group.

In another aspect, the invention provides reagents useful for labeling molecules of interest. In one embodiment, the compound has the formula:

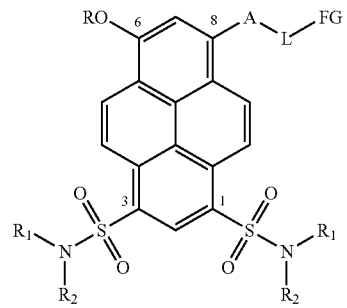

wherein

A is selected from the group consisting of O, S, NR, and NH;

L is a linker covalently coupling A to FG;

FG is a functional group reactive to covalently couple the compound to a compound of interest;

R is selected from the group consisting of
- $-(CH_2)_n-$ where n is from 1 to 12,
- $-(CH_2CH<)_n-$ where n is from 1 to 12,
- $-(CH_2CH_2O)_n-$ where n is from 1 to 20, and
- $-(CH_2CH(OH)CH_2O)_n-$ where n is from 1 to 20, wherein each is coupled to hydrogen, a non-charged group, or at least one moiety selected from the group consisting of amino, secondary amine, tertiary amine, quaternary amine, azaaryl, hydroxyaryl, carboxylic acid or carboxylate, sulfonic acid or sulfonate, and hydrogensulfate or sulfate group; and $R_1$ and $R_2$ at each occurrence are independently selected from the group consisting of
- $-(CH_2)_n-$ where n is from 1 to 12,
- $-(CH_2CH<)_n-$ where n is from 1 to 12,
- $-(CH_2CH_2O)_n-$ where n is from 1 to 20, and
- $-(CH_2CH(OH)CH_2O)_n-$ where n is from 1 to 20, wherein each is coupled to hydrogen, a non-charged group, or at least moiety selected from the group consisting of amino, secondary amine, tertiary amine, azaaryl, hydroxyaryl, and carboxylic acid group.

Representative functional groups include amino, secondary amine, carboxylic acid, and reactive carboxylic acid ester, acrylate ester or amide, alkyl or arylboronate, and alkylhalide groups.

In a further aspect, the invention provides a conjugate comprising a reagent of the invention covalently coupled to a molecule of interest. Representative molecules of interest include sugars, polysaccharides, amino acids, peptides, and proteins.

In another aspect, a method for establishing the shape of a pH gradient between an anode and a cathode across an electrophoretic device is provided. In one embodiment, the method includes:

(a) introducing one or more pI markers of the invention having a known pI value into an electrophoretic device; and (b) applying an electric field sufficient for a period of time sufficient to separate and concentrate the one or more pI markers.

In one embodiment, the method further comprises determining the position of the separated and concentrated pI markers in the electrophoretic device, and plotting their pI values as a function of their position in the electrophoretic device thereby establishing the shape of pH gradient in the device.

In another embodiment, the method further comprises introducing one or more ampholytic analytes into the electrophoretic device prior to or after applying the electric field, wherein applying the electric field is effective to separate and concentrate the one or more pI markers and the one or more ampholytic analytes. In one embodiment, the method further comprises determining the position of the separated and concentrated ampholytic analytes in the electrophoretic device, thereby establishing the pIs of the one or more ampholytic analytes.

In a further embodiment, the further comprises introducing one or more ampholytic analytes into the electrophoretic device and applying an electric field sufficient for a period of time sufficient to separate and concentrate the one or more ampholytic analytes. In one embodiment, the method further comprises determining the position of the separated and concentrated ampholytic analytes in the electrophoretic device, thereby establishing the pIs of the one or more ampholytic analytes.

In another aspect of the invention, a method for labeling a carbohydrate is provided. In the method, a carbohydrate is reacted with a suitable reagent of the invention to provide a labeled carbohydrate.

In a further aspect, the invention provides a method for electrophoretic separation and concentration of one or more carbohydrate analytes. In one embodiment, the method includes:

(a) reacting one or more carbohydrates with a suitable reagent of the invention to provide one or more ampholytic carbohydrates;

(b) introducing the one or more ampholytic carbohydrates into an electrophoretic device; and (c) applying an electric field sufficient for a period of time sufficient to separate and concentrate the one or more ampholytic carbohydrates.

In another aspect, the invention provides a method for chromatographic separation and concentration of one or more carbohydrate analytes. In one embodiment, the method includes:

(a) reacting one or more carbohydrates with a suitable reagent of the invention to provide one or more ampholytic carbohydrates;

(b) introducing the one or more ampholytic carbohydrates into a liquid chromatographic device; and (c) applying an eluent sufficient for a period of time sufficient to separate and concentrate the one or more ampholytic carbohydrates.

In a further aspect, the invention provides a compound having the formula:

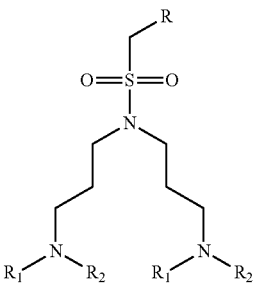

wherein

R is selected from the group consisting of
—$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20, wherein each is coupled to hydrogen, a non-charged group, or at least one moiety selected from the group consisting of amino, secondary amine, tertiary amine, quaternary amine, azaaryl, hydroxyaryl, carboxylic acid or carboxylate, sulfonic acid or sulfonate, and hydrogensulfate or sulfate group; and $R_1$ and $R_2$ at each occurrence are independently selected from the group consisting of
—$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20, wherein each is coupled to hydrogen, a non-charged group, or at least moiety selected from the group consisting of amino, secondary amino, tertiary amino, azaaryl, hydroxyaryl, and carboxylic acid group.

In another aspect, the invention provides a compound having the formula:

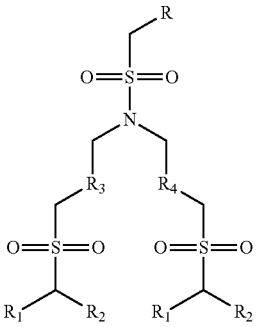

wherein

R is selected from the group consisting of
—$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20, wherein each is coupled to hydrogen, a non-charged group, or at least one moiety selected from the group consisting of amino, secondary amine, tertiary amine, quaternary amine, azaaryl, hydroxyaryl, carboxylic acid or carboxylate, sulfonic acid or sulfonate, and or hydrogensulfate or sulfate group;

$R_1$ and $R_2$ at each occurrence are independently selected from the group consisting of —$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20, wherein each is coupled to hydrogen, a non-charged group, or at least moiety selected from the group consisting of amino, secondary amine, tertiary amine, azaaryl, hydroxyaryl, and carboxylic acid group; and $R_3$ and $R_4$ are independently selected from the group consisting of —$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20, wherein each is coupled to hydrogen, a non-charged group, or at least one moiety selected from the group consisting of amino, secondary amine, tertiary amine, quaternary amine, azaaryl, hydroxyaryl, carboxylic acid or carboxylate, sulfonic acid or sulfonate, and or hydrogensulfate or sulfate group.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1A:
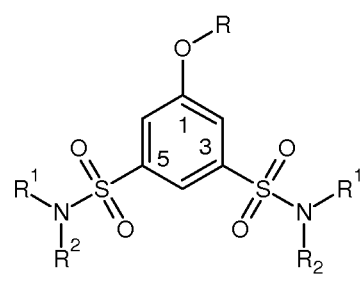
FIGS. 1A-1D illustrate representative classes of the UV-absorbing and fluorescent pI markers of the invention.
Figure 1B:
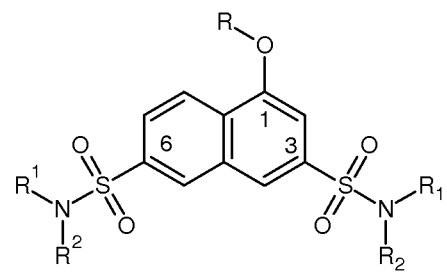
Figure 1C:
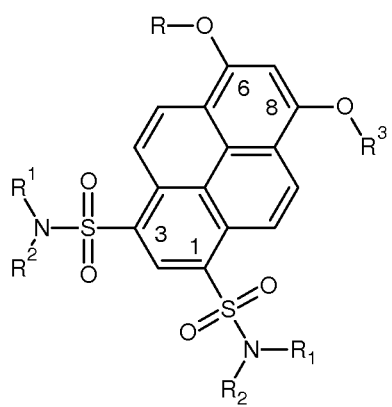
Figure 1D:
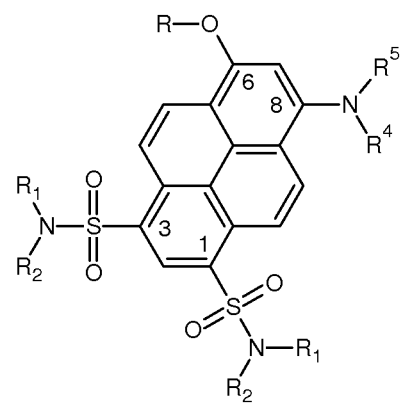

The present invention provides pI markers, methods for using the pI markers in isoelectric focusing, reactive pI markers useful for labeling molecules of interest, conjugates of the pI markers and molecules of interest, and methods for separation and concentration of the conjugates. In certain embodiments, the pI markers are UV-absorbing, fluorescent, and reactive rendering the markers useful as fluorescent labeling reagents.

When ampholytic compounds (i.e., ampholytes) are present in solution at a low concentration, their charge-state depends on their environment. At a certain characteristic pH value, the net charge—and consequently the electrophoretic mobility—of an ampholyte compound becomes zero. That pH value is known as the pI value of the ampholytic compound. When two ampholytic compounds have different pI values, their net charge becomes zero at different pH values. If a pH gradient is established in an electric field, the two ampholytic species achieve zero net charge at different points of the pH gradient that can result in their separation. Such separations are called isoelectric focusing (IEF) separations. pI markers are compounds having known pI values and an observable reporting group (e.g., absorbance or fluorescence) and are used to determine pH gradients in electric fields and to ascertain the pI of ampholytic compounds focused in such gradients.

The present invention provides families of novel, low molecular weight, UV-absorbing and fluorescent pI markers for use in analytical and preparative-scale isoelectric focusing (IEF) and isoelectric trapping (IET) separations and as tagging reagents in derivatization reactions. The primary application areas of the compounds are in the separation, purification, enrichment, concentration or conditioning of both small and large molecular weight ampholytic compounds, such as small ampholytic pharmaceuticals (natural and non-natural amino acids, amino phenolics, amino phosphonic acids, amino phosphates), oligo- and polypeptides, proteins, prions, viruses, organelles, cells and ampholytic particles, and the conversion of non-ampholytic materials, such as carbohydrates into ampholytes permitting their subsequent separation and analysis by isoelectric focusing and trapping.

pI Markers

In one aspect, the invention provides pI markers. The pI markers of the invention include (a) an aryl core having at least three substituents;

(b) a first substituent comprising a first sulfonamido group, wherein the first sulfonamido group comprises a first weak electrolyte group;

(c) a second substituent comprising a second sulfonamido group, wherein the second sulfonamido group comprises a second weak electrolyte group; and (c) a third substituent comprising a group selected from the group consisting of a charge-balancing group and a non-charged group.

By virtue of the aryl core, the markers are UV-absorbing. In certain embodiments, the markers are also fluorescent. Suitable aryl cores include benzene, naphthalene, and pyrene cores. Representative aryl cores include 1,3,5-trisubstituted benzenes, 1,3,6-trisubstituted naphthalenes, and 1,3,6-trisubstituted pyrenes, wherein the 3 and 5 substituents of the benzene ring, the 1 and 6-substituents of the naphthalene ring and the 1 and 3-substituents of the pyrene ring are the first and second substituents, respectively. Representative pI markers of the invention depicting the core numbering scheme are illustrated in FIG. 1.

The first and second substituents are sterically and electronically isolated from each other. Each of the first and second substituents includes a weak electrolyte group. As used herein, the term "weak electrolyte" refers to an acidic group that is partially dissociated in aqueous solution and having a pKa from about 1 to 14, preferably from about 1 to 13, or a basic group whose conjugate acid form is partially dissociated in aqueous solution and having a pKa from about 1 to 14, preferably from about 1 to 13. As used herein, the term "buffering group" refers to a weak electrolyte. For example, an aspartic acid or lysine has three buffering groups.

In certain embodiments, the first and second weak electrolyte groups are the same. In other embodiments, the first and second weak electrolyte groups are different.

Suitable weak electrolyte groups include amino, secondary amino, tertiary amino, azaryl, hydroxyaryl, carboxylic acid, carboxylate, sulfonic acid, sulfonate, hydrogen sulfate, and sulfate groups. Representative weak electrolyte groups are illustrated in FIGS. 2-29, which depict representative pI markers of the invention.

The third substituent includes a charge-balancing group or a non-charged group.

As used herein, the term "charge-balancing group" refers to a weak electrolyte group or strong electrolyte group (strong electrolyte defined as a group that is substantially completely dissociated in an aqueous solution at a pH from about 1 to 14). The charge-balancing group can have a permanent positive or negative charge (e.g., quaternary ammonium or sulfonate). The charge balancing group renders the net charge of the compounds of the invention zero at the pH equal to the pI. As used herein, the term "titrating group" refers to a charge-balancing group.

Suitable charge-balancing groups include amino, secondary amino, tertiary amino, quaternary amino, azaryl, hydroxyaryl, carboxylic acid, carboxylate, sulfonic acid, sulfonate, hydrogensulfate, and sulfate groups. Representative charge-balancing groups are illustrated in FIGS. 2-29, which depict representative pI markers of the invention.

As used herein, the term "non-charged group" refers to a neutral group (i.e., having no net charge) that is present to impart advantageous solubility properties to the compound. For use in aqueous environments, the non-charged group is a hydrophilic group that improves the water solubility of the marker.

Figure 10:
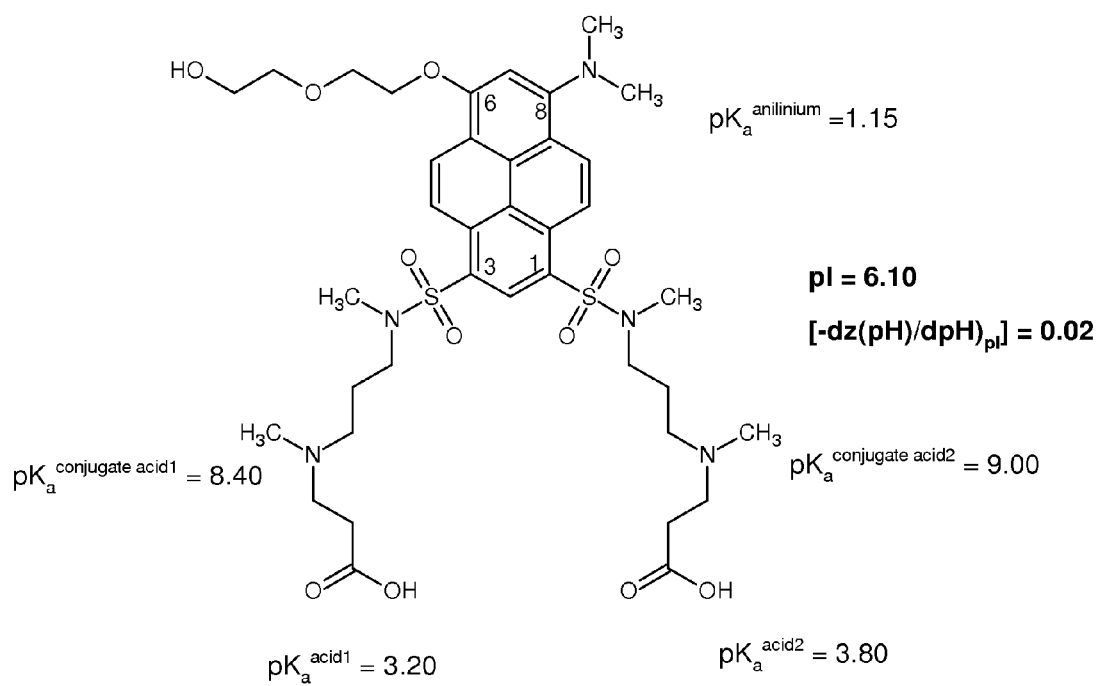
FIG. 10 illustrates a representative pI marker of the invention.
Figure 11:
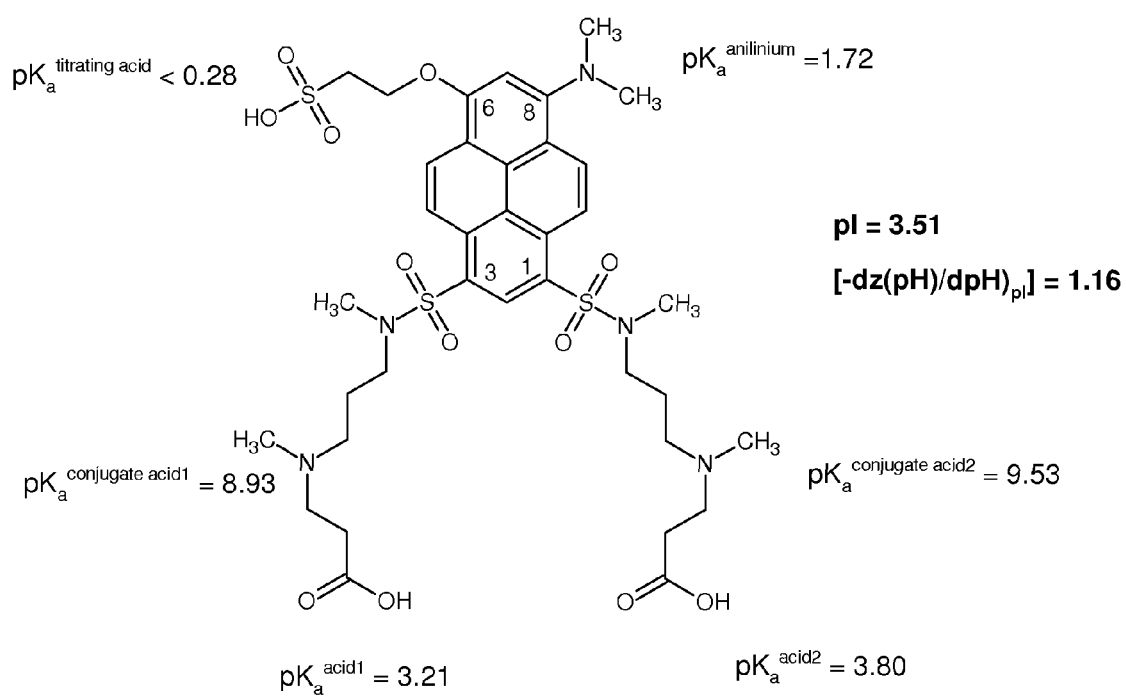
FIG. 11 illustrates a representative pI marker of the invention.
Figure 14:
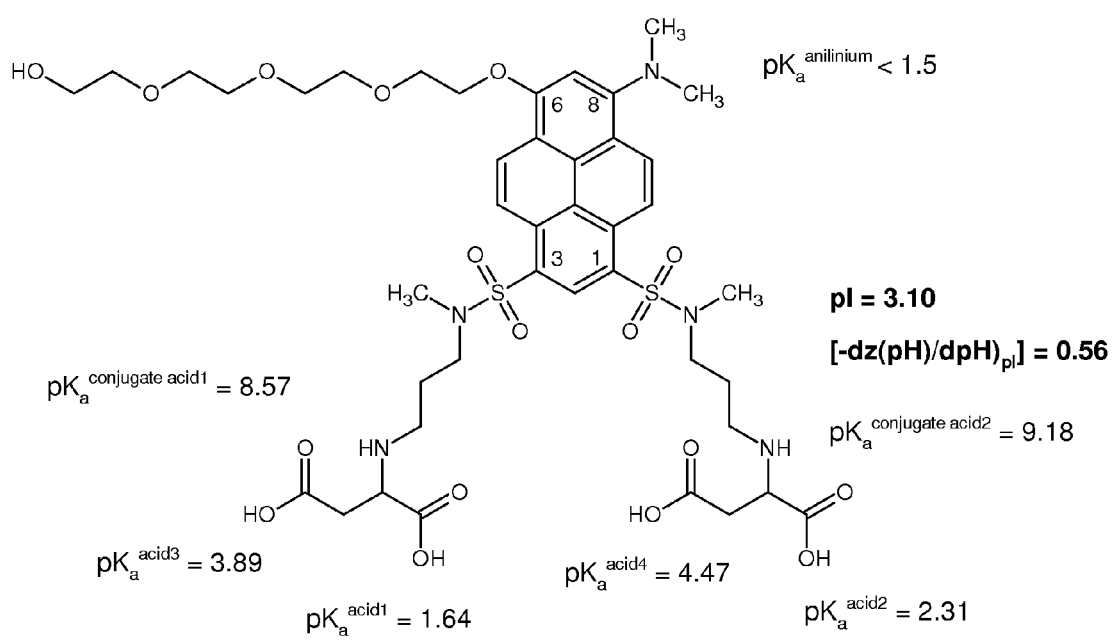
FIG. 14 illustrates a representative pI marker of the invention.
Figure 18:
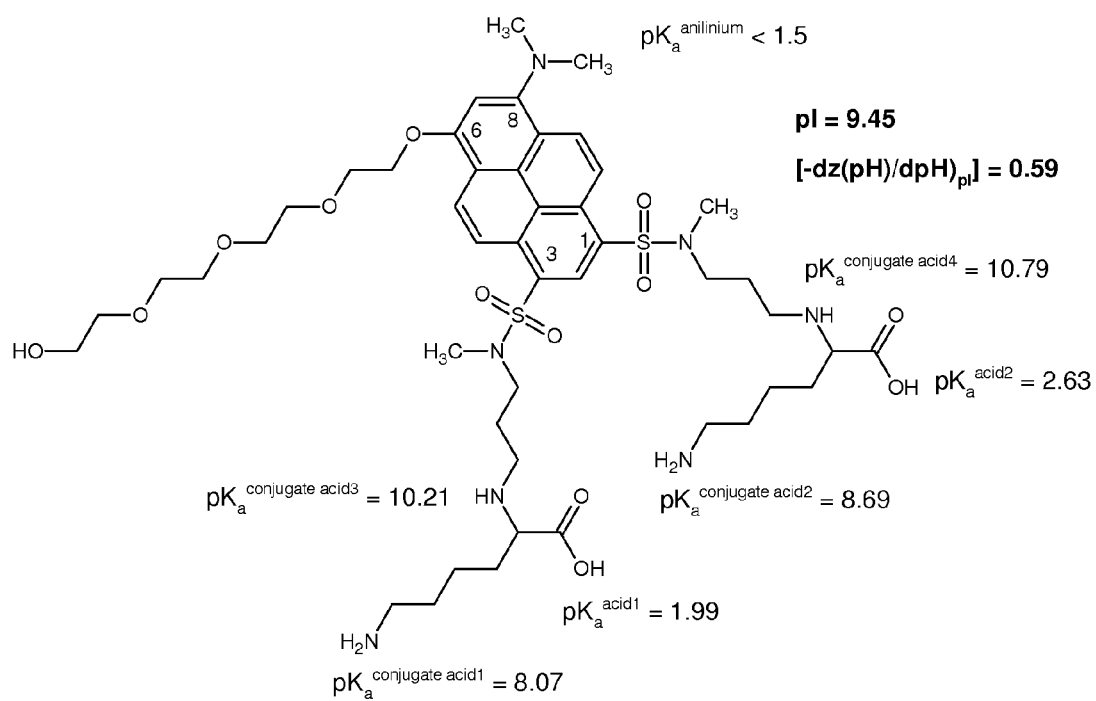
FIG. 18 illustrates a representative pI marker of the invention.
Figure 19:
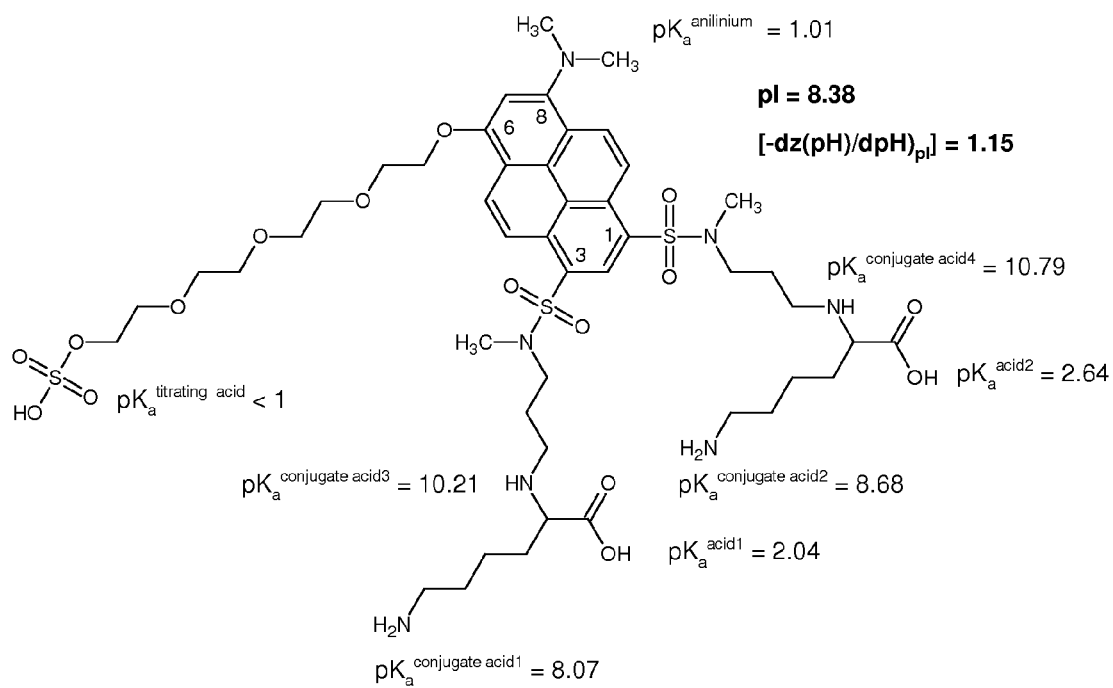
FIG. 19 illustrates a representative pI marker of the invention.

Suitable non-charged groups include poly(ethylene glycol) moieties, poly(propylene glycol) moieties, linear oligo- and polysaccharide moieties, branched oligo- and polysaccharide moieties, and cyclic oligo- and polysaccharide moieties. Representative non-charged groups are illustrated in FIGS. 10, 14, and 18, which depict representative pI markers of the invention.

In certain embodiments, the pI marker is a pyrene and further includes a fourth substituent. In certain of these embodiments, the aryl core is a 1,3,6-trisubstituted pyrene and the fourth substituent is at position 8. Suitable fourth substituents include amine, ether, and thioether substituents in which the amine nitrogen, ether oxygen, or thioether sulfur is covalently attached to the pyrene core.

In one embodiment, the fourth substituent is an ether group further comprising a weak electrolyte group, a charge-balancing group, or a non-charged group. In another embodiment, the fourth substituent is an amine group further comprising a weak electrolyte group, a charge-balancing group, or a non-charged group. In a further embodiment, the fourth substituent is a thioether group further comprising a weak electrolyte group, a charge-balancing group, or a non-charged group.

In one embodiment, the pI marker of the invention has formula (I):

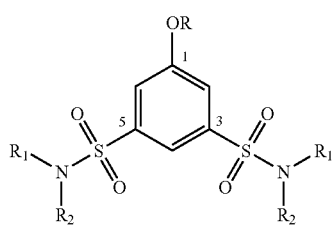

(I)

wherein

R is selected from the group consisting of
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each is coupled to H, a non-charged group, or at least one moiety selected from the group consisting of NH$_2$, NHR, N(R)$_2$, N(R)$_3^+$, azaaryl, hydroxyaryl, carboxylic acid or carboxylate, sulfonic acid or sulfonate, and hydrogensulfate or sulfate group; and R$_1$ and R$_2$ at each occurrence are independently selected from the group consisting of
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each is coupled to H, a non-charged group, or at least one moiety selected from the group consisting of NH$_2$, NHR, N(R)$_2$, azaaryl, hydroxyaryl, and carboxylic acid group.

In another embodiment, the pI marker of the invention has formula (II):

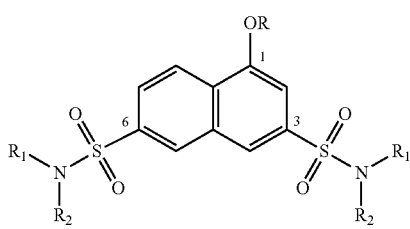

(II)

wherein

R is selected from the group consisting of
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each is coupled to H, a non-charged group, or at least one moiety selected from the group consisting of NH$_2$, NHR, N(R)$_2$, N(R)$_3^+$, azaaryl, hydroxyaryl, carboxylic acid or carboxylate, sulfonic acid or sulfonate, and hydrogensulfate or sulfate group; and R$_1$ and R$_2$ at each occurrence are independently selected from the group consisting of
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each is coupled to H, a non-charged group, or at least one moiety selected from the group consisting of NH$_2$, NHR, N(R)$_2$, azaaryl, hydroxyaryl, and carboxylic acid group.

In a further embodiment, the pI marker of the invention has formula (III):

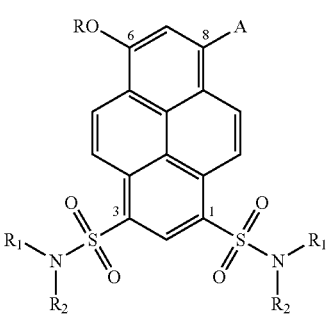

(III)

wherein

A is selected from the group consisting of OR$_3$, SR$_3$, and N(R$_4$)(R$_5$), wherein R$_3$ is selected from the group consisting of
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each is coupled to H, a non-charged group, or at least one moiety selected from the group consisting of NH$_2$, NHR, N(R)$_2$, N(R)$_3^+$, azaaryl, hydroxyaryl, and carboxylic acid group;

wherein R$_4$ and R$_5$ are independently selected from the group consisting of
hydrogen,
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each of the last four is coupled to H, a non-charged group, or at least one moiety selected from the group consisting of NH$_2$, NHR, N(R)$_2$, N(R)$_3^+$, azaaryl, hydroxyaryl, and carboxylic acid group;

R is selected from the group consisting of
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each is coupled to H, a non-charged group, or at least one moiety selected from the group consisting of NH$_2$, NHR, N(R)$_2$, N(R)$_3^+$, azaaryl, hydroxyaryl, carboxylic acid or carboxylate, sulfonic acid or sulfonate, and hydrogensulfate or sulfate group; and R$_1$ and R$_2$ at each occurrence are independently selected from the group consisting of
hydrogen,
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each of the last four is coupled to H, a non-charged group, or at least one moiety selected from the group consisting of $NH_2$, NHR, $N(R)_2$, azaaryl, hydroxyaryl, and carboxylic acid group.

In one embodiment, $R_1$ and $R_2$ are not both hydrogen.

In one embodiment, A is $N(R_4)(R_5)$ and $R_4$ and $R_5$ are hydrogen.

For the markers of formulas (I)-(III), in certain embodiments, $R_1$ at each occurrence is the same. In other embodiments, $R_1$ at each occurrence is different. In certain embodiments, $R_1$ at each occurrence includes a group independently selected from amino, secondary amino, tertiary amino, azaryl, hydroxyaryl, carboxylic acid, carboxylate, sulfonic acid, sulfonate, hydrogen sulfate, and sulfate groups. In certain embodiments, R includes a group selected from amino, secondary amino, tertiary amino, quaternary amino, azaryl, hydroxyaryl, carboxylic acid, carboxylate, sulfonic acid, sulfonate, hydrogensulfate, and sulfate groups. In other embodiments, R includes a moiety selected from a group comprising a poly(ethylene glycol) moiety, a poly(propylene glycol) moiety, a linear oligo- or polysaccharide moiety, a branched oligo- or polysaccharide moiety, and a cyclic oligo- or polysaccharide moiety.

In certain embodiments of the markers of formulas (I)-(III), $R_1$ and $R_2$ independently at each occurrence can be taken together with the nitrogen to which they are attached to form a heterocyclic ring, such as a piperidine ring, a piperazine ring, or a morpholine ring. See, for example, FIG. 21.

FIG. 1 illustrates classes of the UV-absorbing and fluorescent pI markers of the invention. The following is a listing of suitable substituents R, $R_1$, $R_2$, $R_3$, $R_4$, and $R_5$ for the pI markers illustrated in FIG. 1, where at least one group is selected for R, $R_1$, $R_2$, $R_3$, $R_4$ and $R_5$, when present, from their respective list:

| R | (—$CH_2$—)$_n$ or (—$CH_2$—CH<)$_n$ | 0 < n < 12 |
|---|---|---|
|   | (—$CH_2CH_2O$—)$_n$ | 1 < n < 20 |
|   | (—$CH_2CH(OH)CH_2O$—)$_n$ | 1 < n < 20 | each connected to H, a non-charged group, or at least one $NH_2$, NHR, $N(R)_2$, $N(R)_3^+$, azaaryl, hydroxyaryl, carboxylic acid or carboxylate, sulfonic acid or sulfonate, or hydrogensulfate or sulfate moiety;

| $R_1$ | (—$CH_2$—)$_n$ or (—$CH_2$—CH<)$_n$ | 1 < n < 12 |
|---|---|---|
|   | (—$CH_2CH_2O$—)$_n$ | 1 < n < 20 |
|   | (—$CH_2CH(OH)CH_2O$—)$_n$ | 1 < n < 20 | each connected to H, a non-charged group, or at least one $NH_2$, NHR, $N(R)_2$, azaaryl, hydroxyaryl, or carboxylic acid moiety, or their combinations;

| $R_2$ | (—$CH_2$—)$_n$ or (—$CH_2$—CH<)$_n$ | 0 < n < 12 |
|---|---|---|
|   | (—$CH_2CH_2O$—)$_n$ | 1 < n < 20 |
|   | (—$CH_2CH(OH)CH_2O$—)$_n$ | 1 < n < 20 | each connected to H, a non-charged group, or at least one $NH_2$, NHR, $N(R)_2$, azaaryl, hydroxyaryl, or carboxylic acid moiety, or their combinations, same as or different from $R_1$;

| $R_3$ | (—$CH_2$—)$_n$ or (—$CH_2$—CH<)$_n$ | 0 < n < 12 |
|---|---|---|
|   | (—$CH_2CH_2O$—)$_n$ | 1 < n < 20 |
|   | (—$CH_2CH(OH)CH_2O$—)$_n$ | 1 < n < 20 | each connected to H, a non-charged group, or at least one $NH_2$, NHR, $N(R)_2$, azaaryl, hydroxyaryl, or carboxylic acid moiety, or their combinations, same as or different from $R_1$ or $R_2$ or both;

| $R_4$ | (—$CH_2$—)$_n$ or (—$CH_2$—CH<)$_n$ | 0 < n < 12 |
|---|---|---|
|   | (—$CH_2CH_2O$—)$_n$ | 1 < n < 20 |
|   | (—$CH_2CH(OH)CH_2O$—)$_n$ | 1 < n < 20 | each connected to H, a non-charged group, or at least one $NH_2$, NHR, $N(R)_2$, azaaryl, hydroxyaryl, or carboxylic acid group, or their combinations, same as or different from $R_1$ or $R_2$ or $R_3$ or two or three of them; and

| $R_5$ | (—$CH_2$—)$_n$ or (—$CH_2$—CH<)$_n$ | 0 < n < 12 |
|---|---|---|
|   | (—$CH_2CH_2O$—)$_n$ | 1 < n < 20 |
|   | (—$CH_2CH(OH)CH_2O$—)$_n$ | 1 < n < 20 | each connected to H, a non-charged group, or at least one $NH_2$, NHR, $N(R)_2$, azaaryl, hydroxyaryl, or carboxylic acid moiety, or their combinations, same as or different from $R_1$ or $R_2$ or $R_3$ or two or three of them.

It will be appreciated that for the ampholytes of formulas (I), (II), and (III), the combination of the electrolyte groups in R, $R_1$ and $R_2$ lead to a species that can have a negative, net zero and a positive charge as the pH of the solution is varied from 0 to 14.

In the above listings, NHR, $N(R)_2$, and $N(R)_3^+$ refer to secondary, tertiary, and quaternary amine groups, respectively. For NHR, $N(R)_2$, and $N(R)_3^+$, in certain embodiments, R in these groups is as described above for R (i.e., (—$CH_2$—)$_n$ or (—$CH_2$—CH<)$_n$, where 0<n<12; (—$CH_2CH_2O$—)$_n$, where 1<n<20; and (—$CH_2CH(OH)CH_2O$—)$_n$, where 1<n<20; each connected to hydrogen). In certain embodiments R is a C1-C12 alkyl group.

As described above, the inventors have discovered that, unexpectedly, certain aryl core structures can be bis-substituted with identical (monoprotic sulfonamide), (diprotic sulfonamide) or (triprotic sulfonamide) groups in such a way that the difference(s) between the $pK_a$ value(s) of the identical protic group(s) in the two sulfonamide groups are shifted by less than 0.7, permitting the methodical creation of ampholytes whose $[-dz(pH)/d(pH)_{pI}]$ values are greater than 0.9 and, thus, are outstanding focusers. Core structures of aryl-bis(sulfonamides) and their substitution positions have been identified that cause minimum shifts in the $pK_a$ values of the identical weak electrolyte functional groups that are connected to the sulfonamido groups and serve as the buffering groups in the ampholyte. Appropriate titrating groups have been identified and their attachment positions on the core aryl-bis(sulfonamides) led to the formation of rapidly focusing ampholytes. Members of the pI marker families have been synthesized, analytically characterized, and their pI values determined. The pI makers have been used in capillary isoelectric focusing separations.

The pI markers of the invention (also referred to herein as "ampholytes") have core scaffolds that are bis-substituted aromatic sulfonamides: (a) the structure of the ampholyte corresponds to one of the general structures shown in FIG. 1, (b) optionally have identical sulfonamido groups, (c) at least one of the substituents of each sulfonamido group contain at least one weak electrolyte group (buffering group), (d) the identical weak electrolyte functional groups (buffering groups) are electronically and sterically adequately isolated from each other leading to $pK_a$ shifts of less than about 0.7 and (e) the aromatic core compound contains at least one other substituent group that can serve either as a non-charged group, or as a titrating group (anionic or cationic charge balancing group) permitting the formation of the desired ampholyte.

Using each of the general structures in FIG. 1, three sets of increasingly complex ampholytes can be constructed by selecting the appropriate substituents for the sulfonamido groups ($R_1$ and $R_2$), for the aryloxy group(s) (R and $R_3$), and, when present, for the anilinic 8-amino group ($R_4$ and $R_5$). As examples, a few representative implementations of general structure D that lead to the different classes of ampholytes discussed below are shown in FIGS. 2 through 20, along with the corresponding $pK_a$ values, the resulting pI value and the $[-dz(pH)/d(pH)_{pI}]$ value. Because the anilinic 8-amino group in Construct D is a very weakly basic group (its conjugate acid form is characterized by $pK_a^{anilinium}<0.5$ when both $R_4$ and $R_5$ are H, and $pK_a^{anilinium}<1.5$ when both $R_4$ and $R_5$ contain at least one $CH_2$— unit), the 8-amino group is less than 5% protonated in the 3<pH range that is used in isoelectric focusing and trapping. Thus, the anilinic 8-amino group has minimal effects on the 3<pI values of the invented ampholytes.

As shown in FIG. 1, the present invention provides three, practically useful, generic ampholyte classes: (I) aryl-bis (monoprotic sulfonamide) ampholytes, (II) aryl-bis(diprotic sulfonamide) ampholytes, and (III) aryl-bis(triprotic sulfonamide) ampholytes. Aryl-bis(tetraprotic sulfonamide) ampholytes and aryl-bis(pentaprotic sulfonamide) ampholytes can be constructed, but the 3<pI<10 range can already be adequately covered using only members of the first three ampholyte classes. Within each class, both pI<7 and 7<pI ampholyte families can be made, and within each families, there are multiple possible implementation strategies, as discussed below.

Class (I) Ampholytes: aryl-bis(monoprotic sulfonamide) Ampholytes

Figure 2:
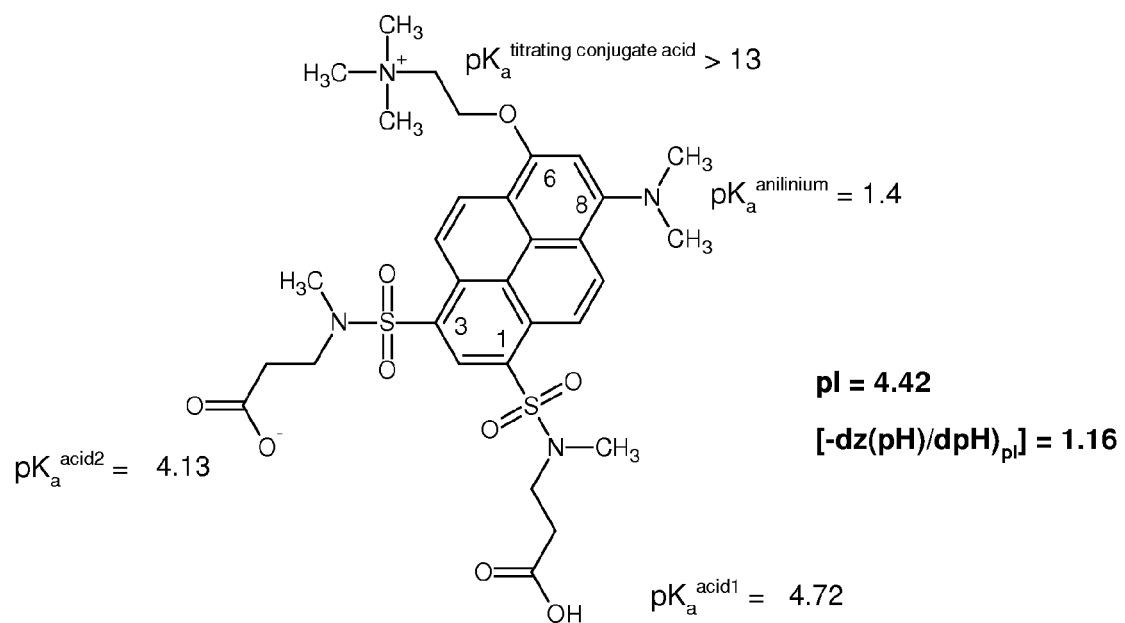
FIG. 2 illustrates a representative pI marker of the invention.
Figure 3:
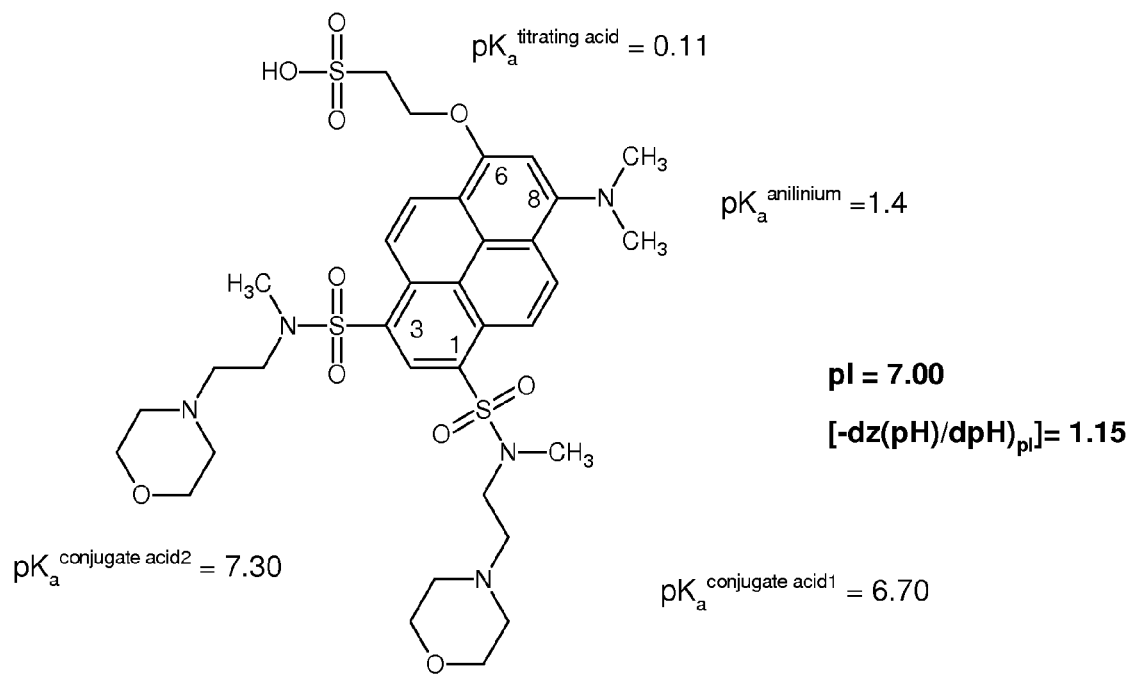
FIG. 3 illustrates a representative pI marker of the invention.

In the simplest cases, for aryl-bis(monoprotic sulfonamide) ampholytes, two general constructs are possible:

(a) $R_1$ or $R_2$ on each sulfonamido group carries a single acidic group (providing the ampholyte with two acidic groups having, respectively, $pK_a^{acid1}$ and $pK_a^{acid2}$ with $pK_a^{anilinium}<pK_a^{acid1}<pK_a^{acid2}$) while any one of R, $R_4$ and $R_5$ carries a single basic group (providing the ampholyte with a single basic group having for the conjugate acid form of the base $pK_a^{titrating\ conjugate\ acid}$ with $pK_a^{acid2}<pK_a^{titrating\ conjugate\ acid}$), setting the pI between $pK_a^{acid1}$ and $pK_a^{acid2}$ (FIG. 2); and (b) $R_1$ or $R_2$ on each sulfonamido group carries a single basic group (providing the ampholyte with two basic groups having, respectively, for the conjugate acid forms of the bases $pK_a^{conjugate\ acid1}$ and $pK_a^{conjugate\ acid2}$ with $pK_a^{anilinium}<pK_a^{conjugate\ acid1}<pK_a^{conjugate\ acid2}$), while any one of R, $R_4$ and $R_5$ carries a single acidic group (providing the ampholyte with one acidic group having $pK_a^{titrating\ acid}$ with $pK_a^{anilinium}<pK_a^{additional\ acid}<pK_a^{conjugate\ acids}$) setting the pI between $pK_a^{conjugate\ acid1}$ and $pK_a^{conjugate\ acid2}$ (FIG. 3).

Class (II) Ampholytes: aryl-bis(diprotic sulfonamide) Ampholytes

Figure 4:
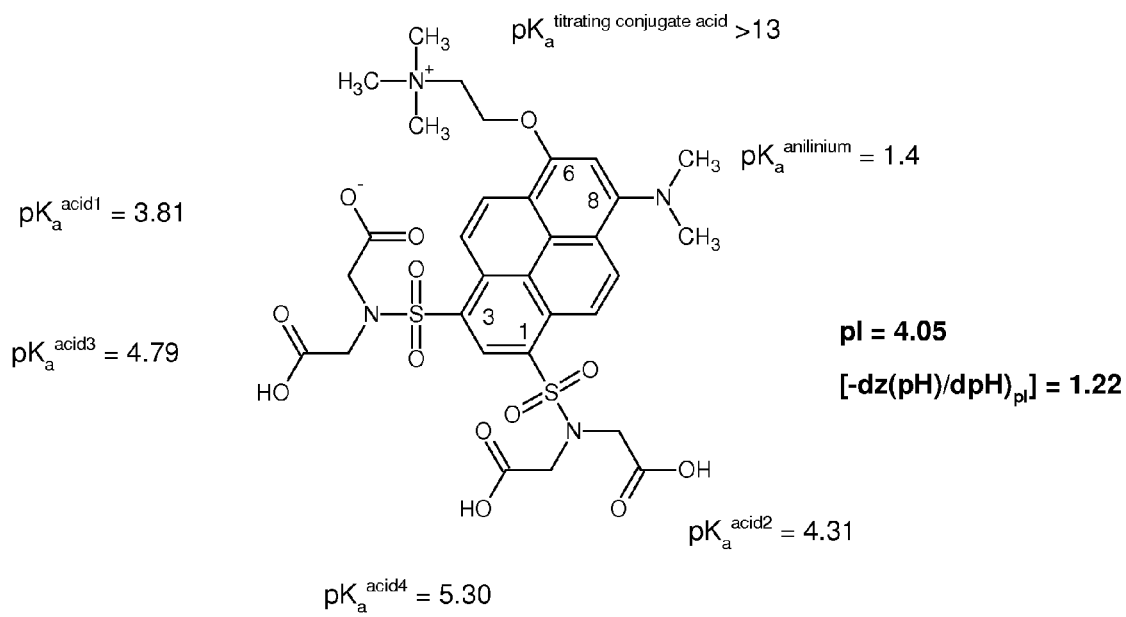
FIG. 4 illustrates a representative pI marker of the invention.
Figure 5:
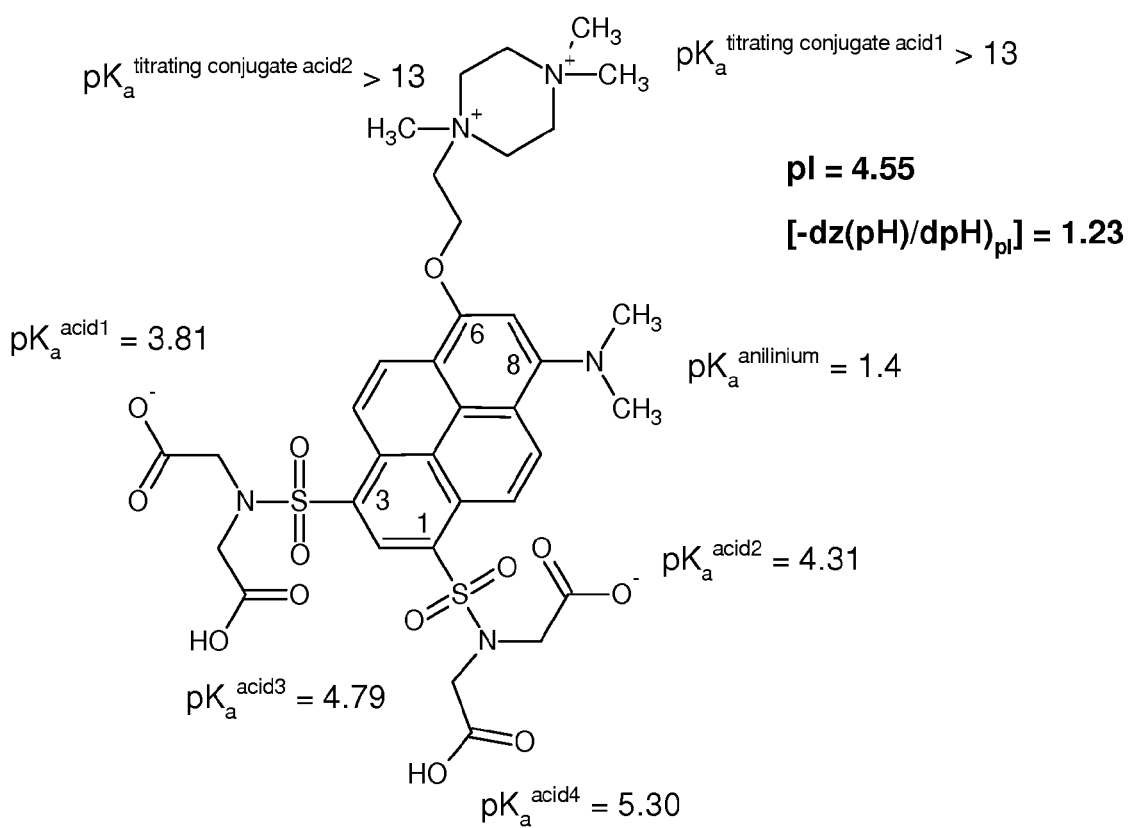
FIG. 5 illustrates a representative pI marker of the invention.
Figure 6:
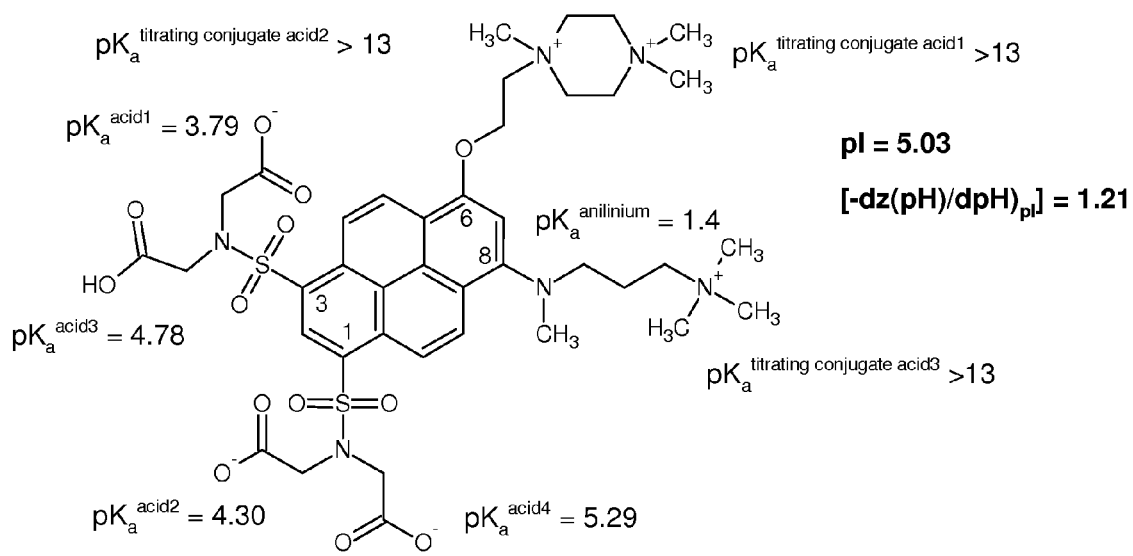
FIG. 6 illustrates a representative pI marker of the invention.
Figure 7:
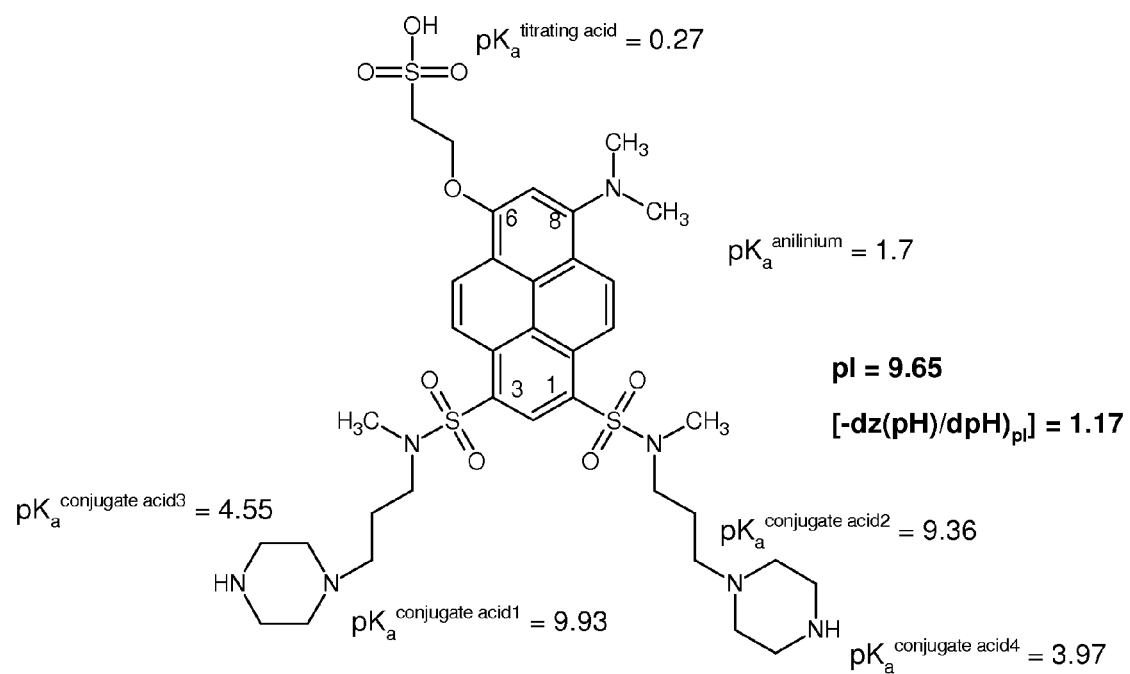
FIG. 7 illustrates a representative pI marker of the invention.
Figure 8:
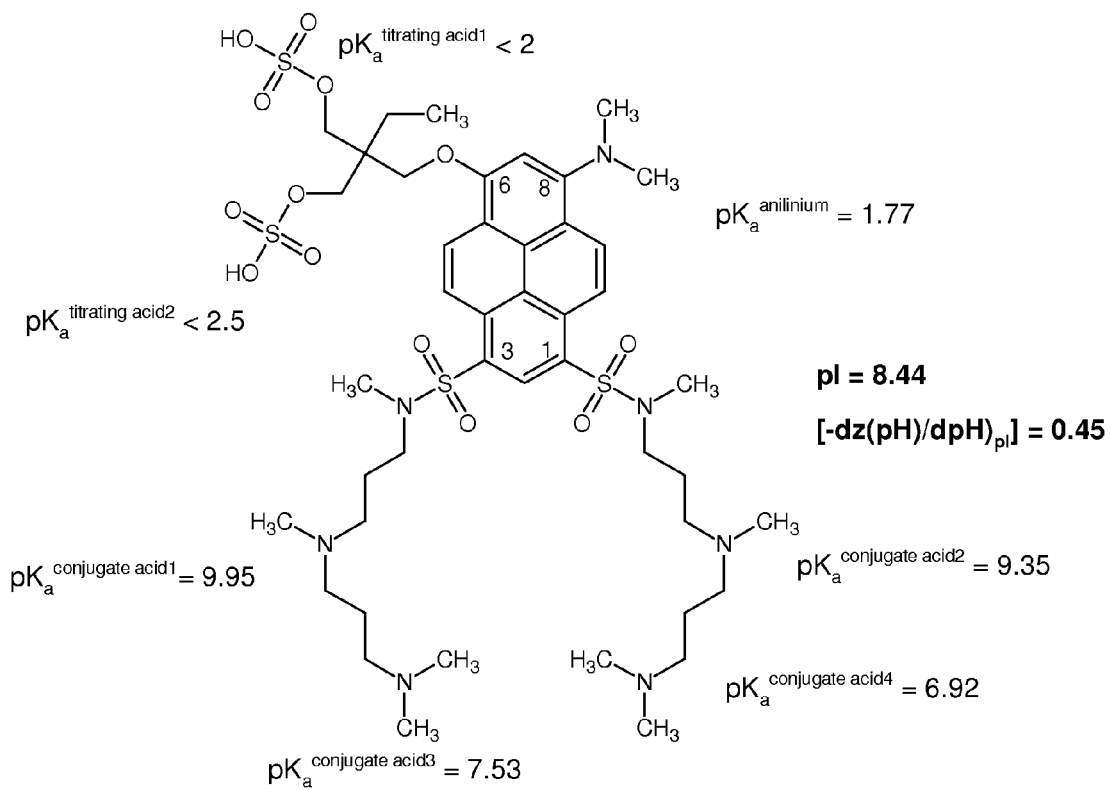
FIG. 8 illustrates a representative pI marker of the invention.
Figure 9:
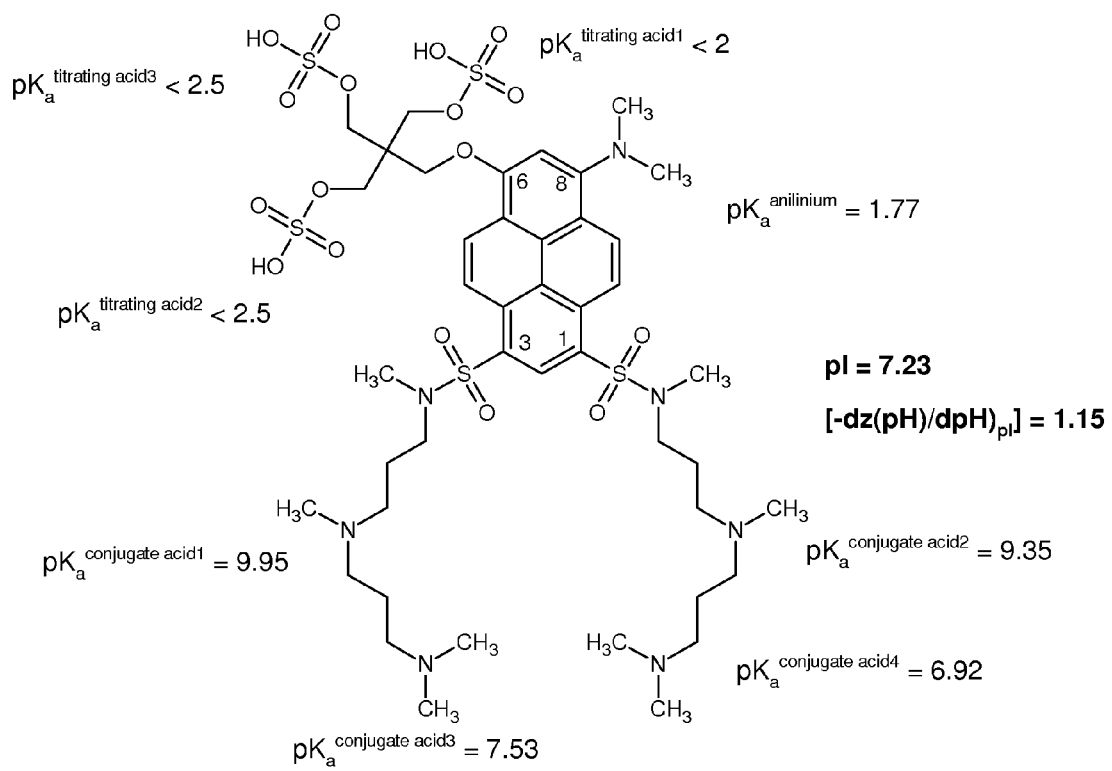
FIG. 9 illustrates a representative pI marker of the invention.
Figure 12:
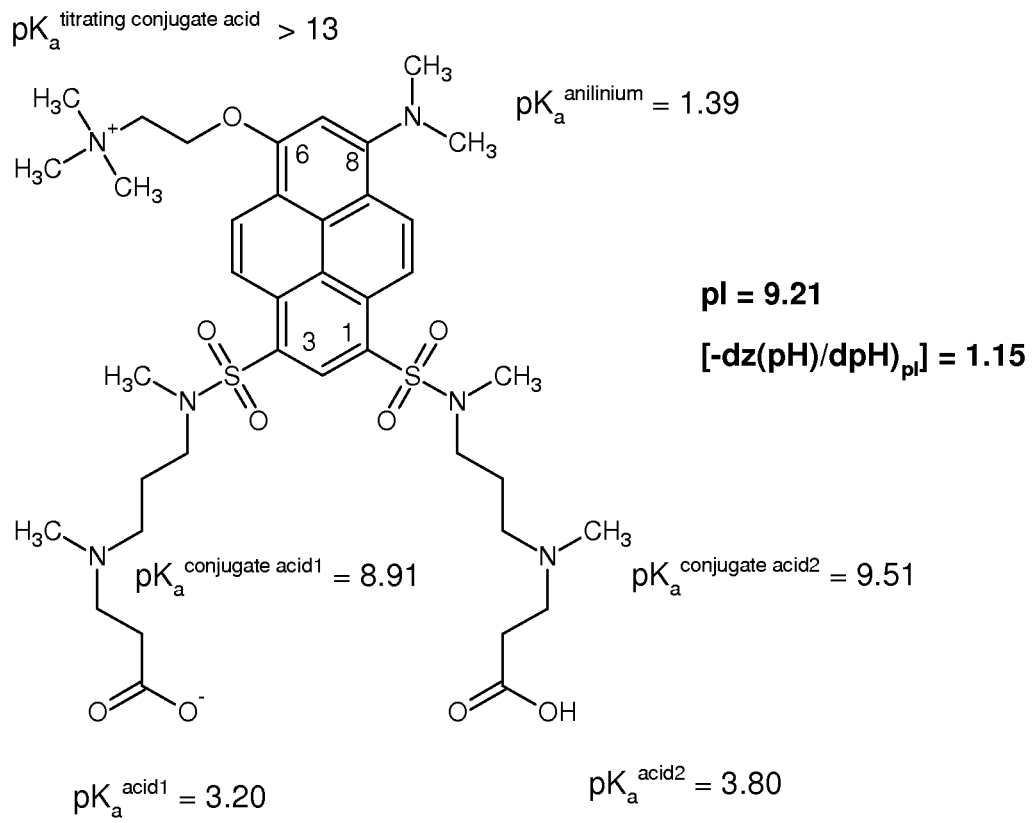
FIG. 12 illustrates a representative pI marker of the invention.

In the next simplest case, for aryl-bis(diprotic sulfonamide) type ampholytes, several general constructs are possible:

(a) $R_1$ or $R_2$ on each sulfonamido group carries two acidic groups (providing the ampholyte with four acidic groups having $pK_a^{acid1}$, $pK_a^{acid2}$, $pK_a^{acid3}$, and $pK_a^{acid4}$ with $pK_a^{anilinium}<pK_a^{acid1}<pK_a^{acid2}<pK_a^{acid3}<pK_a^{acid4}$), while one of R, $R_4$ or $R_5$ carries a single basic group (providing the ampholyte with one basic group having for the conjugate acid form of the base $pK_a^{titrating\ conjugate\ acid}$ with $pK_a^{acid2}<pK_a^{titrating\ conjugate\ acid}$), setting the pI between $pK_a^{acid1}$ and $pK_a^{acid2}$ (FIG. 4);

(b) $R_1$ or $R_2$ on each sulfonamido group carries two acidic groups (providing the ampholyte with four acidic groups having $pK_a^{acid1}$, $pK_a^{acid2}$, $pK_a^{acid3}$, and $pK_a^{acid4}$ with $pK_a^{anilinium}<pK_a^{acid1}<pK_a^{acid2}<pK_a^{acid3}<pK_a^{acid4}$), while one or two of R, $R_4$ and $R_5$ in combination carry two basic groups (providing the ampholyte with two additional basic groups having for the conjugate acid forms of the bases $pK_a^{titrating\ conjugate\ acid1}$ and $pK_a^{titrating\ conjugate\ acid2}$ with $pK_a^{titrating\ conjugate\ acid1}<pK_a^{titrating\ conjugate\ acid2}$ and with $pK_a^{acid3}<pK_a^{titrating\ conjugate\ acids}$) setting the pI between $pK_a^{acid2}+pK_a^{acid3}$ (FIG. 5);

(c) $R_1$ or $R_2$ on each sulfonamido group carries two acidic groups (providing the ampholyte with four acidic groups having $pK_a^{acid1}$, $pK_a^{acid2}$, $pK_a^{acid3}$, and $pK_a^{acid4}$ with $pK_a^{anilinium}<pK_a^{acid1}<pK_a^{acid2}<pK_a^{acid3}<pK_a^{acid4}$), while one, two or three of R, $R_4$ and $R_5$ in combination carry three basic groups (providing the ampholyte with three basic groups having for the conjugate acid forms of the bases $pK_a^{titrating\ conjugate\ acid1}$, $pK_a^{titrating\ conjugate\ acid2}$, and $pK_a^{titrating\ conjugate\ acid3}$ with $pK_a^{titrating\ conjugate\ acid1}<pK_a^{titrating\ conjugate\ acid2}<pK_a^{titrating\ conjugate\ acid3}$ and with $pK_a^{acid4}<pK_a^{titrating\ conjugate\ acid1}$) setting the pI between $pK_a^{acid3}$ and $pK_a^{acid4}$ (FIG. 6);

(d) $R_1$ or $R_2$ on each sulfonamido group carries two basic groups (providing the ampholyte with four basic groups having for the conjugate acid forms of the bases $pK_a^{conjugate\ acid1}$, $pK_a^{conjugate\ acid2}$, $pK_a^{conjugate\ acid3}$, and $pK_a^{conjugate\ acid4}$ with $pK_a^{anilinium}<pK_a^{conjugate\ acid1}<pK_a^{conjugate\ acid2}<pK_a^{conjugate\ acid3}<pK_a^{conjugate\ acid4}$) while any one of R, $R_4$ and $R_5$ carries a single acidic group (providing the ampholyte with an acidic group having $pK_a^{titrating\ acid}$ with $pK_a^{titrating\ acid}<pK_a^{conjugate\ acid3}$) setting the pI between $pK_a^{conjugate\ acid3}+pK_a^{conjugate\ acid4}$ (FIG. 7);

(e) $R_1$ or $R_2$ on each sulfonamido group carries two basic groups (providing the ampholyte with four basic groups having for the conjugate acid forms of the bases $pK_a^{conjugate\ acid1}$, $pK_a^{conjugate\ acid2}$, $pK_a^{conjugate\ acid3}$, and $pK_a^{conjugate\ acid4}$ with $pK_a^{anilinium}<pK_a^{conjugate\ acid1}<pK_a^{conjugate\ acid2}<pK_a^{conjugate\ acid3}<pK_a^{conjugate\ acid4}$) while one or two of R, $R_4$ and $R_5$ in combination carry two acidic groups (providing the ampholyte with two acidic groups having $pK_a^{titrating\ acid1}$ and $pK_a^{titrating\ acid2}$ with $pK_a^{titrating\ acid1}<pK_a^{titrating\ acid2}<pK_a^{conjugate\ acid3}$) setting the pI between $pK_a^{conjugate\ acid2}$ and $pK_a^{conjugate\ acid3}$ (FIG. 8);

(f) $R_1$ or $R_2$ on each sulfonamido group carries two basic groups (providing the ampholyte with four basic groups having for the conjugate acid forms of the bases $pK_a^{conjugate\ acid1}$, $pK_a^{conjugate\ acid2}$, $pK_a^{conjugate\ acid3}$, and $pK_a^{conjugate\ acid4}$ with $pK_a^{anilinium}<pK_a^{conjugate\ acid1}<pK_a^{conjugate\ acid2}<pK_a^{conjugate\ acid3}<pK_a^{conjugate\ acid4}$) while one or two or three of R, $R_4$ and $R_5$ in combination carry a total of three acidic groups (providing the ampholyte with three acidic groups having $pK_a^{titrating\ acid1}$, $pK_a^{titrating\ acid2}$, and $pK_a^{titrating\ acid3}$ with $pK_a^{titrating\ acid1}<pK_a^{titrating\ acid2}<pK_a^{titrating\ acid3}<pK_a^{conjugate\ acid4}$) setting the pI between $pK_a^{conjugate\ acid1}$ and $pK_a^{conjugate\ acid2}$ (FIG. 9);

(g) $R_1$ or $R_2$ on each sulfonamido group carry one acidic group and one basic group (providing the ampholyte with two acidic groups having $pK_a^{acid1}$ and $pK_a^{acid2}$ with $pK_a^{anilinium} < pK_a^{acid1} < pK_a^{acid2}$ and also providing the ampholyte with two basic groups having for the conjugate acid forms of the bases $pK_a^{conjugate\ acid1}$ and $pK_a^{conjugate\ acid2}$ with $pK_a^{conjugate\ acid1} < pK_a^{conjugate\ acid2}$ and with $pK_a^{acid2} < pK_a^{conjugate\ acid1}$), while all of R, $R_4$ or $R_5$ carry noncharged groups, setting the pI between $pK_a^{acid2}$ and $pK_a^{conjugate\ acid1}$ (FIG. 10);

(h) $R_1$ or $R_2$ on each sulfonamido group carry one acidic group and one basic group (providing the ampholyte with two acidic groups having $pK_a^{acid1}$ and $pK_a^{acid2}$ with $pK_a^{anilinium} < pK_a^{acid1} < pK_a^{acid2}$ and also providing the ampholyte with two basic groups having for the conjugate acid forms of the bases $pK_a^{conjugate\ acid1}$ and $pK_a^{conjugate\ acid2}$ with $pK_a^{conjugate\ acid1} < pK_a^{conjugate\ acid2}$ and with $pK_a^{acid2} < pK_a^{conjugate\ acid1}$), while one of R, $R_4$ and $R_5$ carries a single acidic group (providing the ampholyte with a third acidic group having $pK_a^{acid}$ with $pK_a^{acid} < pK_a^{acid1}$), setting the pI between $pK_a^{acid1}$ and $pK_a^{acid2}$ (FIG. 11); and (i) $R_1$ or $R_2$ on each sulfonamido group carry one acidic group and one basic group (providing the ampholyte with two acidic groups having $pK_a^{acid1}$ and $pK_a^{acid2}$ with $pK_a^{anilinium} < pK_a^{acid1} < pK_a^{acid2}$ and also providing the ampholyte with two basic groups having for the conjugate acid forms of the bases $pK_a^{conjugate\ acid1}$ and $pK_a^{conjugate\ acid2}$ with $pK_a^{conjugate\ acid1} < pK_a^{conjugate\ acid2}$ and with $pK_a^{acid2} < pK_a^{conjugate\ acid1}$), while one of R, $R_4$ and $R_5$ carries a basic group (providing the ampholyte with a third basic group having for the conjugate acid form of the base $pK_a^{titrating\ conjugate\ acid}$ with $pK_a^{conjugate\ acid1} < pK_a^{titrating\ conjugate\ acid}$), setting the pI between $pK_a^{conjugate\ acid1}$ and $pK_a^{conjugate\ acid2}$ (FIG. 12).

Class (III) Ampholytes: aryl-bis(triprotic sulfonamide) Ampholytes

Figure 13:
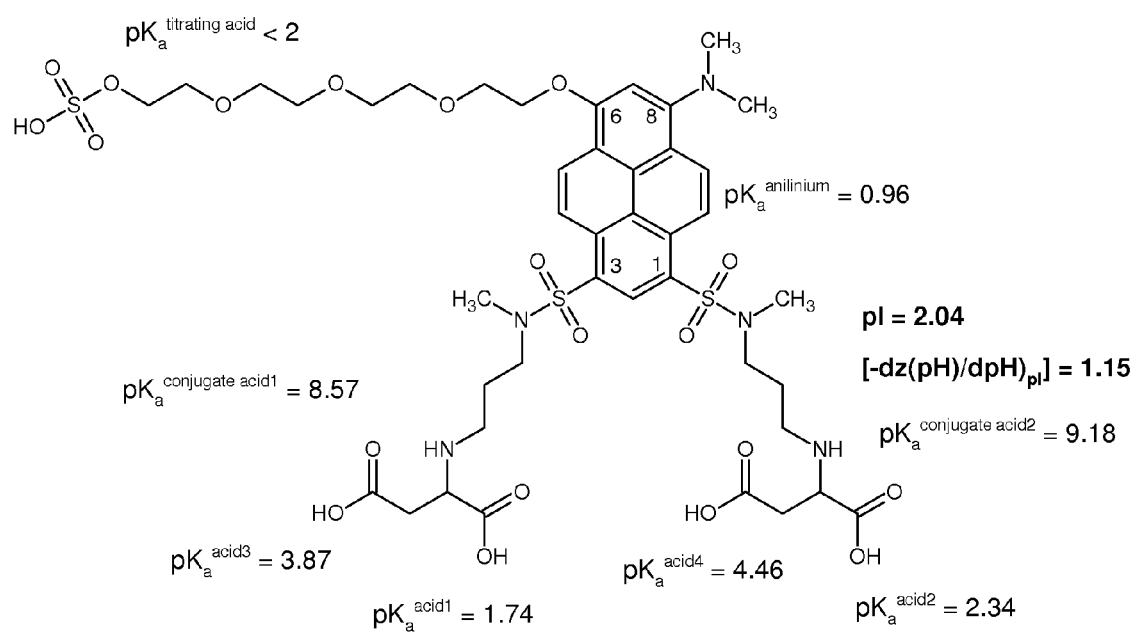
FIG. 13 illustrates a representative pI marker of the invention.
Figure 15:
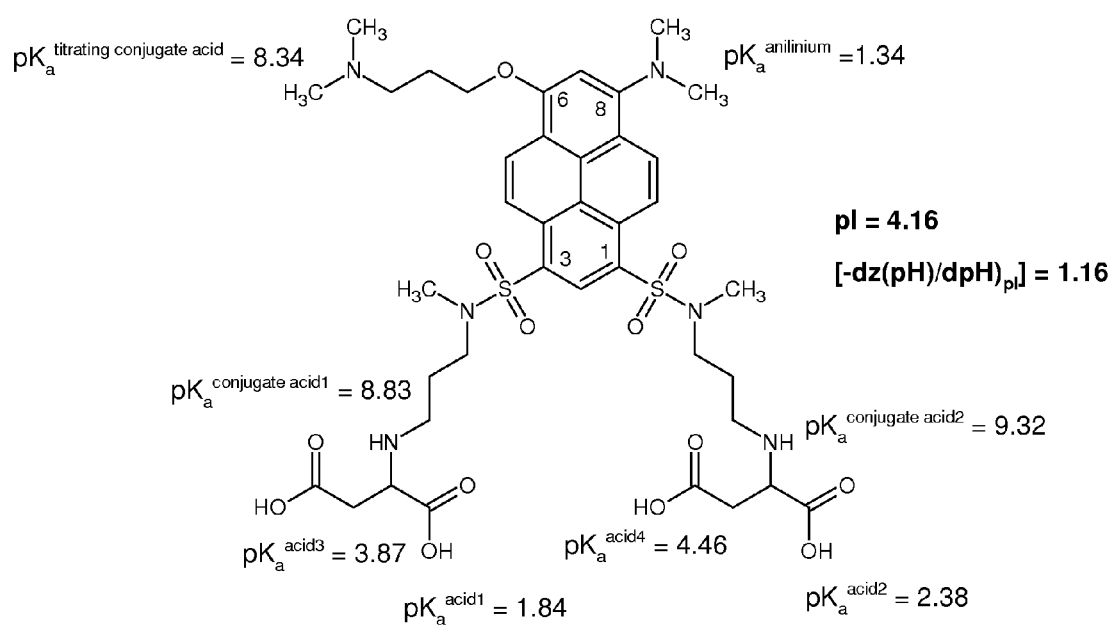
FIG. 15 illustrates a representative pI marker of the invention.
Figure 16:
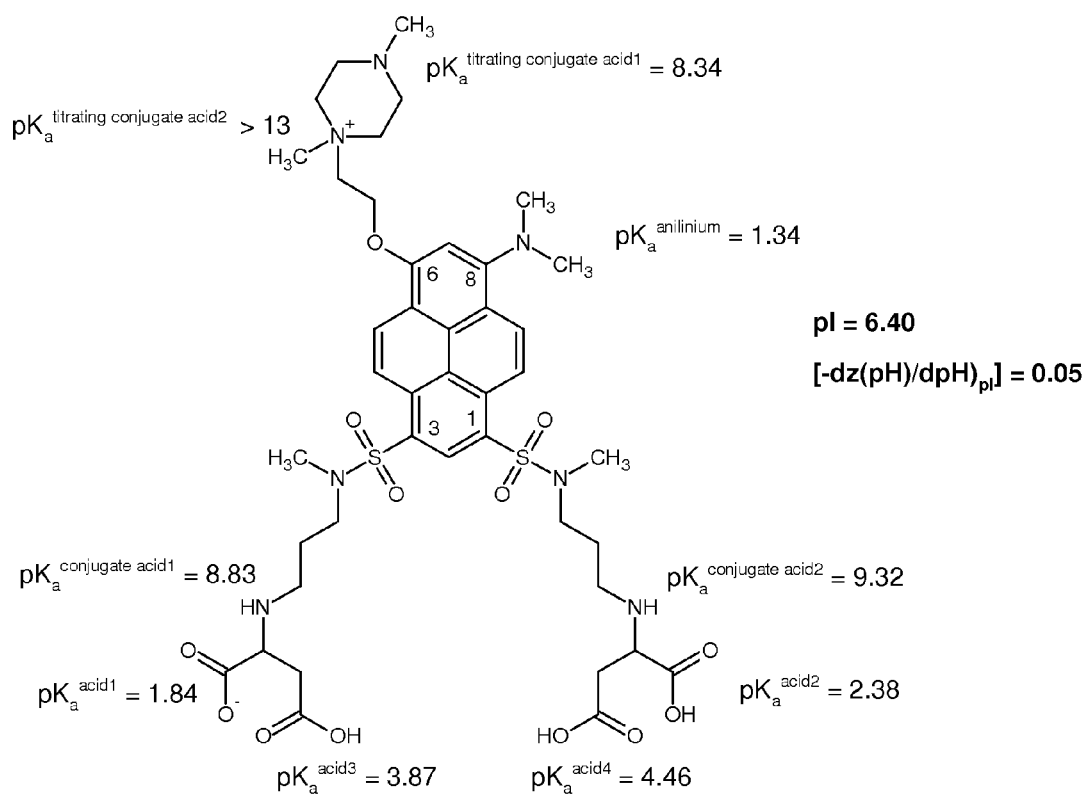
FIG. 16 illustrates a representative pI marker of the invention.
Figure 17:
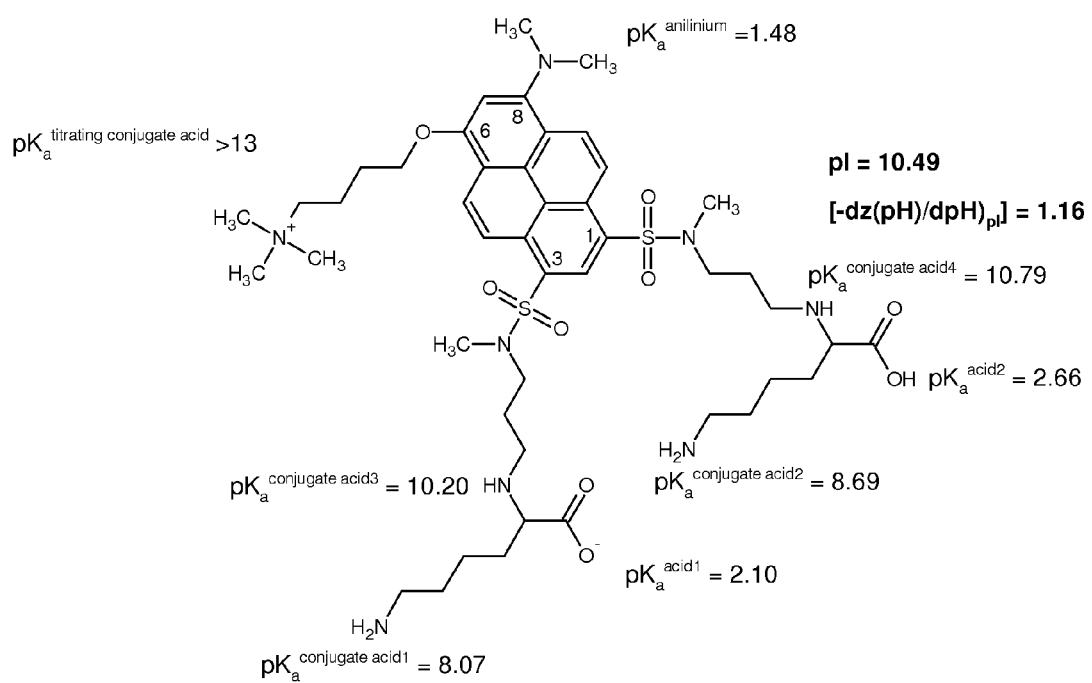
FIG. 17 illustrates a representative pI marker of the invention.
Figure 20:
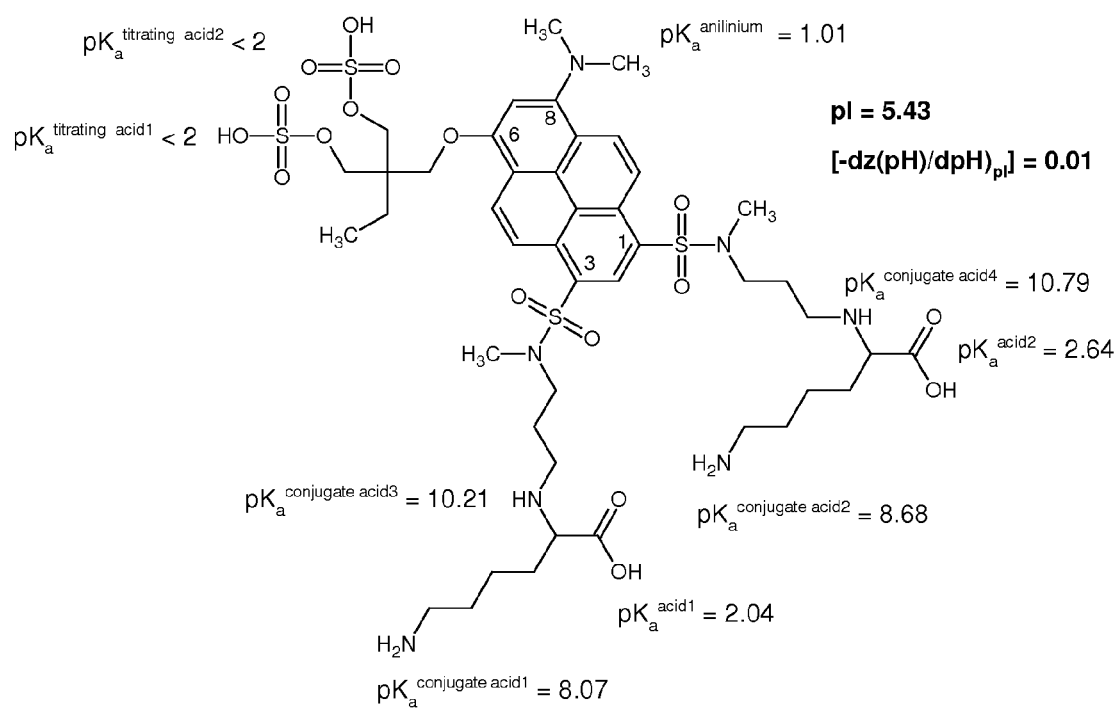
FIG. 20 illustrates a representative pI marker of the invention.

In an even more complex case, for aryl-bis(triprotic sulfonamide) type ampholytes, several general constructs are also possible:

(a) $R_1$ or $R_2$ on each sulfonamido group carries two acidic groups (providing the ampholyte with four acidic groups having $pK_a^{acid1}$, $pK_a^{acid2}$, $pK_a^{acid3}$, and $pK_a^{acid4}$ with $pK_a^{anilinium} < pK_a^{acid1} < pK_a^{acid2} < pK_a^{acid3} < pK_a^{acid4}$) and one basic group (also providing the ampholyte with two basic groups having for the conjugate acid forms of the base $pK_a^{conjugate\ acid1}$ and $pK_a^{conjugate\ acid2}$, with $pK_a^{acid4} < pK_a^{conjugate\ acid1}$ and $pK_a^{acid4} < pK_a^{conjugate\ acid2}$), while one of R, $R_4$ and $R_5$ carries one additional acidic group (having $pK_a^{titrating\ acid}$ with $pK_a^{titrating\ acid} < pK_a^{acid1}$), setting the pI between $pK_a^{acid1} + pK_a^{acid2}$ (FIG. 13);

(b) $R_1$ or $R_2$ on each sulfonamido group carries two acidic groups (providing the ampholyte with four acidic groups having $pK_a^{acid1}$, $pK_a^{acid2}$, $pK_a^{acid3}$, and $pK_a^{acid4}$ with $pK_a^{anilinium} < pK_a^{acid1} < pK_a^{acid2} < pK_a^{acid3} < pK_a^{acid4}$) and one basic group (also providing the ampholyte with two basic groups having for the conjugate acid forms of the base $pK_a^{conjugate\ acid1}$ and $pK_a^{conjugate\ acid2}$, with $pK_a^{acid4} < pK_a^{conjugate\ acid1} < pK_a^{conjugate\ acid2}$, while all of R, $R_4$ and $R_5$ carry noncharged groups, setting the pI between $pK_a^{acid2}$ and $pK_a^{acid3}$ (FIG. 14);

(c) $R_1$ or $R_2$ on each sulfonamido group carries two acidic groups (providing the ampholyte with four acidic groups having for the acids $pK_a^{acid1}$, $pK_a^{acid2}$, $pK_a^{acid3}$, and $pK_a^{acid4}$ with $pK_a^{anilinium} < pK_a^{acid1} < pK_a^{acid2} < pK_a^{acid3} < pK_a^{acid4}$) and one basic group (also providing the ampholyte with two basic groups having for the conjugate acid forms of the base $pK_a^{conjugate\ acid1}$ and $pK_a^{conjugate\ acid2}$, with $pK_a^{acid4} < pK_a^{conjugate\ acid1} < pK_a^{conjugate\ acid2}$), while one of R, $R_4$ and $R_5$ carries one additional basic group (providing the ampholyte with a third basic group having for the conjugate acid form of the base $pK_a^{titrating\ conjugate\ acid}$ with $pK_a^{acid4} < pK_a^{titrating\ conjugate\ acid}$), setting the pI between $pK_a^{acid3}$ and $pK_a^{acid4}$ (FIG. 15);

(d) $R_1$ or $R_2$ on each sulfonamido group carries two acidic groups (providing the ampholyte with four acidic groups having for the acids $pK_a^{acid1}$, $pK_a^{acid2}$, $pK_a^{acid3}$, and $pK_a^{acid4}$ with $pK_a^{anilinium} < pK_a^{acid1} < pK_a^{acid2} < pK_a^{acid3} < pK_a^{acid4}$) and one basic group (also providing the ampholyte with two basic groups having for the conjugate acid forms of the base $pK_a^{conjugate\ acid1}$ and $pK_a^{conjugate\ acid2}$, with $pK_a^{acid4} < pK_a^{conjugate\ acid1} < pK_a^{conjugate\ acid2}$), while one or two of R, $R_4$ and $R_5$ in combination carry a total of two additional basic groups (providing the ampholyte with a third and fourth basic group having for the conjugate acid forms of the bases $pK_a^{titrating\ conjugate\ acid1}$ and $pK_a^{titrating\ conjugate\ acid2}$ with $pK_a^{titrating\ conjugate\ acid1} < pK_a^{titrating\ conjugate\ acid2}$ and with $pK_a^{acid4} < pK_a^{conjugate\ acid\ smallest}$ where $pK_a^{conjugate\ acid\ smallest}$ is defined as the smallest of $pK_a^{conjugate\ acid1}$, $pK_a^{conjugate\ acid2}$, $pK_a^{titrating\ conjugate\ acid1}$ and $pK_a^{titrating\ conjugate\ acid2}$, setting the pI between $pK_a^{acid4}$ and $pK_a^{conjugate\ acid\ smallest}$ (FIG. 16);

(e) $R_1$ or $R_2$ on each sulfonamido group carries two basic groups (providing the ampholyte with four basic groups having for the conjugate acid forms of the bases $pK_a^{conjugate\ acid1}$, $pK_a^{conjugate\ acid2}$, $pK_a^{conjugate\ acid3}$, and $pK_a^{conjugate\ acid4}$ with $pK_a^{anilinium} < pK_a^{conjugate\ acid1} < pK_a^{conjugate\ acid2} < pK_a^{conjugate\ acid3} < pK_a^{conjugate\ acid4}$) and one acidic group (also providing the ampholyte with two acidic groups having $pK_a^{acid1}$ and $pK_a^{acid2}$, with $pK_a^{acid1} < pK_a^{acid2} < pK_a^{conjugate\ acid1}$), while one of R, $R_4$ and $R_5$ carries a single basic group (having for the conjugate acid form of the base $pK_a^{titrating\ conjugate\ acid}$ with $pK_a^{conjugate\ acid4} < pK_a^{titrating\ conjugate\ acid}$), setting the pI between $pK_a^{conjugate\ acid3}$ and $pK_a^{conjugate\ acid4}$ (FIG. 17);

$R_1$ or $R_2$ on each sulfonamido group carries two basic groups (providing the ampholyte with four basic groups having for the conjugate acid forms of the bases $pK_a^{conjugate\ acid1}$, $pK_a^{conjugate\ acid2}$, $pK_a^{conjugate\ acid3}$, and $pK_a^{conjugate\ acid4}$ with $pK_a^{anilinium} < pK_a^{conjugate\ acid1} < pK_a^{conjugate\ acid2} < pK_a^{conjugate\ acid3} < pK_a^{conjugate\ acid4}$) and one acidic group (also providing the ampholyte with two acidic groups having $pK_a^{acid1}$ and $pK_a^{acid2}$ with $pK_a^{anilinium} < pK_a^{acid1} < pK_a^{acid2}$ and with $pK_a^{acid2} < pK_a^{conjugate\ acid1}$), while all of R, $R_4$ and $R_5$ carry noncharged groups, setting the pI between $pK_a^{conjugate\ acid2}$ and $pK_a^{conjugate\ acid3}$ (FIG. 18);

(g) $R_1$ or $R_2$ on each sulfonamido group carries two basic groups (providing the ampholyte with four basic groups having for the conjugate acid forms of the bases $pK_a^{conjugate\ acid1}$, $pK_a^{conjugate\ acid2}$, $pK_a^{conjugate\ acid3}$, and $pK_a^{conjugate\ acid4}$ with $pK_a^{anilinium} < pK_a^{conjugate\ acid1} < pK_a^{conjugate\ acid2} < pK_a^{conjugate\ acid3} < pK_a^{conjugate\ acid4}$) and one acidic group (also providing the ampholyte with two acidic groups having $pK_a^{acid1}$ and $pK_a^{acid2}$ with $pK_a^{anilinium} < pK_a^{acid1} < pK_a^{acid2}$ and with $pK_a^{acid2} < pK_a^{conjugate\ acid1}$), while one of R, $R_4$ and $R_5$ carries one acidic group (providing the ampholyte with a third acidic group having $pK_a^{titrating\ acid}$ with $pK_a^{titrating\ acid} < pK_a^{conjugate\ acid1}$), setting the pI between $pK_a^{conjugate\ acid1}$ and $pK_a^{conjugate\ acid2}$ (FIG. 19); and (h) $R_1$ or $R_2$ on each sulfonamido group carries two basic groups (providing the ampholyte with four basic groups having for the conjugate acid forms of the bases $pK_a^{conjugate\ acid1}$, $pK_a^{conjugate\ acid2}$, $pK_a^{conjugate\ acid3}$, and $pK_a^{conjugate\ acid4}$ with $pK_a^{anilinium} < pK_a^{conjugate\ acid1} < pK_a^{conjugate\ acid2} < pK_a^{conjugate\ acid3} < pK_a^{conjugate\ acid4}$) and one acidic group (also providing the ampholyte with two acidic groups having $pK_a^{acid1}$ and $pK_a^{acid2}$ with $pK_a^{anilinium} < pK_a^{acid1} < pK_a^{acid2}$ and with $pK_a^{acid2} < pK_a^{conjugate\ acid1}$), while one or two of R, $R_4$ and $R_5$ in combination carry a total of two additional acidic groups (providing the ampholyte with a third and fourth acidic group having $pK_a^{titrating\ acid1}$ and $pK_a^{titrating\ acid2}$ with $pK_a^{titrating\ acid1} < pK_a^{titrating\ acid2}$ and with $pK_a^{acid\ highest} < pK_a^{conjugate\ acid1}$ where $pK_a^{acid\ highest}$ is defined as the largest of $pK_a^{acid1}$, $pK_a^{acid2}$, $pK_a^{titrating\ acid1}$ and $pK_a^{titrating\ acid2}$), setting the pI between $pK_a^{acid\ highest}$ and $pK_a^{conjugate\ acid1}$ (FIG. 20).

It can be seen from FIGS. 2 to 20, that the smallest $pK_a$ gap and the highest $[-dz(pH)/d(pH)_{pI}]$ values can be achieved (and the best focusing analyte be made), when the pI value lies between the $pK_a$ values that belong to the same type of protic group on the two sulfonamido groups, i.e., when the pI is between $pK_a^{acid1}$ and $pK_a^{acid2}$, or between $pK_a^{acid3}$ and $pK_a^{acid4}$ or between $pK_a^{conjugate\ acid1}$ and $pK_a^{conjugate\ acid2}$ or between $pK_a^{conjugate\ acid3}$ and $pK_a^{conjugate\ acid4}$. In these cases, unexpectedly, we were able to see $pK_a$ gaps smaller than 0.7 (compare with the $1 < \Delta pK_a < 4$ values cited in the literature referenced in the Introduction) and $[-dz(pH)/d(pH)_{pI}] > 1.2$ (compare with the <1 values cited in the literature referenced above). From a practical point of view, ampholytes having their pI between $pK_a^{acid3}$ and $pK_a^{acid4}$ or between $pK_a^{conjugate\ acid1}$ and $pK_a^{conjugate\ acid2}$ are especially desirable, because they are more water soluble due to the dissociation (protonation) of the first two (stronger) acidic (basic) groups.

The preparation of representative pI markers of the invention is described and illustrated schematically in FIGS. 21-26. The pI markers of the invention shown in FIG. 1 can be synthesized using opportunistic approaches (i.e., using synthetic schemes unique to particular ampholytes) when advantageous intermediates exist or they can be synthesized using streamlined approaches that rely on common intermediates.

Table 1 lists the calculated pI values and the $[-dz(pH)/d(pH)_{pI}]$ values for a few characteristic aryl-bis(monoprotic sulfonamide) ampholytes having structures similar to what is shown in FIG. 2 and having pI values that are in the pI<7 range. These ampholytes can be obtained using an opportunistic approach, starting with APTS, (i) chlorinating it, (ii) then reacting the chlorosulfonate with the methyl or ethyl esters of common monocarboxylic amino acids, (iii) if needed, methylating the sulfonamide groups to convert —SO$_2$NHR to —SO$_2$N(CH$_3$)R, (iv) simultaneously replacing one of the sulfonamide groups with a basic titrating group and hydrolyzing the esters, and (v) obtaining the ampholyte in isoelectric form by isoelectric precipitation or isoelectric trapping (Lalwani, S., Tutu, E., Vigh, G., *Electrophoresis* 26 (2005) 2503 and references therein, and Shave, E., Vigh, G., *Electrophoresis* 28 (2007) 587). They all have excellent $[-dz(pH)/d(pH)_{pI}]$ values (1.15); their pI values cover the 3.65<pI<4.65 range. Table 1 also indicates that outside this pI range, other, more complex ampholyte structures need to be considered.

TABLE 1

Ampholytes utilizing acidic monoprotic buffering moieties in the sulfonamido groups.

| | Titrating group derived from Choline | |
|---|---|---|
| Sulfonamide derived from | pI | −dz/dpH |
| 2-Hydroxy-4-aminobutyric acid | 3.65 | 1.16 |
| 3-Hydroxy-4-aminobutyric acid | 4.1 | 1.15 |
| Beta-alanine | 4.26 | 1.15 |
| 4-Aminobutyric acid | 4.53 | 1.15 |
| Alanine | 4.62 | 1.15 |
| Glycine | 4.65 | 1.15 |
| 5-Aminocaproic acid | 4.66 | 1.15 |

Table 2 lists the calculated pI values and the $[-dz(pH)/d(pH)_{pI}]$ values for a few characteristic aryl-bis(monoprotic sulfonamide) ampholytes having structures similar to what is shown in FIG. 3 and having pI values that are in the 7<pI range. They can be synthesized using the opportunistic approach as outlined above, except that the chlorosulfonate groups are reacted with diamines and the titrating group is derived from a hydroxy acid.

TABLE 2

Ampholytes utilizing basic monoprotic buffering moieties in the sulfonamido groups.

| | Titrating group derived from Isethionic acid | |
|---|---|---|
| Sulfonamide derived from | pI | −dz/dpH |
| Morpholine | 6.73 | 1.15 |
| TRIS | 7.78 | 1.15 |
| Diethanolamine | 8.23 | 1.15 |
| Dipropanolamine | 9.04 | 1.15 |
| Dimethylamine | 9.26 | 1.15 |
| Methylethylamine | 9.32 | 1.15 |
| Diethylamine | 9.39 | 1.15 |
| Propylamine | 9.59 | 1.15 |
| Ethanolamine | 9.63 | 1.15 |
| Methylamine | 10 | 1.15 |

Figure 21:
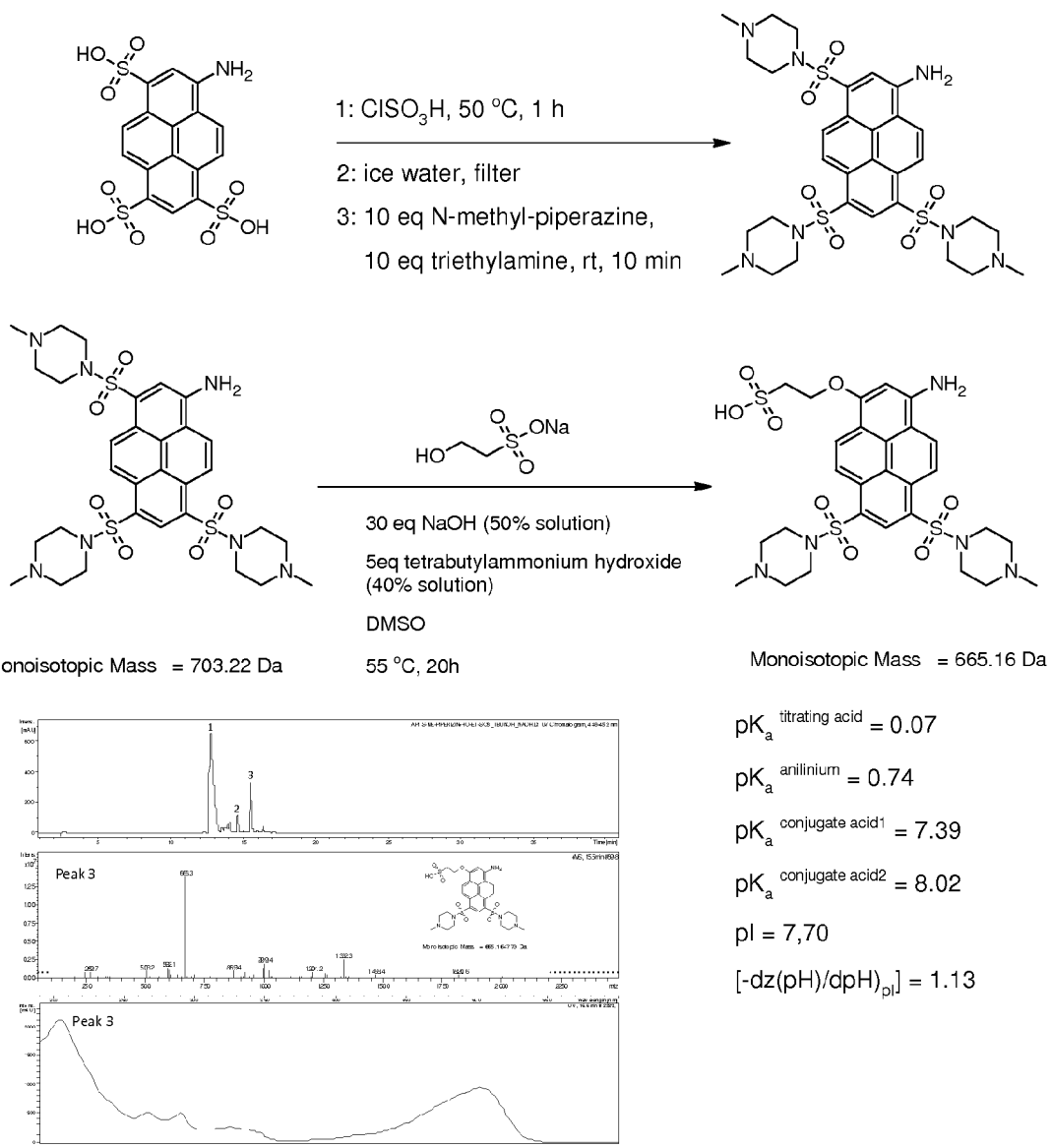
FIG. 21 illustrates the preparation of a representative pI marker of the invention.

FIG. 21 shows an example for the opportunistic preparation of a basic aryl-bis(monoprotic sulfonamide) ampholyte, the pI=7.70 ampholyte with $[-dz(pH)/d(pH)_{pI}]$=1.13 that is synthesized from 8-amino-1,3,6-pyrenetrisulfonic acid (APTS), trisodium salt (providing the core scaffold by treatment with chlorosulfonic acid), and N-methylpiperazine (providing the buffering weak electrolyte element of the sulfonamido groups) and isethionic acid (providing the acidic titrating group). An aliquot of the reaction mixture was taken during the reaction and analyzed by HPLC-ESI/MS (Phenomenex Gemini C18 column, gradient elution from 5:95 acetonitrile:water to 95:5 in 40 min, Agilent 6320 Iontrap LC/MS). The results are shown at the bottom of FIG. 21 confirming the expected molecular mass of the pI 7.70 marker and its light absorption maximum in the 480 to 510 nm (visible) range.

Figure 22:
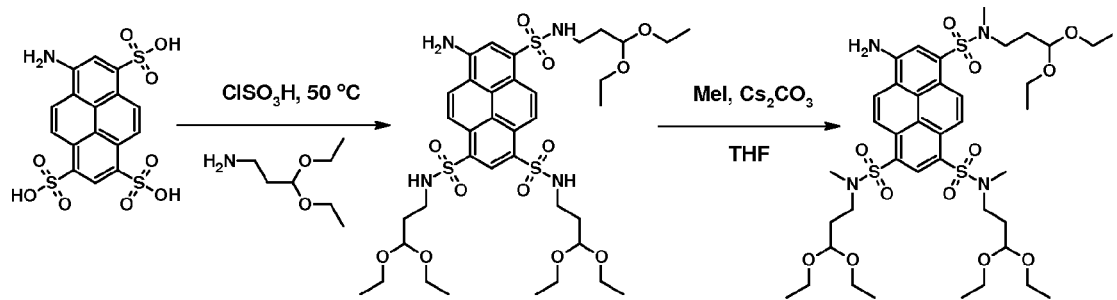
FIG. 22 illustrates the preparation of a representative pI marker of the invention.
Figure 22:
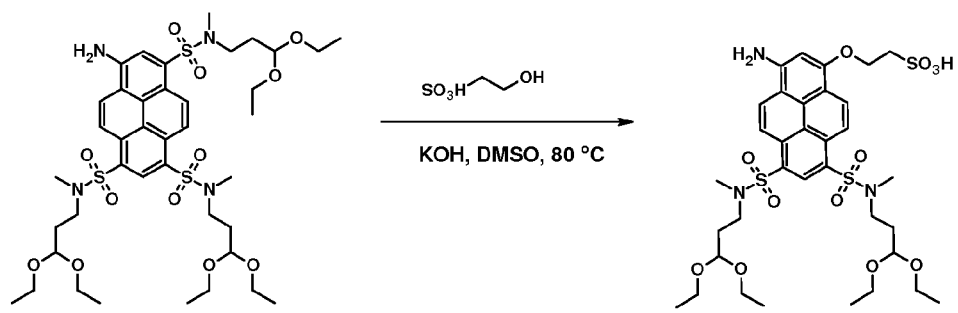
Figure 22:
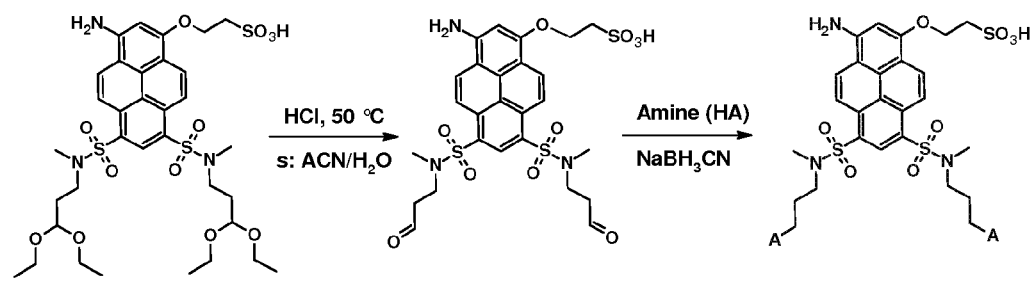
Figure 23:
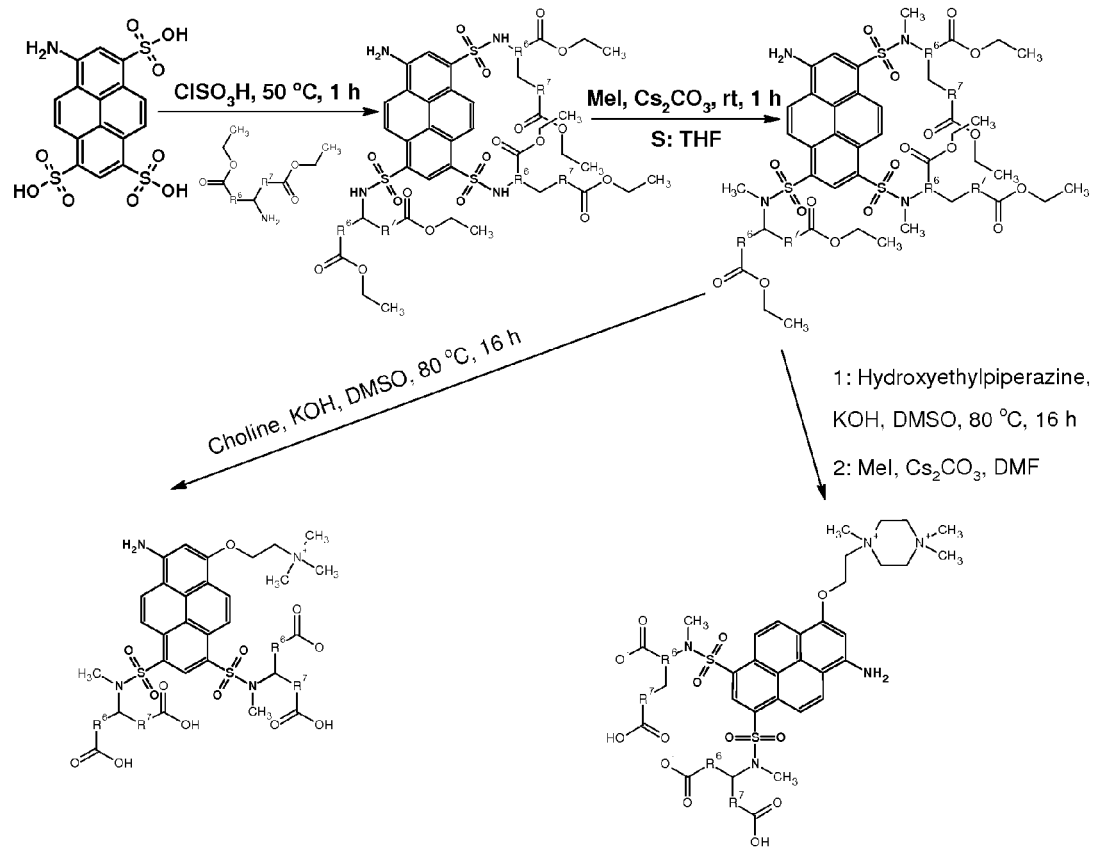
FIG. 23 illustrates the preparation of representative pI markers of the invention.

They can also be obtained using the 3-step streamlined approach according to FIG. 22, starting with APTS, (i) chlorinating it with chlorosulfonic acid, (ii) forming an aryl-tris(diethylacetal sulfonamide) intermediate, (iii) installing the titrating group (e.g., oxyethylsulfonic acid), (iv) forming the final active intermediate, aryl-bis(propionaldehyde sulfonamide), (v) reacting the active intermediate with different monoamines, and (vi) obtaining the ampholyte in an isoelectric form by isoelectric precipitation or isoelectric trapping. The ampholytes that can be obtained via this route all have excellent $[-dz(pH)/d(pH)_{pI}]$ values (1.15); their pI values fall in the 6.7<pI<10 range. Table 2 also indicates that outside this pI range, other, more complex ampholyte structures need to be considered.

Though the aryl-bis(diprotic sulfonamide) ampholytes can also be synthesized using opportunistic approaches, the streamlined synthetic scheme shown in FIG. 22 for the basic aryl-bis(monoprotic sulfonamide) ampholytes affords a more economical approach and provides for simplified quality control due to the use of the common intermediates. By varying $R^6$ and $R^7$ and the attachment position of $—NH_2$ along $R^6$ and $R^7$ in FIG. 23, many different $pK_a^{acid1}$ and $pK_a^{acid2}$ values can be accessed. For example, aminomalonic acid yields an ampholyte with pI=2.7, $[-dz(pH)/d(pH)_{pI}]$=1.15 with choline as the source of the basic titrating group and yields another ampholyte with pI=3.86, $[-dz(pH)/d(pH)_{pI}]$=0.5 with N,N-dimethyl-N'-methyl-N'-(2-hydroxyethyl)piperazinium as the source of the basic titrating group. Aspartic acid yields an ampholyte with pI=3.66 and $[-dz(pH)/d(pH)_{pI}]$=1.19 with choline as the base and another ampholyte with pI=4.27 and $[-dz(pH)/d(pH)_{pI}]$=1.10 with N,N-dimethyl-N'-methyl-N'-(2-hydroxyethyl)piperazinium as the base. Glutamic acid yields and ampholyte with pI=4.04 and $[-dz(pH)/d(pH)_{pI}]$=1.21 with choline as the base and another ampholyte with pI=4.53 and $[-dz(pH)/d(pH)_{pI}]$=1.23 with N,N-dimethyl-N'-methyl-N'-(2-hydroxyethyl)piperazinium as the base. Iminodiacetic acid yields an ampholyte with pI=4.06 and $[-dz(pH)/d(pH)_{pI}]$=1.22 with choline as the base and another ampholyte with pI=4.56 and $[-dz(pH)/d(pH)_{pI}]$=1.23 with N,N-dimethyl-N'-methyl-N'-(2-hydroxyethyl)piperazinium as the base. Iminodipropionic acid yields an ampholyte with pI=3.85 and $[-dz(pH)/d(pH)_{pI}]$=1.26 with choline as the base and another ampholyte with pI=4.26 and $[-dz(pH)/d(pH)_{pI}]$=1.30 with N,N-dimethyl-N'-methyl-N'-(2-hydroxyethyl)piperazinium as the base.

Representative ampholytes are set forth in Table 3.

TABLE 3

Representative ampholytes derived from amino acids.

| pI | -dz/dpH | Sulfonamide derived from | Titrant derived from |
|---|---|---|---|
| 2.7 | 1.15 | Aminomalonic acid | Choline |
| 3.66 | 1.19 | Aspartic acid | Choline |
| 3.85 | 1.26 | Iminodi(3-propionic acid) | Choline |
| 4.06 | 1.22 | Iminodiacetic acid | Choline |
| 4.26 | 1.3 | Iminodi(3-propionic acid) | N-(2-hydroxyethyl)-N,N',N'-trimethyl piperazine |
| 4.56 | 1.23 | Iminodiacetic acid | N-(2-hydroxyethyl)-N,N',N'-trimethyl piperazine |

Figure 24:
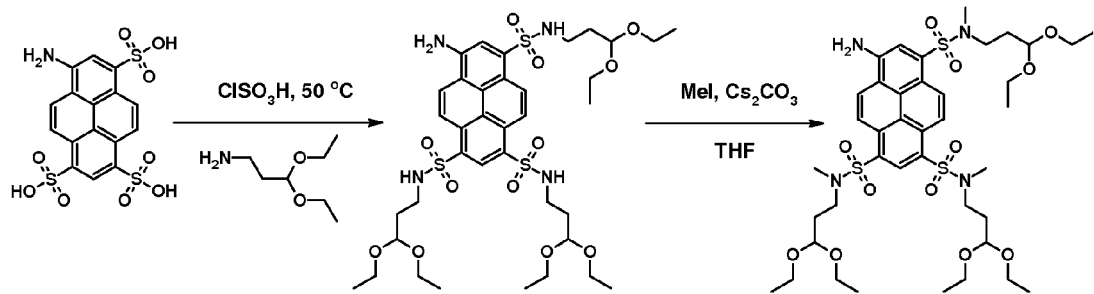
FIG. 24 illustrates the preparation of a representative pI marker of the invention.
Figure 24:
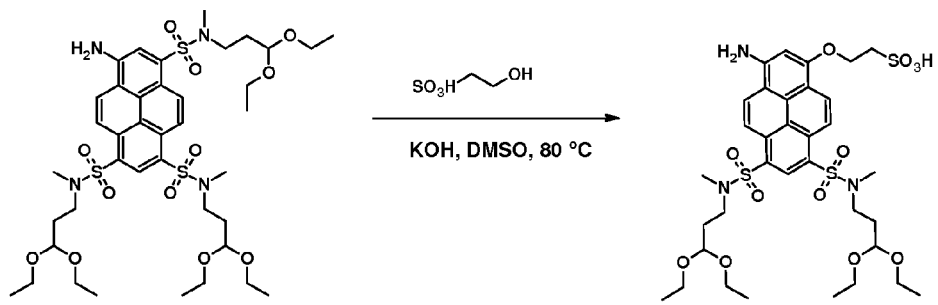
Figure 24:
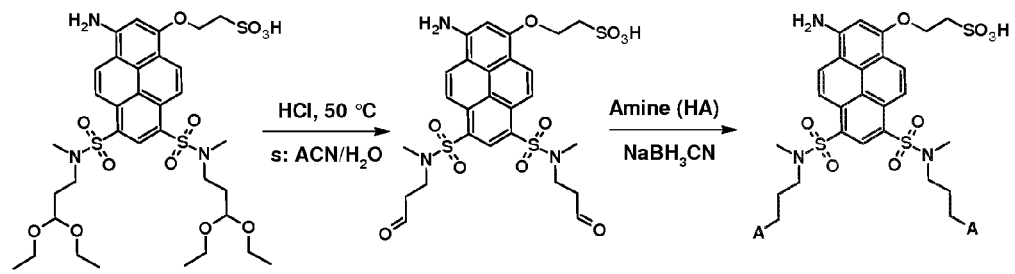

Table 4 shows representative ampholytes that can be made using various diamines as sources of the diprotic groups in the sulfonamide moieties according to the general scheme shown in FIG. 24.

TABLE 4

Representative ampholytes derived from diamines.

| pI | HA | Titrant derived from | -dz/dpH |
|---|---|---|---|
| 8.46 | (2-Hydroxyethyl)piperazine | Isethionic acid | 1.15 |
| 9.2 | N,N'-Bis(2-hydroxyethyl)ethylenediamine | Isethionic acid | 1.17 |
| 9.43 | N-Methyl-N',N'-dimethyl-ethylenediamine | Isethionic acid | 1.15 |

TABLE 4-continued

Representative ampholytes derived from diamines.

| pI | HA | Titrant derived from | -dz/dpH |
|---|---|---|---|
| 9.48 | N,N'-Bis(2-hydroxyethyl)ethylenediamine | Isethionic acid | 1.17 |
| 9.65 | Piperazine | Isethionic acid | 1.17 |
| 10.01 | N,N'-Dimethyl ethylenediamine | Isethionic acid | 1.15 |
| 10.02 | Ethylenediamine | Isethionic acid | 1.15 |
| 10.34 | Propylenediamine | Isethionic acid | 1.15 |

Figure 25:
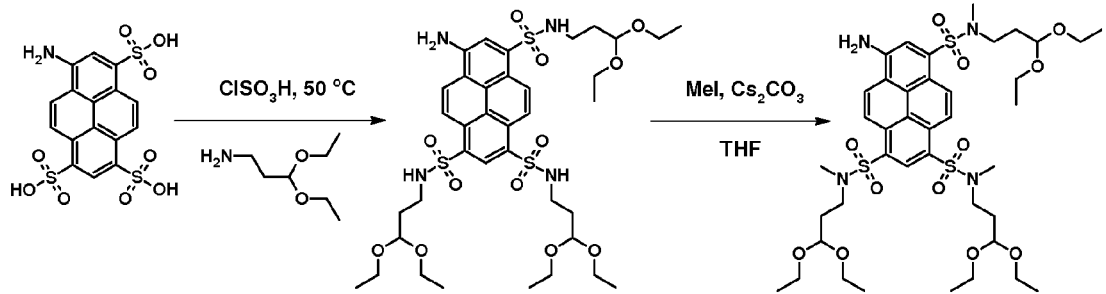
FIG. 25 illustrates the preparation of a representative pI marker of the invention.
Figure 25:
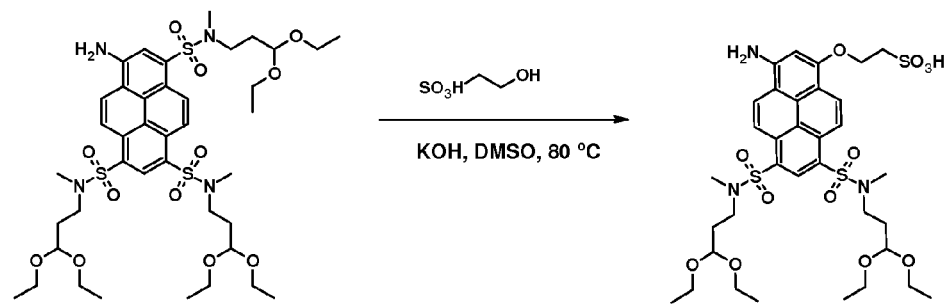
Figure 25:
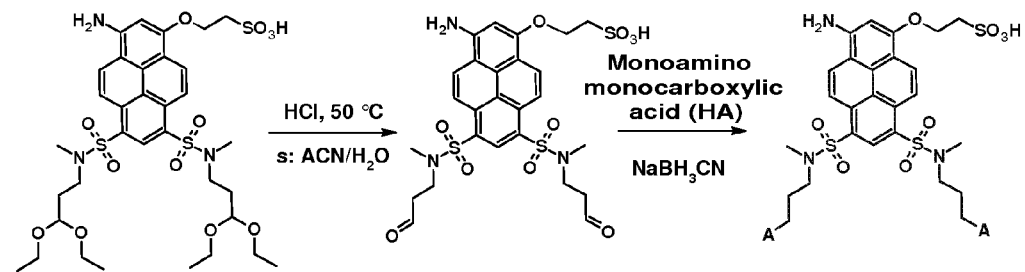

Table 5 shows representative ampholytes that can be made using various monoamino monocarboxylic acids as sources of the diprotic groups in the sulfonamido moieties according to the general scheme shown in FIG. 25.

TABLE 5

Representative ampholytes derived from monoamino monocarboxylic acids.

| pI | HA | Titrant derived from | -dz/dpH |
|---|---|---|---|
| 2.49 | Glycine | Isethionic acid | 1.14 |
| 3.39 | 2-Hydroxy-4-aminobutryic acid | Isethionic acid | 1.1 |
| 3.63 | Beta-alanine | Isethionic acid | 1.15 |
| 3.77 | 4-Aminobutyric acid | Isethionic acid | 1.17 |
| 4.32 | 5-Aminocaproic acid | Isethionic acid | 1.15 |
| 8.7 | Glycine | N,N-Dimethylpropanol | 1.2 |
| 8.89 | 5-Aminocaproic acid | N,N-Dimethylpropanol | 0.48 |
| 8.93 | Beta-alanine | N,N-Dimethylpropanol | 0.68 |
| 9.09 | Glycine | Choline | 1.1 |
| 9.13 | 3-Hydroxy-4-aminobutyric acid | N,N-Dimethylpropanol | 0.92 |
| 9.27 | 2-Hydroxy-4-aminobutryic acid | N,N-Dimethylpropanol | 0.36 |
| 9.31 | 4-Aminobutyric acid | N,N-Dimethylpropanol | 0.34 |
| 9.8 | 3-Hydroxy-4-aminobutryic acid | Choline | 1.09 |
| 10.05 | 5-Aminocaproic acid | Choline | 1.15 |
| 10.27 | Beta-alanine | Choline | 0.98 |
| 10.36 | 4-Aminobutyric acid | Choline | 1.05 |
| 10.87 | 2-Hydroxy-4-aminobutryic acid | Choline | 1.07 |

Figure 26:
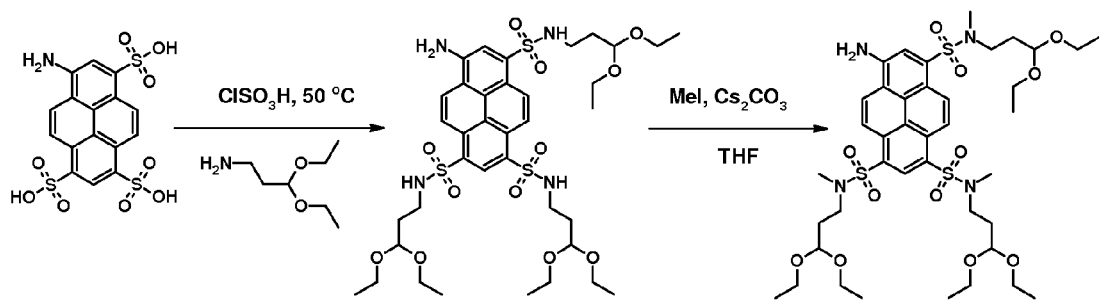
FIG. 26 illustrates the preparation of a representative pI marker of the invention.
Figure 26:
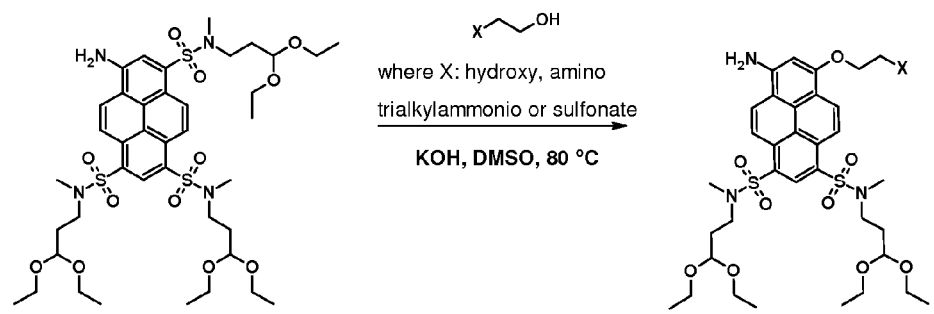
Figure 26:
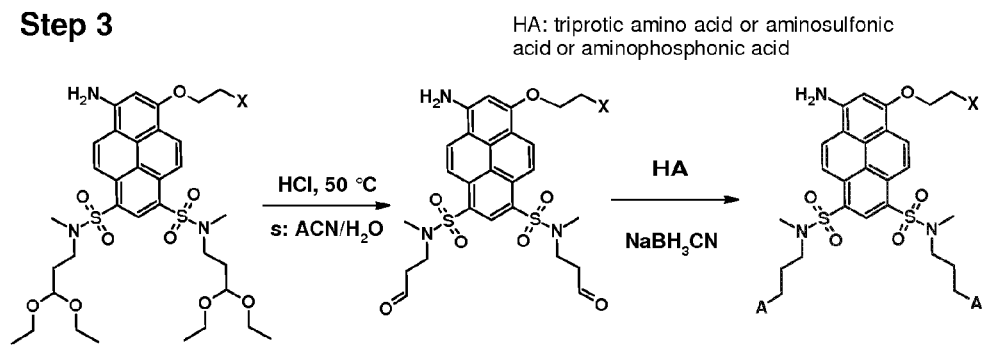
Figure 27:
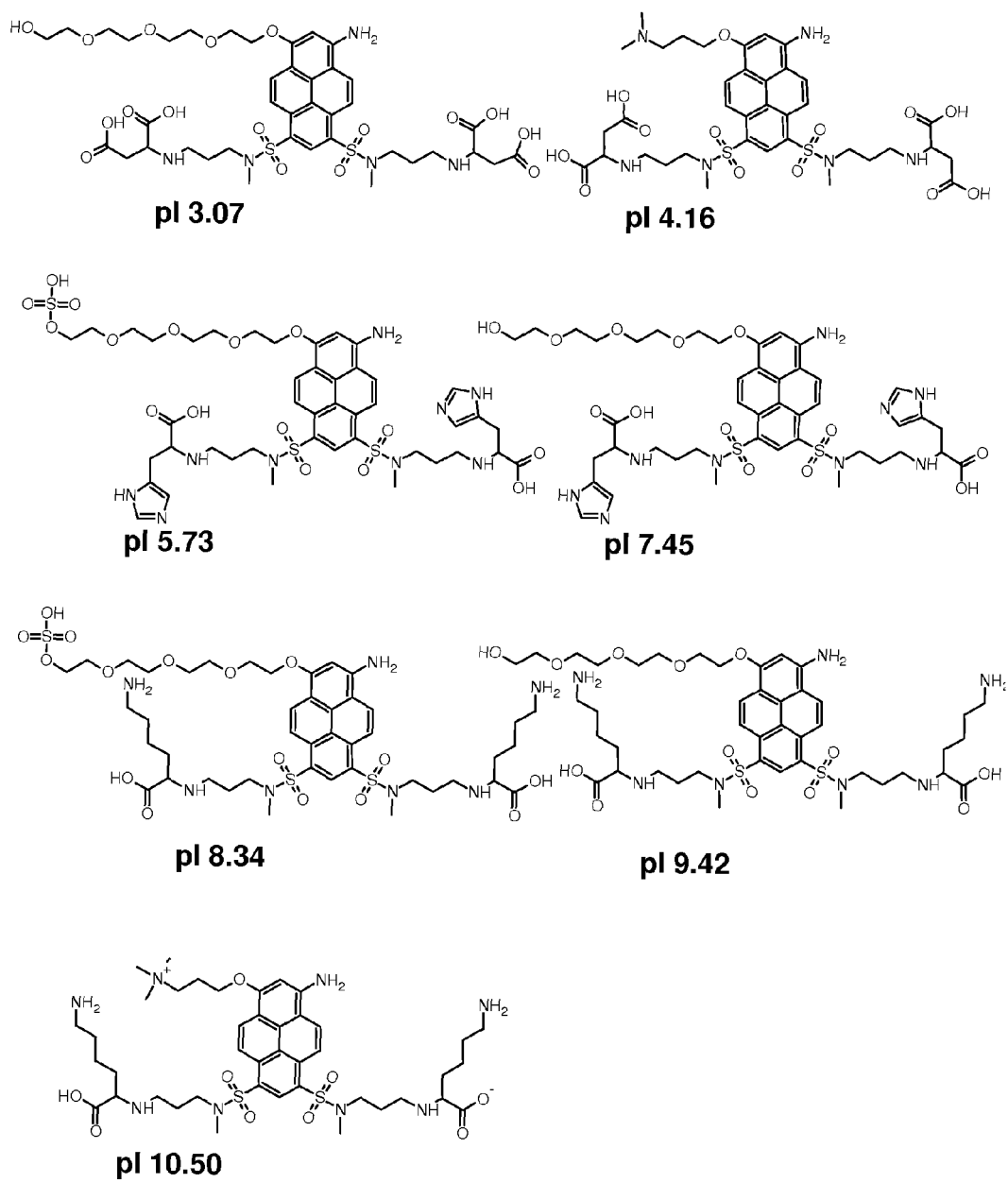
FIG. 27 illustrates representative pI markers of the invention.

FIG. 26 shows a general scheme according to which aryl-bis(triprotic sulfonamide) ampholytes can be synthesized. Representative ampholytes are shown in FIG. 27. Table 6 lists representative ampholytes that can be made from amino dicarboxylic acids as sources of the triprotic groups.

TABLE 6

Representative ampholytes derived from amino dicarboxylic acids.

| pI | HA | Titrant derived from | -dz/dpH |
|---|---|---|---|
| 0.95 | Aminomalonic acid | Isethionic acid | 1.25 |
| 2.02 | Aspartic acid | Isethionic acid | 1.15 |
| 2.24 | Glutamic acid | Isethionic acid | 1.17 |
| 3.04 | Aminomalonic acid | Ethylene glycol | 1.16 |
| 3.04 | Aminomalonic acid | Dimethyl-aminopropanol | 1.16 |
| 3.04 | Aminomalonic acid | Choline | 1.17 |
| 3.05 | 3-Aminopentanedicarboxylic acid | Isethionic acid | 1.21 |
| 3.1 | Aspartic acid | Ethylene glycol | 0.56 |
| 3.1 | Glutamic acid | Ethylene glycol | 0.79 |
| 3.4 | 5-Amino-heptanedicarboxylic acid | Isethionic acid | 1.21 |
| 3.55 | 3-Aminopentanedicarboxylic acid | Ethylene glycol | 1.22 |
| 3.92 | 5-Amino-heptanedicarboxylic acid | Ethylene glycol | 1.19 |
| 3.92 | Glutamic acid | Choline | 1.19 |
| 3.95 | Glutamic acid | N.N-Dimethyl-aminopropanol | 1.2 |
| 4.04 | 3-Aminopentanedicarboxylic acid | N.N-Dimethyl-aminopropanol | 1.22 |
| 4.04 | 3-Aminopentanedicarboxylic acid | Choline | 1.22 |

TABLE 6-continued

Representative ampholytes derived from amino dicarboxylic acids.

| pI | HA | Titrant derived from | −dz/dpH |
|---|---|---|---|
| 4.17 | Aspartic acid | N,N-Dimethyl-aminopropanol | 1.16 |
| 4.18 | Aspartic acid | Choline | 1.17 |
| 4.52 | 5-Amino-heptanedicarboxylic acid | Choline | 1.11 |
| 4.55 | 5-Amino-heptanedicarboxylic acid | N,N-Dimethyl-aminopropanol | 1.13 |

Table 7 lists representative ampholytes derived from iminodicarboxylic acids.

TABLE 7

Representative ampholytes derived from iminodicarboxylic acids.

| pI | HA | Titrant derived from | −dz/dpH |
|---|---|---|---|
| 1.82 | Iminodiacetic acid | Isethionic acid | 1.25 |
| 2.24 | N-(Acetic) 3-aminopropionic acid | Ethylene glycol | 1.19 |
| 2.29 | Iminodiacetic acid | Ethylene glycol | 1.23 |
| 2.79 | Iminodiacetic acid | N,N-Dimethyl-aminopropanol | 1.21 |
| 2.79 | Iminodiacetic acid | Choline | 1.21 |
| 2.92 | N-(Acetic) 3-aminopropionic acid | Ethylene glycol | 1.01 |
| 3.09 | Iminodi(3-propionic acid) | Isethionic acid | 1.26 |
| 3.5 | Iminodi(3-propionic acid) | Ethylene glycol | 1.3 |
| 3.6 | N-(Acetic) 3-aminopropionic acid | N,N-Dimethyl-aminopropanol | 1.19 |
| 3.6 | N-(Acetic) 3-aminopropionic acid | Choline | 1.19 |
| 3.89 | Iminodi(3-propionic acid) | Choline | 1.26 |
| 3.9 | Iminodi(3-propionic acid) | N,N-Dimethyl-aminopropanol | 1.26 |

Table 8 lists representative ampholytes made from diamino carboxylic acids as sources of the triprotic groups.

TABLE 8

Representative ampholytes derived from diamino carboxylic acids.

| pI | HA | Titrant derived from | −dz/dpH |
|---|---|---|---|
| 5.69 | Histidine | Isethionic acid | 0.76 |
| 7.31 | Histidine | Ethylene glycol | 0.39 |
| 8.38 | Lysine | Isethionic acid | 1.15 |
| 9.45 | Lysine | N,N-Dimethylaminopropanol | 0.75 |
| 10.5 | Lysine | Choline | 1.16 |

Alternative synthetic schemes can also be applied without deviating from the invention. For example, in FIG. 26, in step 2, one can start with a diol for $X-CH_2CH_2OH$. After its attachment to position 1 of the pyrene core as an alkoxyalcohol, one can convert the alcohol to a tosylate, then convert the tosylate to an amino or trialkylammonium group by reacting it with an amine, or to a sulfonate, by reacting it with $NaHSO_3$, as is well known in the art. One can also start in Step 1 of FIG. 26 with 1-hydroxy-8-amino-pyrene-4,6-disulfonic acid, without changing the nature of the buffering or titrating group or altering the pI of the resulting ampholyte.

Table 9 lists of some of the ampholytes in order of their increasing pI values that fall within the scope of this invention, along with their characteristic $[-dz(pH)/d(pH)_{pI}]$ values indicating that the invention provides hitherto unavailable ampholytes.

TABLE 9

Representative ampholytes.

| pI | Sulfonamido buffering group derived from | Titrant group derived from | −dz/dpH | −dz/dpH |
|---|---|---|---|---|
| 0.95 | Aminomalonic acid | Isethionic acid | 1.25 | 1.25 |
| 1.82 | Iminodiacetic acid | Isethionic acid | 1.25 | 1.25 |
| 2.02 | Aspartic acid | Isethionic acid | 1.15 | 1.15 |
| 2.24 | Glutamic acid | Isethionic acid | 1.17 | 1.17 |
| 2.24 | N-(Acetic)-3-aminopropionic acid | Ethylene glycol | 1.19 | 1.19 |
| 2.29 | Iminodiacetic acid | Ethylene glycol | 1.23 | 1.23 |
| 2.42 | 4-imidazolecarboxylic acid | Isethionic acid | 1.17 | |
| 2.49 | Glycine | Isethionic acid | 1.14 | 1.14 |
| 2.69 | 4,5-imidazoledicarboxylic acid | Choline | 1.11 | |
| 2.7 | Aminomalonic acid | Choline | 1.15 | 1.15 |
| 2.79 | Iminodiacetic acid | Dimethylaminopropanol | 1.21 | 1.21 |
| 2.79 | Iminodiacetic acid | Choline | 1.21 | 1.21 |
| 2.92 | N-(Acetic)-3-aminopropionic acid | Ethylene glycol | 1.01 | 1.01 |
| 3.04 | Aminomalonic acid | Dimethylaminopropanol | 1.17 | 1.16 |
| 3.04 | Aminomalonic acid | Choline | 1.16 | 1.17 |
| 3.05 | 3-Aminopentanedicarboxylic acid | Isethionic acid | 1.21 | 1.21 |
| 3.09 | Iminodipropionic acid | Isethionic acid | 1.26 | 1.26 |
| 3.10 | Aspartic acid | Ethylene glycol | 0.56 | 0.56 |
| 3.10 | Glutamic acid | Ethylene glycol | 0.79 | 0.79 |
| 3.32 | 4-Imidazoleacetic acid | Isethionic acid | 1.17 | 1.1 |
| 3.39 | 2-Hydroxy-4-aminobutyric acid | Isethionic acid | 1.10 | |
| 3.40 | 4-Aminoheptanedicarboxylic acid | Isethionic acid | 1.21 | 1.21 |
| 3.50 | Iminodipropionic acid | Ethylene glycol | 1.30 | 1.3 |
| 3.55 | 3-Aminopentanedicarboxylic acid | Ethylene glycol | 1.22 | 1.22 |

TABLE 9-continued

Representative ampholytes.

| pI | Sulfonamido buffering group derived from | Titrant group derived from | −dz/dpH | −dz/dpH |
|---|---|---|---|---|
| 3.60 | 3-Aminopentanedicarboxylic acid | Dimethylaminopropanol | 1.19 | 1.19 |
| 3.60 | N-(Acetic)-3-aminopropionic acid | Choline | 1.19 | 1.19 |
| 3.63 | Beta-alanine | Isethionic acid | 1.15 | 1.15 |
| 3.65 | 2-Hydroxy-4-aminobutyric acid | Choline | 1.16 | 1.16 |
| 3.66 | Aspartic acid | Choline | 1.19 | 1.19 |
| 3.77 | Iminodi(4-butyric acid) | Isethionic acid | 1.17 | 1.17 |
| 3.85 | Iminodi(3-propionic acid) | Choline | 1.26 | 1.26 |
| 3.89 | Iminodi(3-propionic acid) | Choline | 1.26 | 1.26 |
| 3.90 | Iminodi(propionic acid) | Dimethylaminopropanol | 1.26 | 1.26 |
| 3.92 | 4-Aminoheptanedicarboxylic acid | Ethylene glycol | 1.19 | 1.19 |
| 3.92 | Glutamic acid | Choline | 1.19 | 1.19 |
| 3.95 | Glutamic acid | Dimethylaminopropanol | 1.20 | 1.2 |
| 4.04 | 3-Aminopentanedicarboxylic acid | Dimethylaminopropanol | 1.22 | 1.22 |
| 4.04 | 3-Aminopentanedicarboxylic acid | Choline | 1.22 | 1.22 |
| 4.06 | Iminodiacetic acid | Choline | 1.22 | 1.22 |
| 4.10 | 3-Hydroxy-4-aminobutyric acid | Choline | 1.15 | 1.15 |
| 4.17 | Aspartic acid | Dimethylaminopropanol | 1.16 | 1.16 |
| 4.18 | Aspartic acid | Choline | 1.17 | 1.17 |
| 4.26 | Beta-alanine | Choline | 1.15 | 1.15 |
| 4.26 | Iminodipropionic acid | N,N'N'-trimethylpiperazine | 1.30 | 1.3 |
| 4.32 | 5-Aminocaproic acid | Isethionic acid | 1.15 | 1.15 |
| 4.52 | 4-Aminoheptanedicarboxylic acid | Choline | 1.11 | 1.11 |
| 4.53 | 4-Aminobutyric acid | Choline | 1.15 | 1.15 |
| 4.55 | 4-Aminoheptanedicarboxylic acid | Dimethylaminopropanol | 1.13 | 1.13 |
| 4.56 | Iminodiacetic acid | N,N'N'-trimethylpiperazine | 1.23 | 1.23 |
| 4.65 | Glycine | Choline | 1.15 | 1.15 |
| 5.06 | Piperazine-N-ethansulfonic acid | N-(2-hydroxyethyl)-N-methyl-N'(2-sulfoethyl)-N'-methylethylenediamine | 0.73 | 0.73 |
| 5.52 | N-(2-Hydroxyethyl-(ethoxy(ethoxy))piperazine | Isethionic acid | 1.13 | |
| 5.61 | Piperazine-N-ethansulfonic acid | N-(2-hydroxyethyl)-N-methyl-N'(2-sulfoethyl)-N'-methyl-propylenediamine | 1.19 | 1.19 |
| 5.69 | Histidine | Isethionic acid | 0.76 | |
| 5.98 | Piperazine-N-3-propanesulfonic acid | N-(2-hydroxyethyl)morpholine | 0.74 | 0.74 |
| 6.09 | Piperazine-N-3-propanesulfonic acid | N-(2-hydroxyethyl)-N-methyl-N'(2-sulfoethyl)-N'-methyl-propylenediamine | 0.90 | 0.9 |
| 6.20 | Piperazine-N'-ethansulfonic acid | Dimethylaminopropanol | 0.93 | 0.93 |
| 6.20 | 5-Hydroxymethyl imidazole | Isethionic acid | 1.15 | |
| 6.25 | 4-Hydroxymethyl imidazole | Isethionic acid | 1.15 | |
| 6.29 | Aminomethylphosphonic acid | Dimethylaminopropanol | 1.14 | |
| 6.46 | Amino-bis(diethylene glycol) | Isethionic acid | 1.15 | |
| 6.47 | 2-hyroxypropylmorpholine | Isethionic acid | 1.15 | |
| 6.53 | Imidazole | Isethionic acid | 1.15 | |
| 6.73 | Morpholine | Isethionic acid | 1.15 | 1.15 |
| 6.75 | 4-Imidazolecarboxylic acid | Dimethylaminopropanol | 1.15 | |
| 6.87 | 4-Imidazoleacetic acid | Dimethylaminopropanol | 1.17 | |
| 7.01 | 2-Aminoethylmorpholine | Isethionic acid | 1.15 | |
| 7.31 | Histidine | Ethylene glycol | 0.39 | |
| 7.50 | N-(2-Aminoethyl)-tris(hydroxymethyl)amino methane | Isethionic acid | 1.14 | |
| 7.78 | Tris(hydroxymethyl)amino methane | Isethionic acid | 1.15 | 1.15 |
| 8.00 | N,N-di(2-hydroxyethyl)-N'-methyl-ethylenediamine | Isethionic acid | 1.14 | |
| 8.23 | Diethanolamine | Isethionic acid | 1.15 | 1.15 |
| 8.38 | Lysine | Isethionic acid | 1.15 | |
| 8.66 | (2-Hydroxyethyl-(ethoxy-(ethoxy))amine | Isethionic acid | 1.15 | |
| 8.70 | Glycine | Dimethylaminopropanol | 1.20 | 1.2 |

TABLE 9-continued

Representative ampholytes.

| pI | Sulfonamido buffering group derived from | Titrant group derived from | −dz/dpH | −dz/dpH |
|---|---|---|---|---|
| 8.87 | N-Ethyl-N-(2-hydroxyethyl-(ethoxy(ethoxy))amine | Isethionic acid | 1.14 | |
| 8.89 | 5-Aminocaproic acid | Dimethylaminopropanol | 0.48 | 0.48 |
| 8.93 | N-Propyl(beta-alanine) | Dimethylaminopropanol | 0.68 | 0.68 |
| 9.04 | Di(3-propanol)amine | Isethionic acid | 1.15 | 1.15 |
| 9.09 | Glycine | Choline | 1.10 | 1.1 |
| 9.13 | 2-Hydroxy-4-aminobutyric acid | Dimethylaminopropanol | 0.92 | 0.92 |
| 9.20 | N,N-(Di(2-hydroxyethyl)ethylenediamine | Isethionic acid | 1.17 | 1.17 |
| 9.26 | Dimethylamine | Isethionic acid | 1.15 | 1.15 |
| 9.27 | 2-Hydroxy-4-aminobutyric acid | Dimethylaminopropanol | 0.36 | 0.36 |
| 9.31 | Iminodi(4-butyric acid)) | Dimethylaminopropanol | 0.34 | 0.34 |
| 9.33 | N-ethyl-N-(2-hydroxyethyl)amine | Isethionic acid | 1.14 | |
| 9.39 | Diethylamine | Isethionic acid | 1.15 | 1.15 |
| 9.43 | N-Methyl-N',N'-(dimethyl)ethylenediamine | Isethionic acid | 1.15 | |
| 9.45 | Lysine | Dimethylaminopropanol | 0.75 | 1.15 |
| 9.48 | N,N'-Di(2-hydroxyethyl)ethylenediamine | Isethionic acid | 1.17 | 1.17 |
| 9.59 | N-Propylamine | Isethionic acid | 1.15 | 1.15 |
| 9.61 | Lysine | Dimethylaminopropanol | 0.75 | |
| 9.63 | Ethanolamine | Isethionic acid | 1.15 | 1.15 |
| 9.65 | Piperazine | Isethionic acid | 1.17 | 1.17 |
| 9.8 | 3-Hydroxy-4-aminobutyric acid | Choline | 1.09 | 1.09 |
| 10.00 | Methylamine | Isethionic acid | 1.15 | 1.15 |
| 10.01 | N,N'-Dimethylethylenediamine | Isethionic acid | 1.15 | 1.15 |
| 10.02 | Ethylenediamine | Isethionic acid | 1.15 | 1.15 |
| 10.05 | 5-Aminocaproic acid | Choline | 1.15 | 1.15 |
| 10.27 | Beta-alanine | Choline | 0.98 | 0.98 |
| 10.34 | Propylenediamine | Isethionic acid | 1.15 | 1.15 |
| 10.36 | 4-Aminobutyric acid | Choline | 1.05 | 1.05 |
| 10.50 | Lysine | Choline | 1.16 | |
| 10.87 | 2-Hydroxy-4-aminobutyric acid | Choline | 1.07 | 1.07 |

Figure 28A:
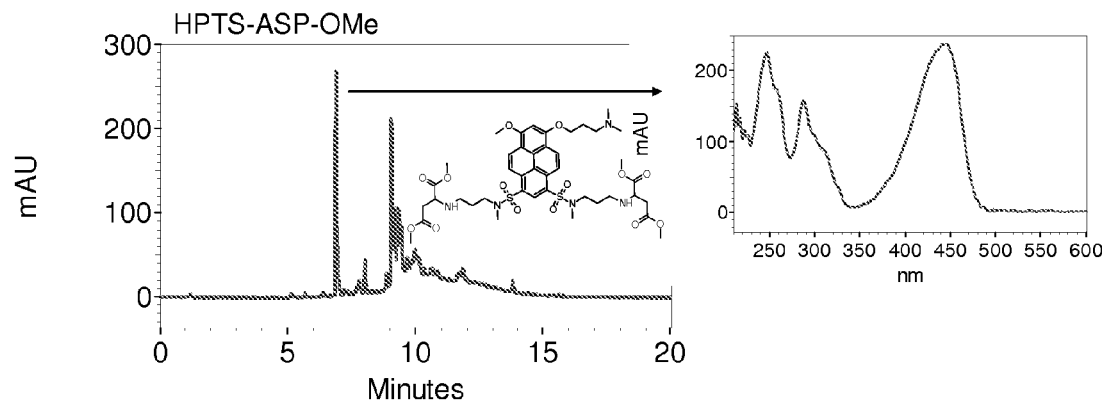
FIGS. 28A and 28B show the chromatograms of the pI 4.1 ampholytes made according to general structures C and D in FIG. 1 (HPTS-ASP-OMe and APTS-ASP-OMe), respectively, using aspartic acid as the triprotic element in the respective sulfonamide groups, prior to deprotection of the carboxylic acid methyl esters and prior to purification by preparative-scale HPLC. Inserts show the characteristic absorption spectra of the ampholytes.
Figure 28B:
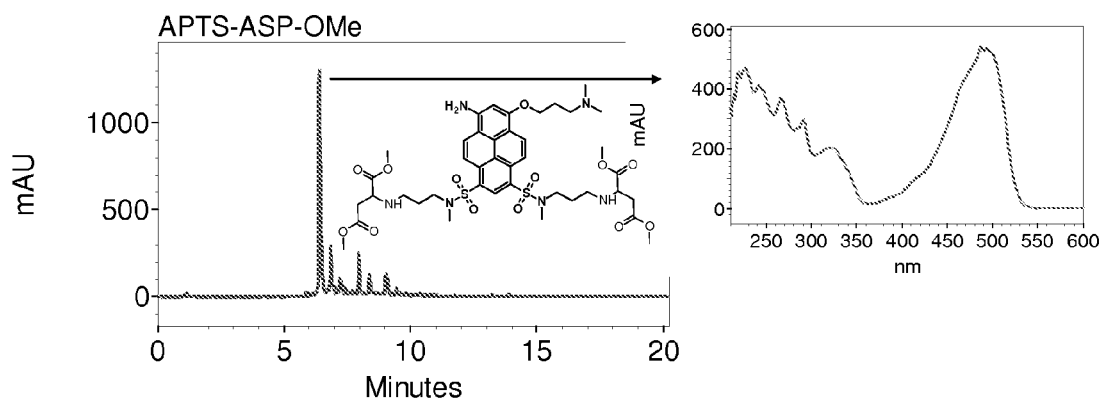

FIGS. 28A and 28B show the chromatograms of the pI 4.1 ampholytes made according to general structures C and D in FIG. 1 (HPTS-ASP-OMe and APTS-ASP-OMe), respectively, using aspartic acid as the triprotic element in the respective sulfonamide groups, prior to deprotection of the carboxylic acid methyl esters and prior to purification by preparative-scale HPLC. Inserts show the characteristic absorption spectra of the ampholytes.

Figure 29:
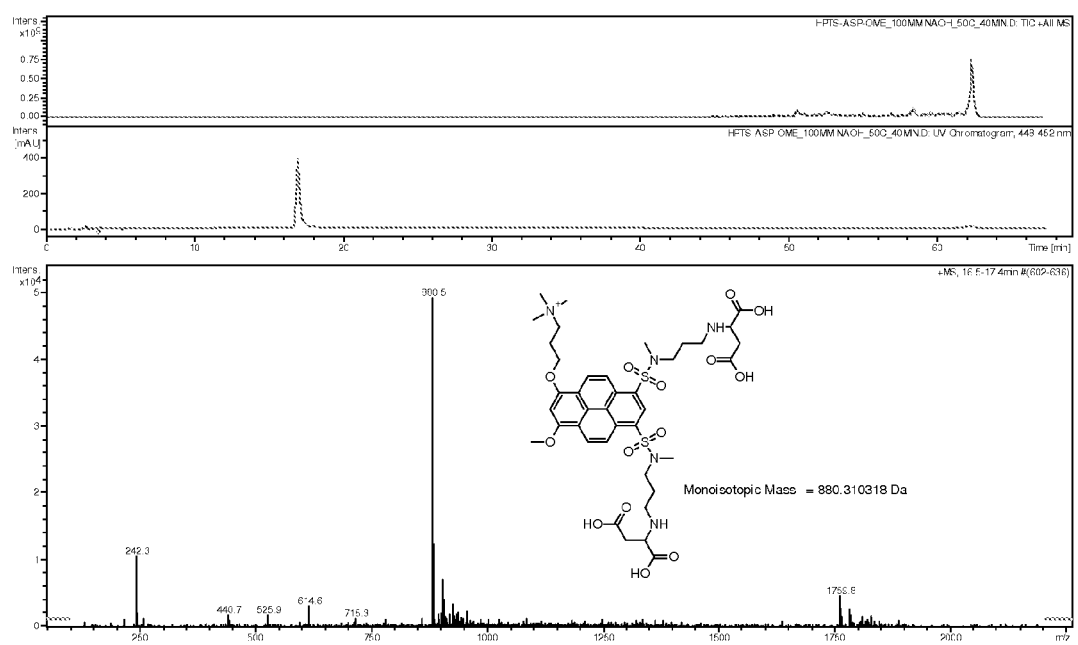
FIG. 29 shows the LC/MS analysis of the pI 4 marker corresponding to the general structure of FIG. 1, scheme C, after preparative-scale HPLC purification and conversion to the isoelectric form, indicating the high purity and identity of the material.

FIG. 29 shows the results of a LC/MS analysis of the pI 4 marker corresponding to the general structure of FIG. 1, scheme C, after preparative-scale HPLC purification and conversion to the isoelectric form, indicating the high purity and identity of the material.

Figure 30:
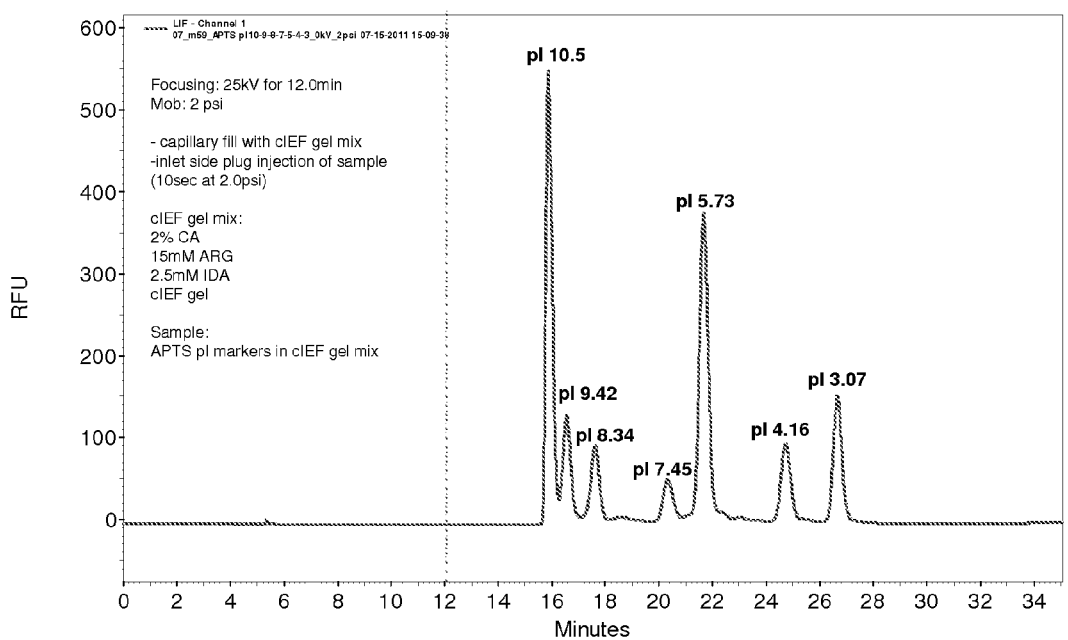
FIG. 30 shows an electropherogram (LIF) for a selection of the ampholytes (APTS-based markers) synthesized according to the present invention.

FIG. 30 shows an electropherogram (LIF) for a selection of the ampholytes (APTS-based markers) synthesized according to the present invention. The capillary isoelectric focusing separation was obtained on a Beckman MDQ capillary electrophoretic instrument (Brea, Calif.), at 25 kV potential, using a 3<pI<10 Ampholine carrier ampholyte mixture. The separated components were moved by the laser-induced fluorescence detector (488 nm argon ion laser) using 1 psi pressure.

Figure 31:
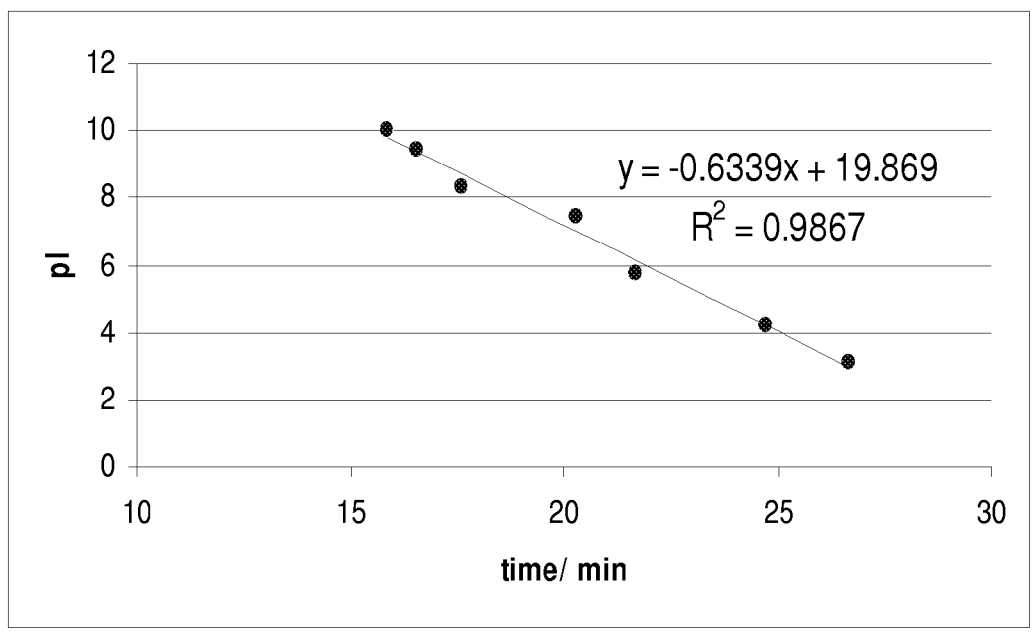
FIG. 31 shows a calibration curve for the pH gradient obtained with the APTS-based pI markers of FIG. 30.

FIG. 31 shows a calibration curve for the pH gradient obtained with the APTS-based pI markers.

Labeling Agents

As noted above, in certain embodiments, the pI markers are further functionalized to include one or more functional groups that render the markers reactive to molecules of interest to provide conjugates of the marker and the molecule of interest. In this embodiment, the marker is a tetra-substituted pyrene marker having first, second, and third substituents as described above. In one embodiment, the fourth substituent is an ether group comprising a functional group effective for covalently coupling the compound to a second compound to provide a conjugate. In another embodiment, the fourth substituent is an amine group comprising a functional group effective for covalently coupling the compound to a second compound to provide a conjugate. In a further embodiment, the fourth substituent is a thioether group comprising a functional group effective for covalently coupling the compound to a second compound to provide a conjugate.

In one embodiment, the fourth substituent is an amino group.

It will be appreciated that due to molecular symmetry, positions 6 and 8 of the pyrene markers of the invention are interchangeable. Therefore, the third and fourth substituents, as described herein, are interchangeable (e.g., in one embodiment, the third substituent is an ether group, amine group, or thioether group further comprising a functional group effective for covalently coupling the compound to a second compound to provide a conjugate).

In one embodiment, the labeling agent of the invention has formula (IV):

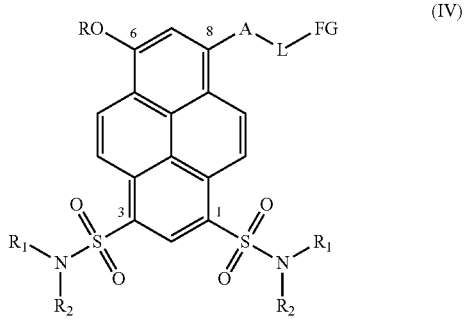

(IV)

wherein

A is selected from the group consisting of O, S, NR, and NH;

L is a linker covalently coupling A to FG;

FG is a functional group reactive to covalently couple the compound to a compound of interest;

R is selected from the group consisting of
—$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20,
wherein each is coupled to a non-charged group or at least one moiety selected from the group consisting of $NH_2$, $NHR$, $N(R)_2$, $N(R)_3^+$, azaaryl, hydroxyaryl, carboxylic acid or carboxylate, sulfonic acid or sulfonate, and hydrogensulfate or sulfate group; and $R_1$ and $R_2$ at each occurrence are independently selected from the group consisting of
—$(CH_2)_n$— where n is from 1 to 12,
—$(CH_2CH<)_n$— where n is from 1 to 12,
—$(CH_2CH_2O)_n$— where n is from 1 to 20, and
—$(CH_2CH(OH)CH_2O)_n$— where n is from 1 to 20,
wherein each is coupled to a non-charged group or at least one of a group selected from the group consisting of $NH_2$, $NHR$, $N(R)_2$, azaaryl, hydroxyaryl, and carboxylic acid group.

In another embodiment, the definitions of substituents R, $R_1$, $R_2$, and $R_3$ for formula (IV) are as set forth above for formula (III).

It will be appreciated that for the ampholytes of formula (IV), the combination of the electrolyte groups in R, $R_1$ and $R_2$ lead to a species that can have a negative, net zero and a positive charge as the pH of the solution is varied from 0 to 14.

In the above listings, NHR, NR or $N(R)_2$, and $N(R)_3^+$ refer to secondary, tertiary, and quaternary amine groups, respectively. For NHR, NR, $N(R)_2$, and $N(R)_3^+$, in certain embodiments, R in these groups is as described above for R (i.e., —$(CH_2—)_n$ or —$(CH_2—CH<)_n$, where 0<n<12; —$(CH_2CH_2O—)_n$, where 1<n<20; and —$(CH_2CH(OH)CH_2O—)_n$, where 1<n<20; each connected to hydrogen). In certain embodiments R is a C1-C12 alkyl group.

Suitable linkers include groups derived from alkylating agents that effectively alkylate A (i.e., O, S, NR, NH) to provide ether, thioether, tertiary amine, or secondary amine groups (e.g., O—$CH_2$—, S—$CH_2$—, NR—$CH_2$—, and NH—$CH_2$—), respectively. The alkylating group may include the functional group (FG) or may be further modified to include the functional group. The linker can include from one to twenty carbon atoms (e.g., alkylene), can optionally be substituted with one or more hetero atoms, and further include one or more groups (e.g., keto, carboxylic acid, ester, amide).

Suitable functional groups include nucleophilic groups for reaction with electrophilic groups on the molecules to be labeled (i.e., compound of interest) and electrophilic groups for reaction with nucleophilic groups on the molecules to be labeled. Conventional labeling groups useful as functional groups in the labeling agents of the invention are known in the art (see, e.g., Molecule Probes Catalog). Representative functional groups include amine, secondary amine, carboxylic acid, reactive carboxylic acids ester (e.g., N-hydroxysuccinimide and pentafluorophenyl esters), acrylate ester or amide, alkyl or arylboronate, and alkylhalide groups.

For the labeling agents of formula (IV), in certain embodiments, $R_1$ at each occurrence is the same. In other embodiments, $R_1$ at each occurrence is different. In certain embodiments, $R_1$ at each occurrence includes a group independently selected from amino, secondary amino, tertiary amino, azaryl, hydroxyaryl, carboxylic acid, carboxylate, sulfonic acid, sulfonate, hydrogen sulfate, and sulfate groups. In certain embodiments, R includes a group selected from amino, secondary amino, tertiary amino, quaternary amino, azaryl, hydroxyaryl, carboxylic acid, carboxylate, sulfonic acid, sulfonate, hydrogensulfate, and sulfate groups. In other embodiments, R includes a moiety selected from a poly(ethylene glycol) moiety, a poly(propylene glycol) moiety, a linear oligo- or polysaccharide moiety, a branched oligo- or polysaccharide moiety, and a cyclic oligo- or polysaccharide moiety.

In certain embodiments of the labeling agents of formula (IV), $R_1$ and $R_2$ independently at each occurrence can be taken together with the nitrogen to which they are attached to form a heterocyclic ring, such as a piperidine ring, a piperazine ring, or a morpholine ring. See, for example, FIG. 21.

Figure 32:
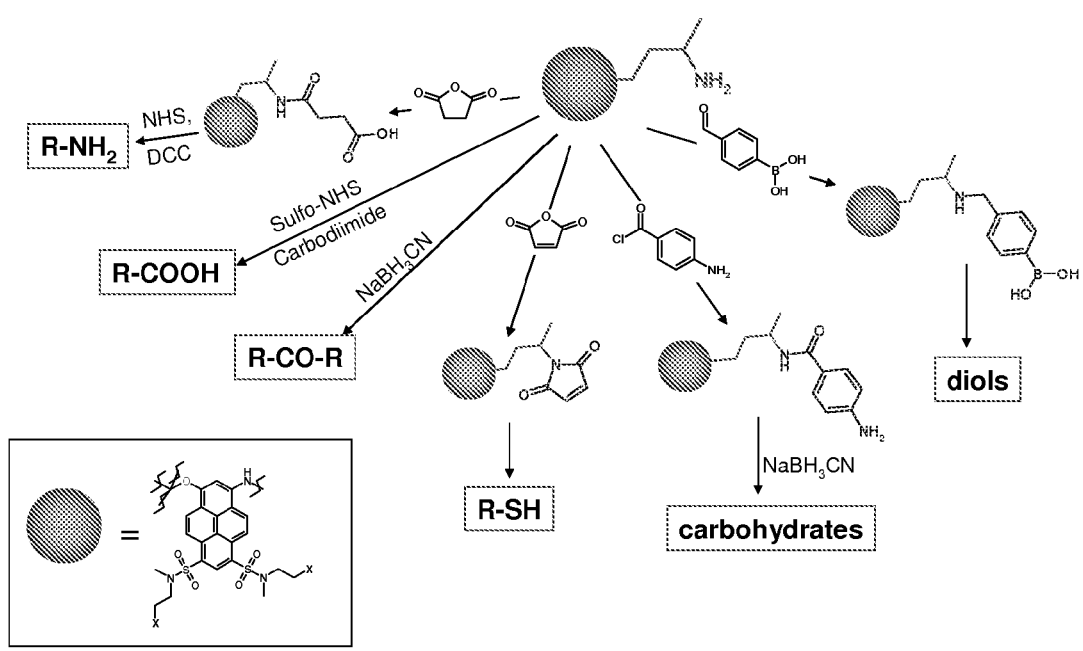
FIG. 32 is a schematic representation of methods for reacting amino-containing ampholytes of the invention (e.g., reacting group is attached to the anilinic 8-amino group) with molecules of interest to provide fluorescent conjugates.

In addition to serving as ampholytes, the compounds described in this invention can also serve as fluorescent tags, once the reacting group is attached to the anilinic 8-amino group as shown, for example, in FIG. 32 for the general compound class of FIG. 1, schematic D, or to one of the oxygen atoms at the 1- or 8-positions in FIG. 32 for the general compound class of FIG. 1, schematic C, and X represent the (monoprotic) or (diprotic) or (triprotic) moieties of this invention in the 4- and 6-sulfonamide groups.

Marker Conjugates

In another aspect of the invention, marker conjugates are provided. The marker conjugates are prepared by covalently coupling a labeling agent of the invention to a molecule of interest. Representative molecules of interest that are advantageously labeled with the agents of the invention to provide marker conjugates include sugars, polysaccharides, amino acids, peptides, and proteins. Marker conjugates and methods for labeling molecules of interest are described below and illustrated schematically in FIG. 32.

Separation Methods

In a further aspect, the invention provides separation methods that advantageously incorporate one or more pI marker of the invention. In one embodiment, the invention provides a method for establishing the shape of a pH gradient between an anode and a cathode across an electrophoretic device in an isoelectric focusing or isoelectric trapping experiment. In one embodiment, this method includes (a) introducing one or more pI markers of the invention having a known pI value into the electrophoretic device; and (b) applying an electric field sufficient for a period of time sufficient to separate and concentrate the one or more pI markers.

In one embodiment, the method further includes determining the position of the separated and concentrated pI markers in the electrophoretic device (e.g., by absorbance or fluorescence measurement), and plotting their pI values as a function of their position in the electrophoretic device thereby establishing the shape of pH gradient in the device.

The pI determination can be made in situ. For example, one or more ampholytic analytes can be introduced into the electrophoretic device along with one or more ampholytic analyte prior to applying the electric field, wherein applying the electric field is effective to separate and concentrate the one or more pI markers and the one or more ampholytic analytes. Determining the position of the separated and concentrated pI markers and the separated and concentrated ampholytic analytes in the electrophoretic device establishes the shape of the pH gradient in the electrophoretic device which, in turn allows the determination of the pI value of each of the one or more ampholytic analytes as is well established in the art.

Alternatively, the pI determination can be made ex situ. For example, one or more pI marker is introduced into the electrophoretic device and a sufficient electric field is applied for a sufficient period of time to separate and concentrate the one or more pI markers, followed by the determination of their focusing position which yields the shape of the pH gradient in the electrophoretic device. Then, one or more ampholytic analytes can be introduced into the electrophoretic device and applying an electric field sufficient for a period of time sufficient to separate and concentrate the one or more ampholytic analytes, followed by the determination of the position of the separated and concentrated ampholytic analytes in the electrophoretic device. From these values and the shape of the pH gradient, the pI of each of the one or more ampholytic analytes can be determined as it is well established in the art. Alternatively, the ampholytic analytes can be focused first and their focusing position obtained in the electrophoretic device followed by the determination of the shape of the pH gradient via the subsequent focusing of the pI markers as is well known in the art.

The method is effective for isoelectric focusing methods and devices utilizing a suitable mixture of carrier ampholytes, or an immobilized pH gradient method or device, or a combination of the two. The method is also effective for isoelectric trapping methods and devices utilizing a suitable series of ion-permeable buffering media, in the absence or presence of carrier ampholytes or isoelectric buffers.

Carbohydrate Labeling and Separation Methods

In another aspect of the invention, methods for labeling a carbohydrate are provided. In these methods, a labeling agent of the invention (e.g., a compound of formula (IV)) is reacted with a carbohydrate to provide a labeled carbohydrate.

In one embodiment, the functional group of the labeling agent is an amino group and reacting the carbohydrate to provide a labeled carbohydrate is a reductive amination process (i.e., Schiff base formation between the aldehyde form of the carbohydrate followed in situ by Schiff base reduction (e.g., by sodium cyanoborohydride)). Suitable carbohydrates advantageously labeled by the labeling agents and methods of the invention include carbohydrates that do not include a sialic acid moiety and carbohydrates that include one or more sialic acid moieties.

In one embodiment, the functional group of the labeling agent is a carboxylate, a carboxylic acid, or an active ester of a carboxylic acid and reacting an aminocarbohydrate to provide a labeled carbohydrate is an amidation process (i.e., the carbohydrate has an amino sugar, for example one that is obtained by enzymatic cleavage of an N-linked carbohydrate from a glycoprotein, that is coupled to the electrophilic compound via amide formation before the amino sugar is hydrolyzed to produce ammonia and the sugar).

In a further aspect, the invention provides a method for electrophoretic separation and concentration of one or more carbohydrate analytes. In one embodiment, the method includes (a) reacting one or more carbohydrates with a labeling agent of the invention to provide one or more ampholytic carbohydrates;

(b) introducing the one or more ampholytic carbohydrates into an electrophoretic device; and (c) applying an electric field sufficient for a period of time sufficient to separate and concentrate the one or more ampholytic carbohydrates.

In one embodiment, the method further includes fractionating the separated ampholytic carbohydrates and analyzing the fractions.

Figure 33:
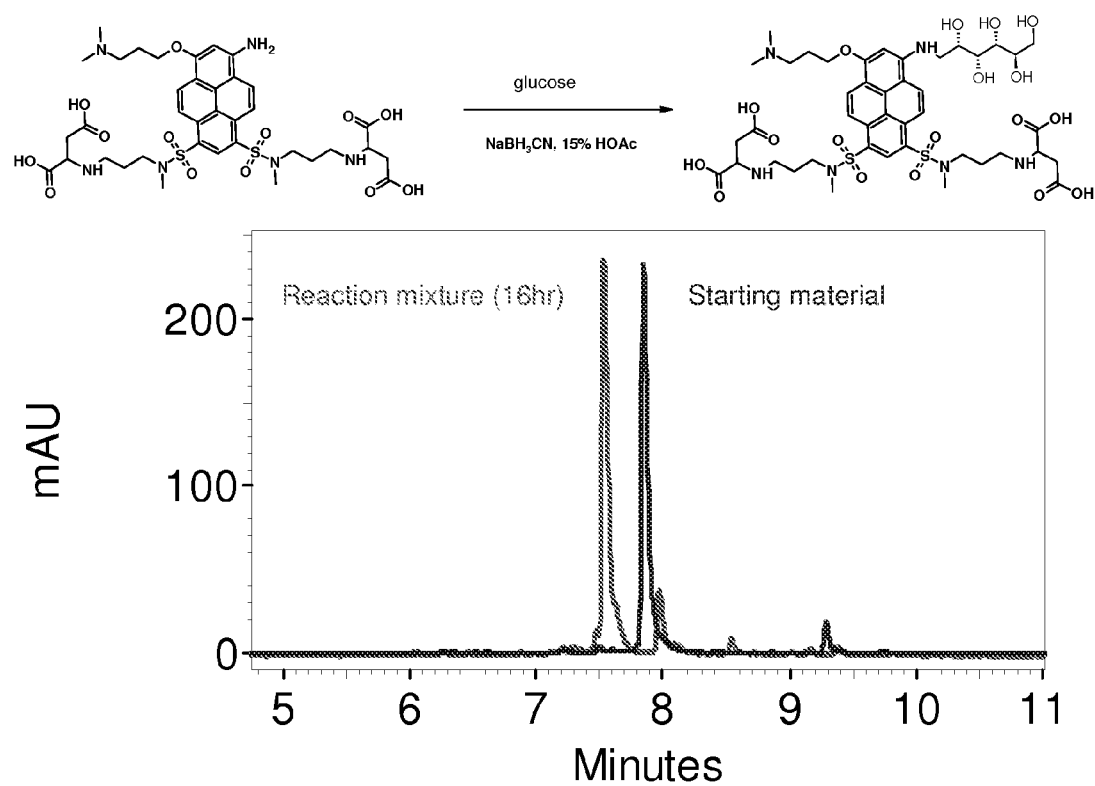
FIG. 33 shows the derivatization reaction of glucose with an aspartic-acid based pI 4 tag and compares the chromatograms of the starting material (pI 4 tag) and the labeling reaction mixture.

As noted above, the ampholytes that correspond to the general structure D in FIG. 1 with at least one or both of the substituents of the anilinic 8-amino group as H, the ampholytes can be used for conjugation of the non-ampholytic carbohydrates rendering them ampholytic and thus making them amenable to isoelectric focusing or isoelectric trapping separation. This is especially advantageous, because isoelectric focusing and isoelectric trapping allow for a selective, electrophoretic concentration of the derivatized carbohydrates, which is of great concern in the analysis of dilute biological samples. Furthermore, tagging the carbohydrates with an ampholytic component allows the easy separation of sialylated carbohydrates from non-sialylated ones, again of great importance in current glycomics studies, because the pI values of the sialylated tagged carbohydrates are lower than those of the non-sialylated tagged carbohydrates. FIG. 33 shows the derivatization reaction of glucose with an aspartic-acid based pI 4 tag and compares the chromatograms of the starting material (pI 4 tag) and the labeling reaction mixture.

Figure 34:
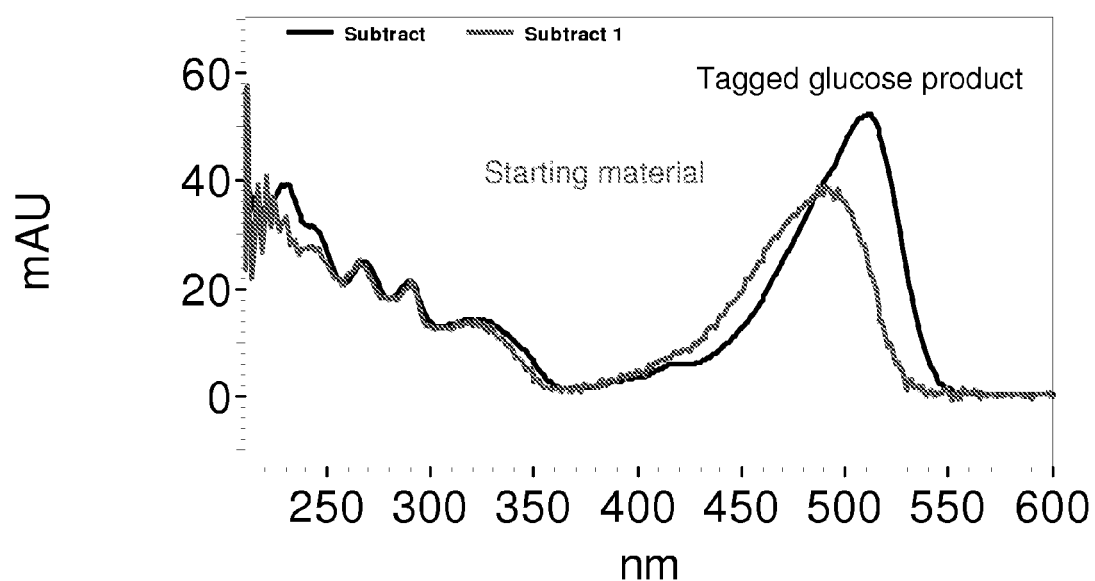
FIG. 34 compares the light absorption spectra of the pI 4 tag and the glucose conjugate: the red-shift in the absorption maximum indicates that the anilinic 8-amino group became attached to a carbon atom of the carbohydrate.

FIG. 34 compares the light absorption spectra of the pI 4 tag and the glucose conjugate: the red-shift in the absorption maximum indicates that the anilinic 8-amino group became attached to a carbon atom of the carbohydrate.

Figure 35:
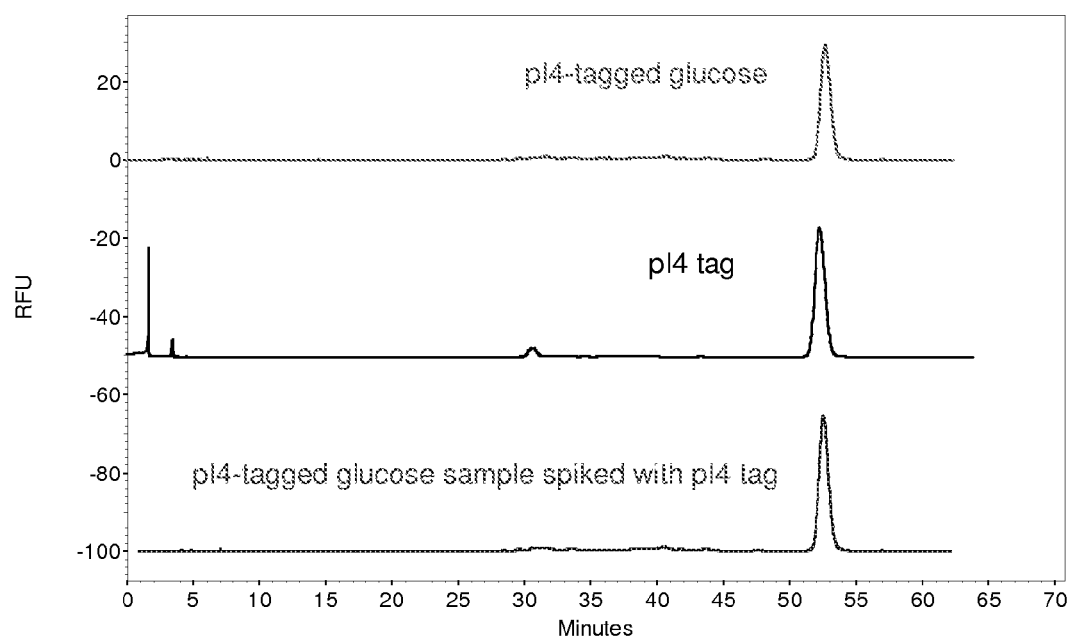
FIG. 35 shows a result of a capillary isoelectric focusing analysis of pI 4-tagged glucose using a fluorescence detector (488 nm argon ion laser): glucose became detectable and its focusing position corresponds to the focusing position of the pI 4 tag, indicating that the reductive amination step did not alter significantly the pI value of the tag.

FIG. 35 shows a result of a capillary isoelectric focusing analysis of pI 4-tagged glucose using a fluorescence detector (488 nm argon ion laser): glucose became detectable and its focusing position corresponds to the focusing position of the pI 4 tag, indicating that the reductive amination step did not alter significantly the pI value of the tag.

Figure 36:
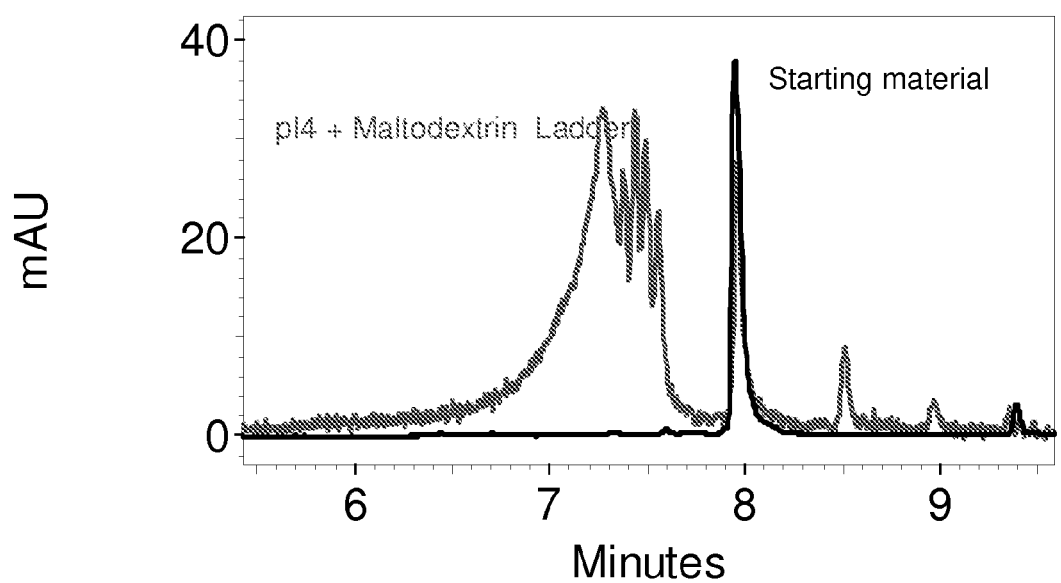
FIG. 36 shows a chromatogram of a pI-4 tagged maltodextrin size ladder.

FIG. 36 shows a chromatogram of a pI-4 tagged maltodextrin size ladder (Beckman-Coulter), again indicating that reductive amination reaction took place and the now ampholytic carbohydrates can indeed be selectively detected courtesy of the pI 4 tag.

Figure 37:
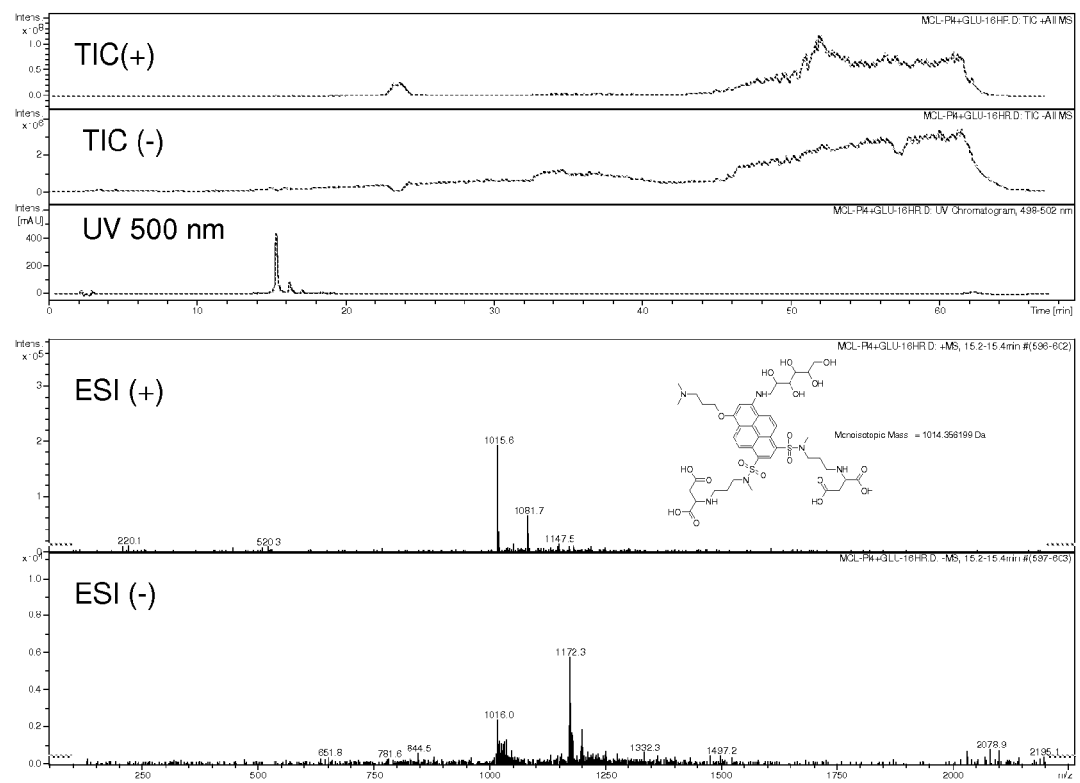
FIG. 37 shows a positive ion mode ESI-MS spectrum and a negative ion mode ESI-MS spectrum of the pI 4 labeled glucose.

FIG. 37 shows a positive ion mode ESI-MS spectrum and a negative ion mode ESI-MS spectrum of the pI 4 labeled glucose indicating that the tagged glucose can be analyzed at a much higher sensitivity in the positive ion mode due to the presence of the pI 4 tag, than in negative ion mode, the only currently possible solution for amino pyrene trisulfonate (APTS) derivatized carbohydrates.

In another aspect, the invention provides a method for chromatographic separation and concentration of one or more carbohydrate analytes. In one embodiment, the method includes (a) reacting one or more carbohydrates with a labeling agent of the invention to provide one or more ampholytic carbohydrates;

(b) introducing the one or more ampholytic carbohydrates into a liquid chromatographic device comprising a column containing a stationary phase selected from the group of an ion exchange medium, a chromatofocusing medium, a reversed-phase medium, a hydrophilic interaction medium or a size exclusion medium; and (c) applying an eluent sufficient for a period of time sufficient to separate and concentrate the one or more ampholytic carbohydrates.

In one embodiment, the method further comprising fractionating the separated ampholytic carbohydrates and analyzing the fractions.

Representative stationary phases include ion exchange media, chromatofocusing media, a reversed-phase (RP) media, hydrophilic interaction (HILIC) media, and a size exclusion (SE) media.

Non-UV-Absorbing Ampholytes

In a further aspect of the invention, non-UV-absorbing ampholytes are provided. These non-UV-absorbing ampholytes differ from those of formulas (I)-(III) in that they do not include an aryl core. These ampholytes include a central nitrogen atom having three substituents.

In one embodiment, the ampholyte comprises a central nitrogen having the following three substituents:

(a) a first substituent comprising a first tertiary amine group, wherein the first tertiary amine group comprises a first weak electrolyte group;

(b) a second substituent comprising a second tertiary amine group, wherein the second tertiary amine group comprises a second weak electrolyte group; and (c) a third substituent comprising a sulfonamide group, wherein the sulfonamide group comprises a group selected from the group consisting of a charge-balancing group and a non-charged group.

In another embodiment, the ampholyte comprises a central nitrogen having the following three substituents:

(a) a first substituent comprising a first sulfonamido group, wherein the first sulfonamido group comprises a first weak electrolyte group;

(b) a second substituent comprising a second sulfonamido group, wherein the second sulfonamido group comprises a second weak electrolyte group; and (c) a third substituent comprising a third sulfonamide group, wherein the third sulfonamide group comprises a group selected from the group consisting of a charge-balancing group and a non-charged group.

In certain embodiments, the first and second weak electrolyte groups are the same. In other embodiments, the first and second weak electrolyte groups are different.

Figure 38A:
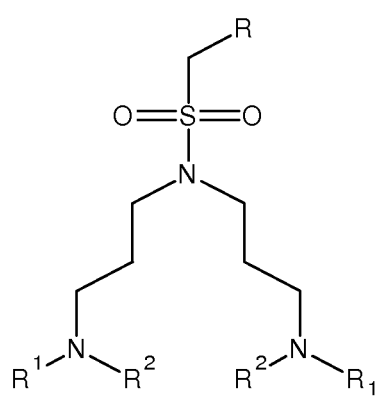
FIGS. 38A and 38B illustrate structures of non-UV-absorbing ampholytes of the invention having adequate steric and electronic isolation of the buffering and charge-balancing groups.
Figure 38B:
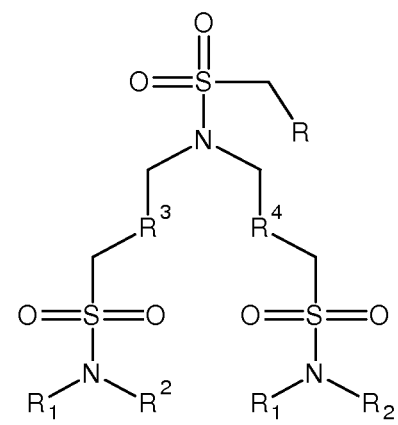

Representative non-arylsulfonamide ampholytes of the invention are shown in FIG. 38. Like their aryl core counterparts, these ampholytes provide adequate steric and electronic isolation of the buffering and charge-balancing groups to make the ampholytes listed in Table 9 and lead to non-UV-absorbing ampholytes with [−dz(pH)/dpH$_{pI}$] values similar to those of the corresponding aryl-bis(sulfonamides).

In one embodiment, the ampholyte has formula (V):

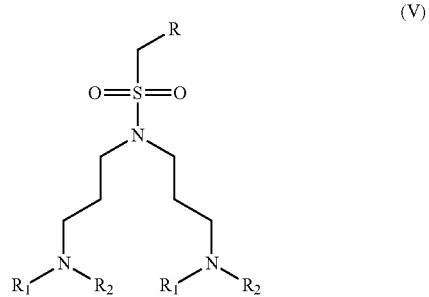

wherein
R is selected from the group consisting of
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each is coupled to hydrogen, a non-charged group, or at least one moiety selected from the group consisting of NH$_2$, NHR, N(R)$_2$, N(R)$_3^+$, azaaryl, hydroxyaryl, carboxylic acid or carboxylate, sulfonic acid or sulfonate, and hydrogensulfate or sulfate group; and R$_1$ and R$_2$ at each occurrence are independently selected from the group consisting of
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each is coupled to a hydrogen, a non-charged group, or at least one moiety selected from the group consisting of NH$_2$, NHR, N(R)$_2$, azaaryl, hydroxyaryl, and carboxylic acid group.

In another embodiment, the ampholyte has formula (VI):

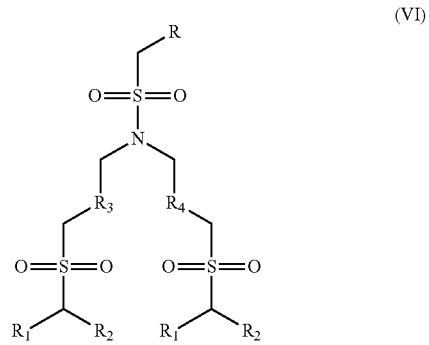

wherein
R is selected from the group consisting of
—(CH$_2$)$_n$— where n is from 1 to 12,
—(CH$_2$CH<)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each is coupled to hydrogen, a non-charged group, or at least one moiety selected from the group consisting of NH$_2$, NHR, N(R)$_2$, N(R)$_3^+$, azaaryl, hydroxyaryl, carboxylic acid or carboxylate, sulfonic acid or sulfonate, and hydrogensulfate or sulfate group;

R₁ and R₂ at each occurrence are independently selected from the group consisting of
—(CH₂)ₙ— where n is from 1 to 12,
—(CH₂CH<)ₙ— where n is from 1 to 12,
—(CH₂CH₂O)ₙ— where n is from 1 to 20, and
—(CH₂CH(OH)CH₂O)ₙ— where n is from 1 to 20,
wherein each is coupled to a hydrogen, a non-charged group, or at least one moiety selected from the group consisting of $NH_2$, NHR, $N(R)_2$, azaaryl, hydroxyaryl, and carboxylic acid group; and R₃ and R₄ are independently selected from the group consisting of
—(CH₂)ₙ— where n is from 1 to 12,
—(CH₂CH<)ₙ— where n is from 1 to 12,
—(CH₂CH₂O)ₙ— where n is from 1 to 20, and
—(CH₂CH(OH)CH₂O)ₙ— where n is from 1 to 20,
wherein each is coupled to hydrogen, a non-charged group, or at least one moiety selected from the group consisting of $NH_2$, NHR, $N(R)_2$, $N(R)_3^+$, azaaryl, hydroxyaryl, carboxylic acid or carboxylate, sulfonic acid or sulfonate, and hydrogensulfate or sulfate group.

The following is a listing of suitable substituents R, R₁, R₂, R₃, and R₄ for the ampholytes illustrated in FIG. 38, where at least one group is selected for R, R₁, R₂, R₃, and R₄, when present, from their respective list:

| R | (—CH₂—)ₙ | 0 < n < 12 |
|---|---|---|
|   | (—CH<)ₙ | 0 < n < 12 |
|   | (—CH₂CH₂O—)ₙ | 1 < n < 20 |
|   | (—CH₂CH(OH)CH₂O—)ₙ | 1 < n < 20 | each connected to one of hydrogen, a non-charged group, or at least one $NH_2$, NHR, $N(R)_2 N(R)_3^+$, azaaryl, hydroxyaryl, carboxylic acid or carboxylate, sulfonic acid or sulfonate, or hydrogensulfate or sulfate group;

| R₁ | (—CH₂—)ₙ | 0 < n < 12 |
|---|---|---|
|   | (—CH<)ₙ | 0 < n < 12 |
|   | (—CH₂CH₂O—)ₙ | 1 < n < 20 |
|   | (—CH₂CH(OH)CH₂O—)ₙ | 1 < n < 20 | each connected to one of hydrogen, a non-charged group, or at least one $NH_2$, NHR, $N(R)_2$, azaaryl, hydroxyaryl, or carboxylic acid group, or their combinations;

| R₂ | (—CH₂—)ₙ | 0 < n < 12 |
|---|---|---|
|   | (—CH<)ₙ | 0 < n < 12 |
|   | (—CH₂CH₂O—)ₙ | 1 < n < 20 |
|   | (—CH₂CH(OH)CH₂O—)ₙ | 1 < n < 20 | each connected to one of hydrogen, non-charged group, or at least one $NH_2$, NHR, $N(R)_2$, azaaryl, hydroxyaryl, or carboxylic acid group, or their combinations;

| R₃ | (—CH₂—)ₙ | 0 < n < 12 |
|---|---|---|
|   | (—CH<)ₙ | 0 < n < 12 |
|   | (—CH₂CH₂O—)ₙ | 1 < n < 20 |
|   | (—CH₂CH(OH)CH₂O—)n | 1 < n < 20 | each connected to one of hydrogen, a non-charged group, or at least one $NH_2$, NHR, $N(R)_2$, $N(R)_3^+$, azaaryl, hydroxyaryl or carboxylic acid group, sulfonic acid or sulfonate, or hydrogensulfate or sulfate group, or their combinations, same as or different from R₁ or R₂ or both; and

| R₄ | (—CH₂—)ₙ | 0 < n < 12 |
|---|---|---|
|   | (—CH<)ₙ | 0 < n < 12 |
|   | (—CH₂CH₂O—)ₙ | 1 < n < 20 |
|   | (—CH₂CH(OH)CH₂O—)ₙ | 1 < n < 20 | each connected to one of hydrogen, a non-charged group, or at least one $NH_2$, NHR, $N(R)_2$, $N(R)_3^+$, azaaryl, hydroxyaryl, or carboxylic acid group, sulfonic acid or sulfonate, or hydrogensulfate or sulfate group, or their combinations, same as or different from R₁ or R₂ or both oxylic acid group or their combinations, same as or different from R₁ or R₂ or R₃ or two or three of them.

It will be appreciated that for the ampholytes of formulas (V) and (VI), the combination of the electrolyte groups in R, R₁ and R₂ lead to a species that can have a negative, net zero and a positive charge as the pH of the solution is varied from 0 to 14.

In the above listings, NHR, $N(R)_2$, and $N(R)_3^+$ refer to secondary, tertiary, and quaternary amine groups, respectively. For NHR, $N(R)_2$, and $N(R)_3^+$, in certain embodiments, R in these groups is as described above for R (i.e., (—CH₂—)ₙ or (—CH₂—CH<)ₙ, where 0<n<12; (—CH₂CH₂O—)ₙ, where 1<n<20; and (—CH₂CH(OH)CH₂O—)ₙ, where 1<n<20; each connected to hydrogen). In certain embodiments R is a C1-C12 alkyl group.

Figure 39:
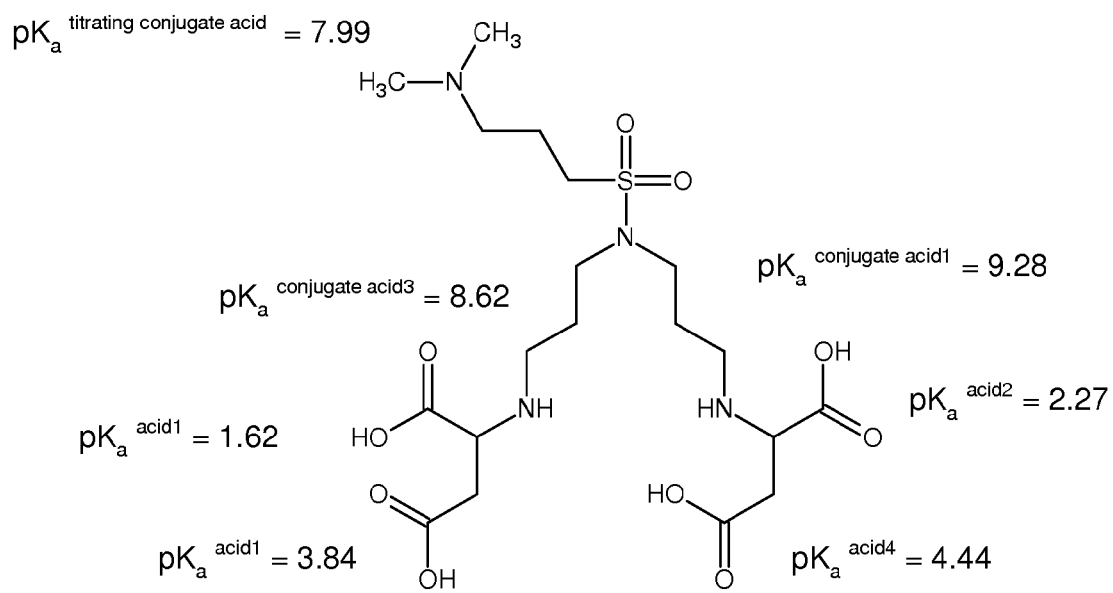
FIG. 39 illustrates a representative non-UV absorbing ampholyte of the invention.
Figure 40:
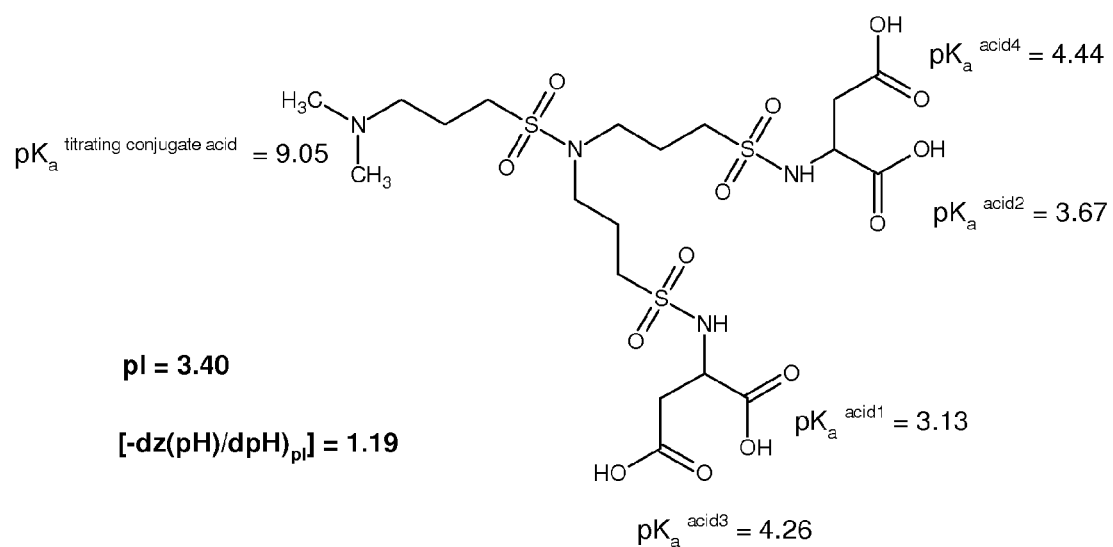
FIG. 40 illustrates a representative non-UV absorbing ampholyte of the invention.

Exemplary structures of such ampholytes along with the corresponding pKa, pI, and $[-dz(pH)/dpH_{pI}]$ values are shown in FIGS. 39 and 40.

While illustrative embodiments have been illustrated and described, it will be appreciated that various changes can be made therein without departing from the spirit and scope of the invention.

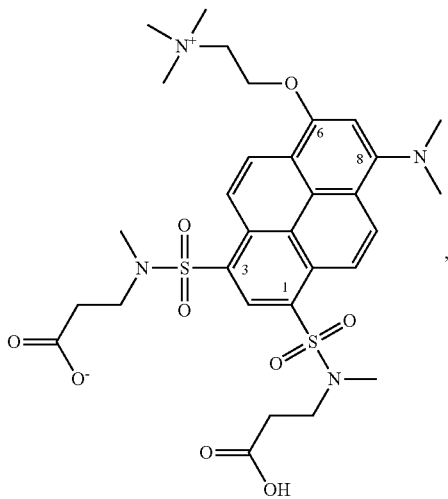

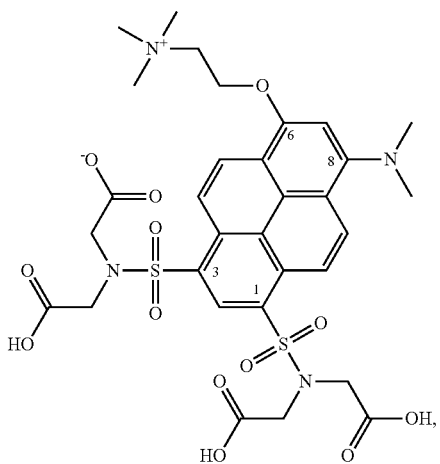

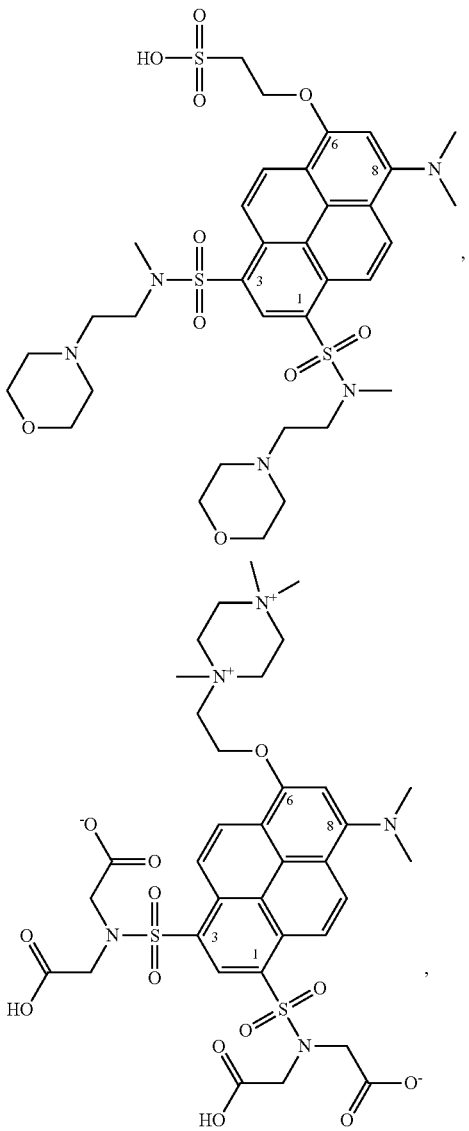

41
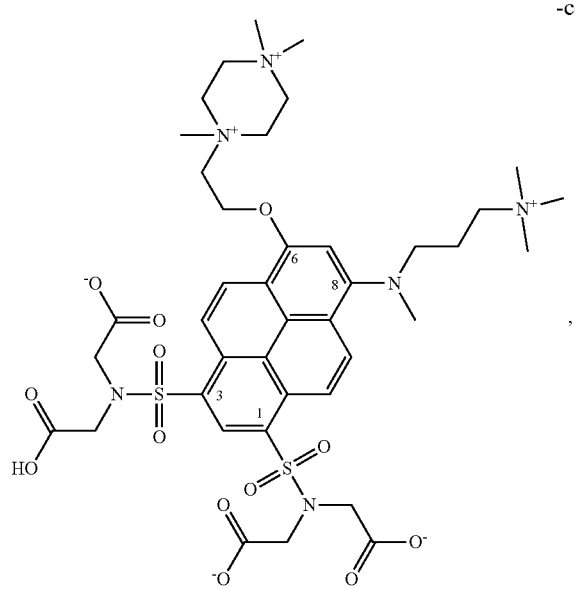
42
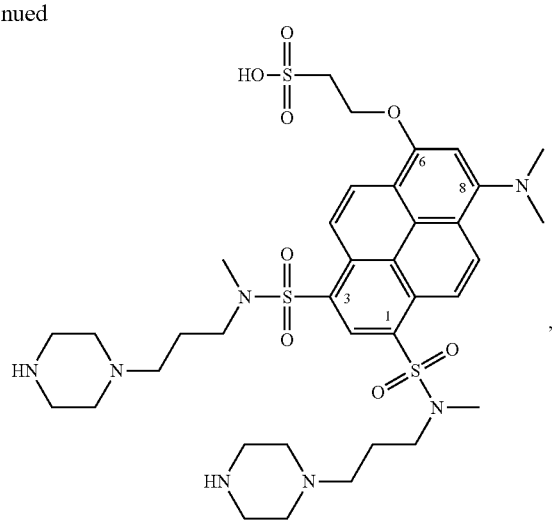
-continued
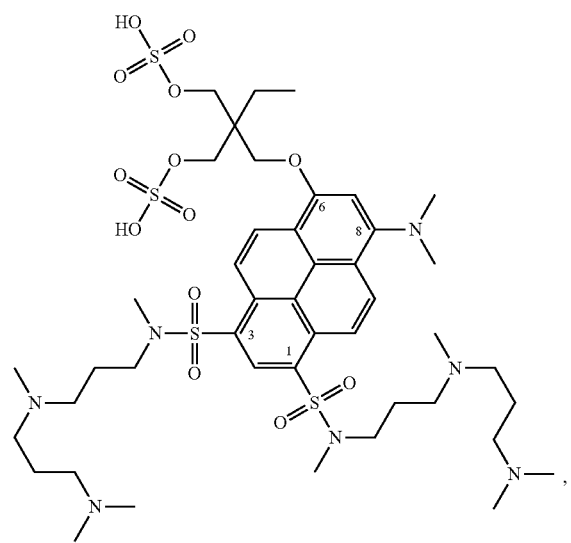
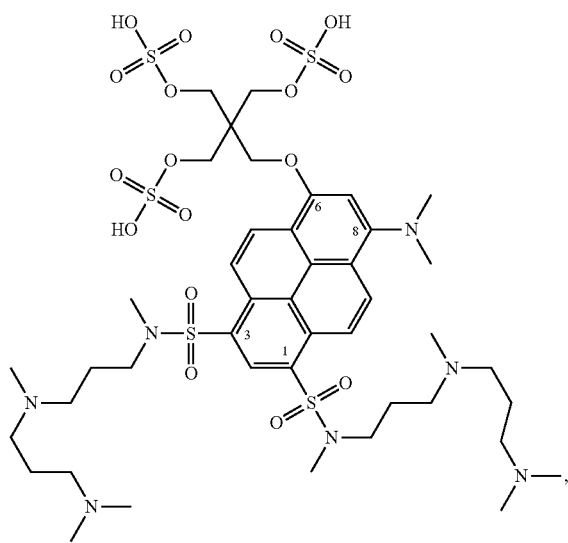
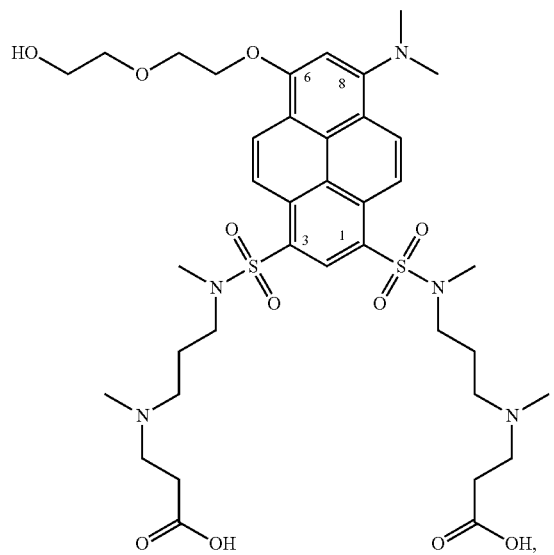

43 44
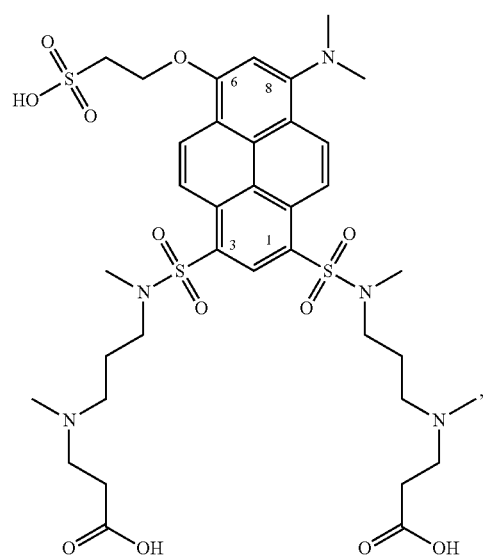
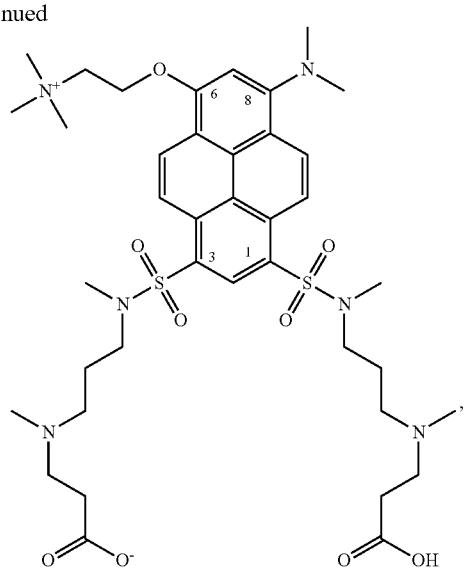
-continued
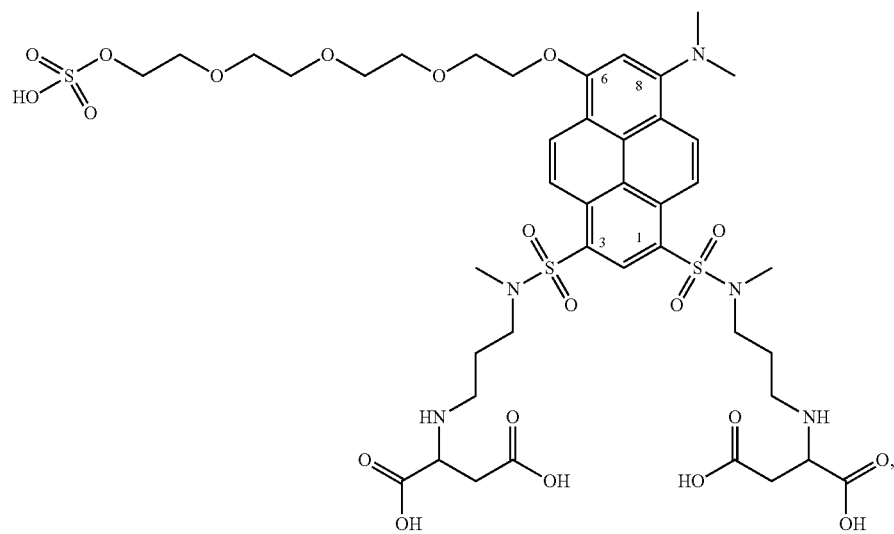
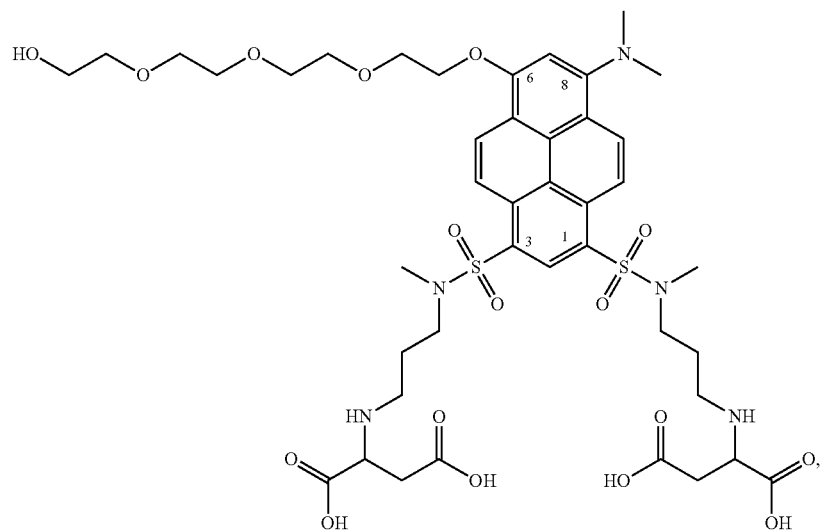

45
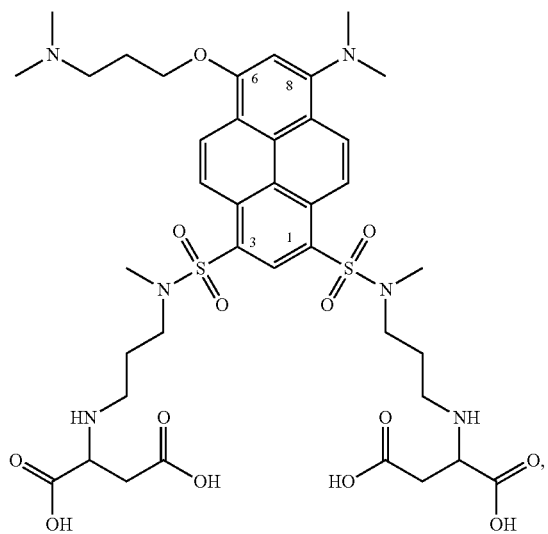
46
-continued
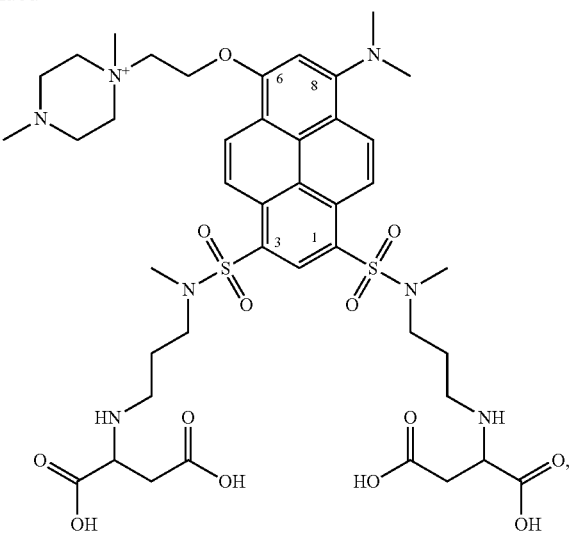
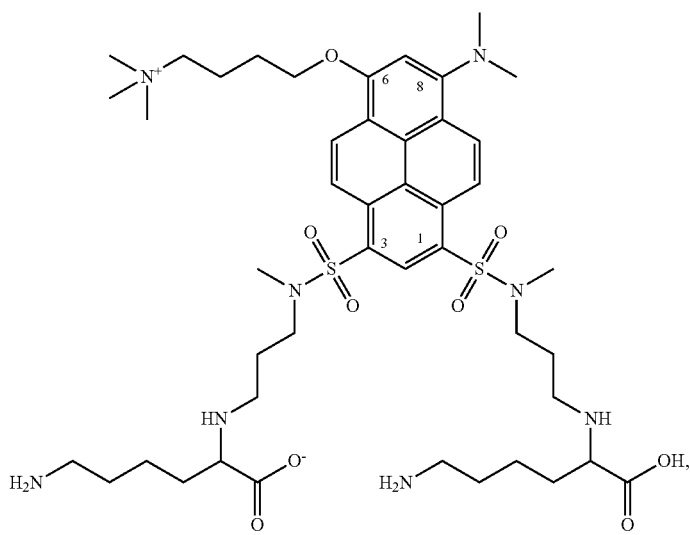
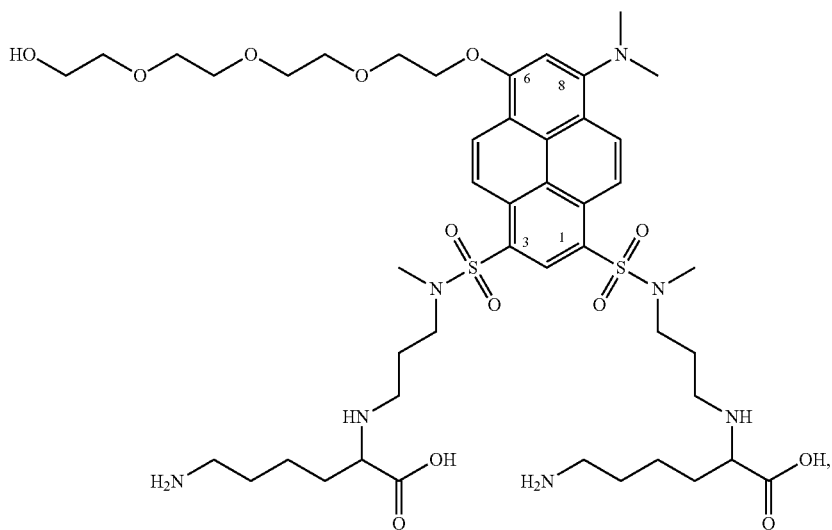

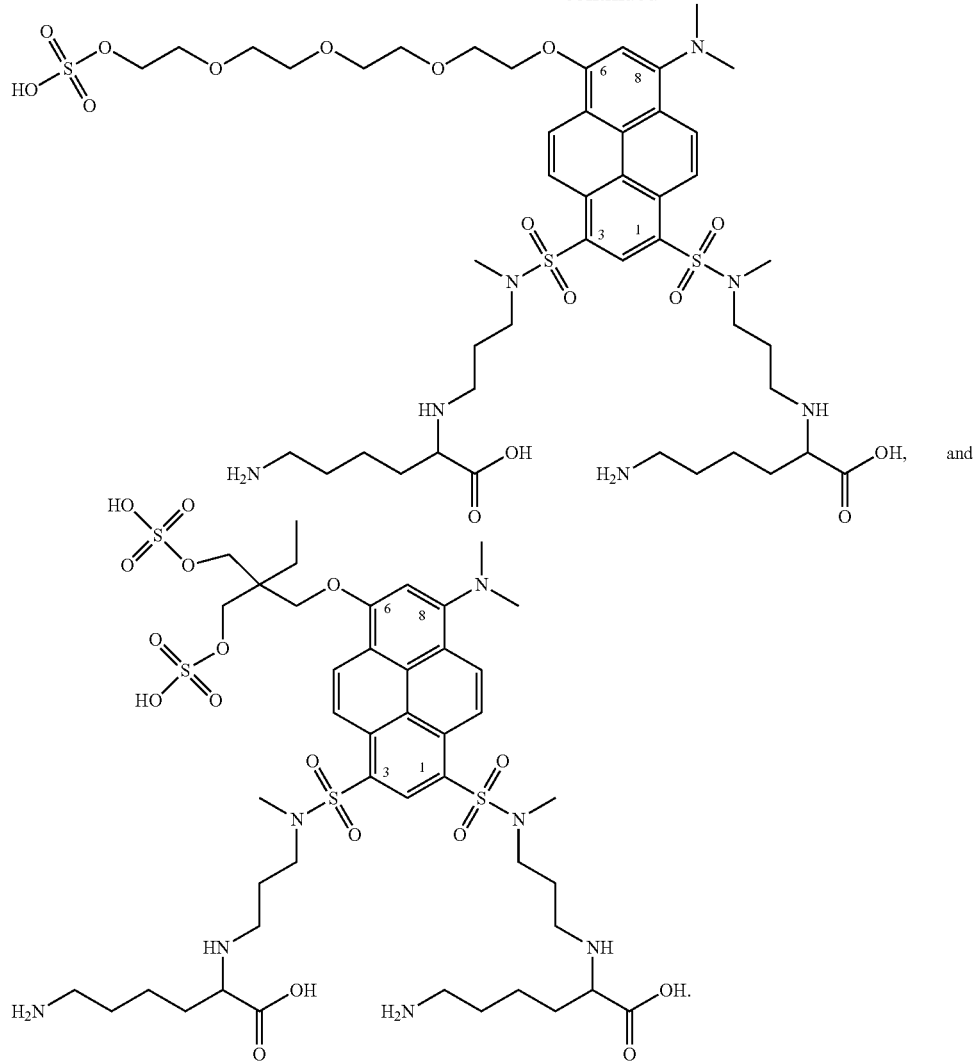
4. The compound of claim 1 selected from the group consisting of:
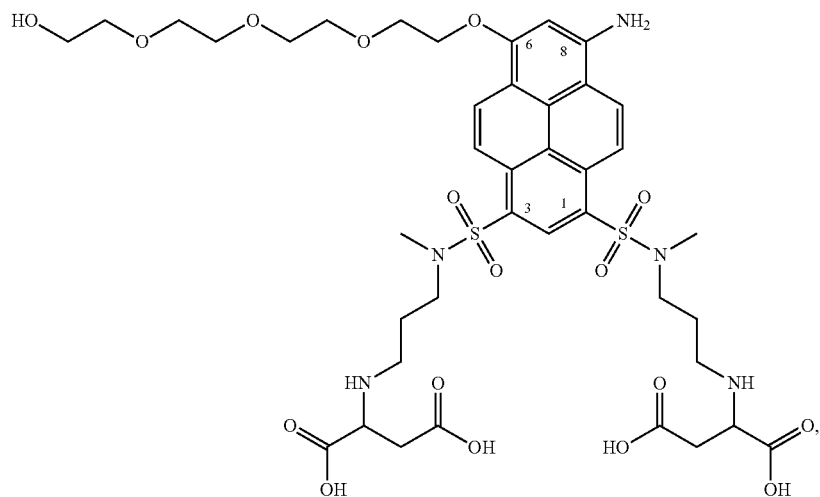

-continued
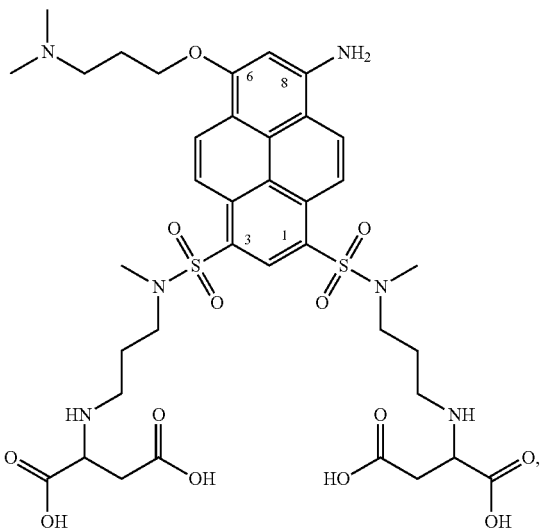
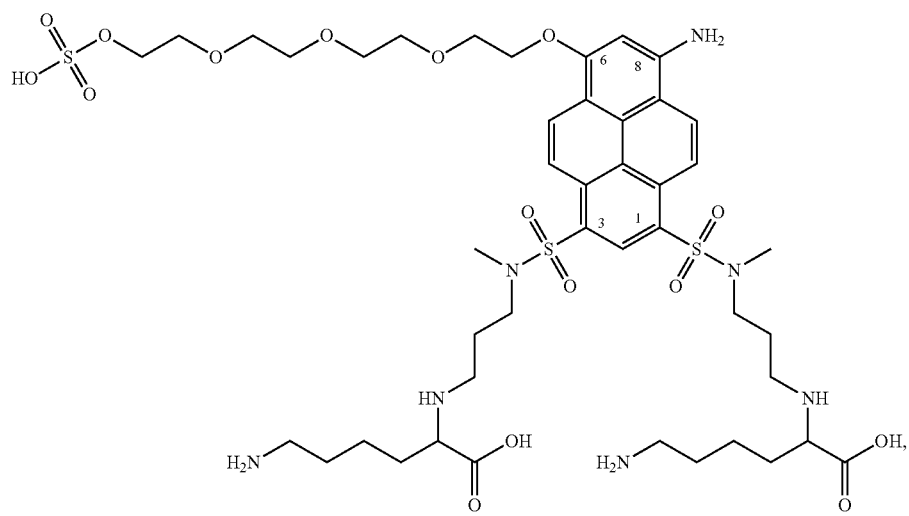
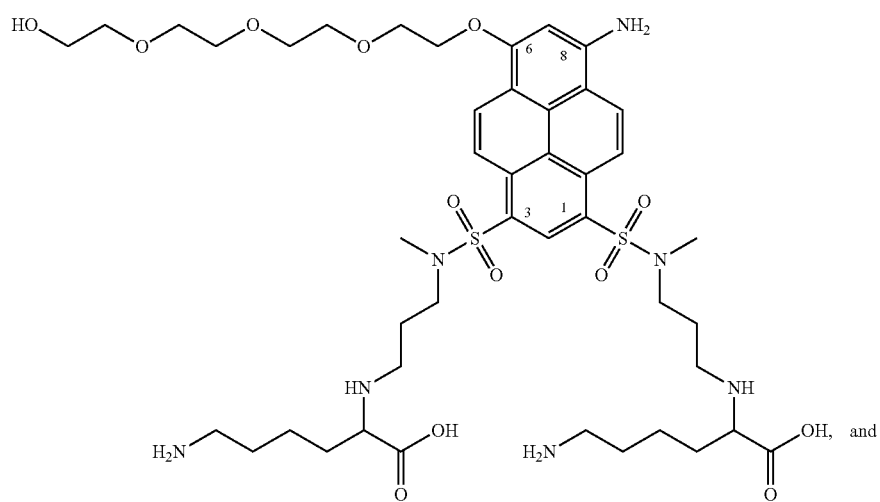

-continued
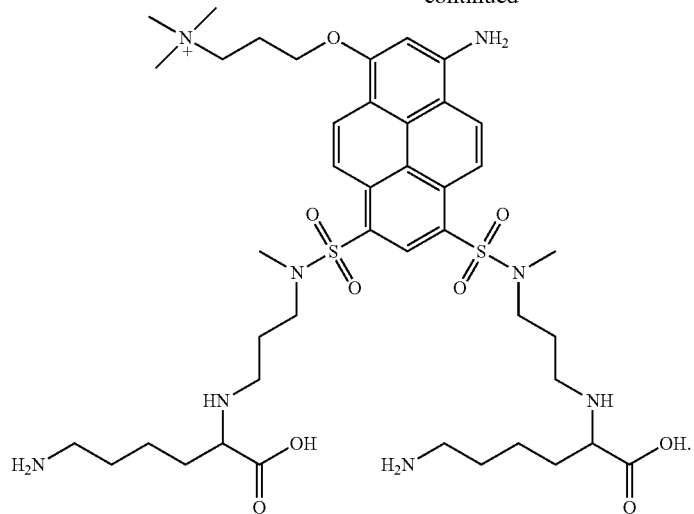

The invention claimed is:
1. A compound having the formula:

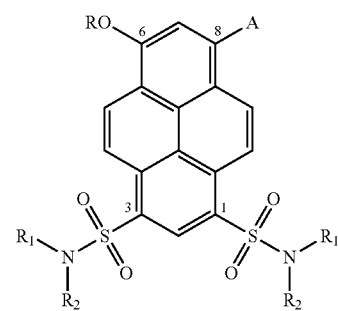

wherein
A is selected from the group consisting of $OR_3$, $SR_3$, and $N(R_4)(R_5)$,
wherein R₃ is selected from the group consisting of
—(CH₂)ₙ— where n is from 1 to 12,
—(CH₂CH—)ₙ— where n is from 1 to 12,
—(CH₂CH₂O)ₙ— where n is from 1 to 20, and
—(CH₂CH(OH)CH₂O)ₙ— where n is from 1 to 20,
wherein each terminates with hydrogen, a non-charged group, or at least one moiety selected from the group consisting of amino, secondary amino, tertiary amino, azaaryl, hydroxyaryl, and carboxylic acid group;
wherein R₄ and R₅ are independently selected from the group consisting of
hydrogen,
—(CH₂)ₙ— where n is from 1 to 12,
—(CH₂CH—)ₙ— where n is from 1 to 12, —(CH$_2$CH$_2$O)$_n$— where n is from 1 to 20, and
—(CH$_2$CH(OH)CH$_2$O)$_n$— where n is from 1 to 20,
wherein each of —(CH$_2$)$_n$—, —(CH$_2$CH—)$_n$, —(CH$_2$CH$_2$O)$_n$—, and —(CH$_2$CH(OH)CH$_2$O)$_n$— terminates with hydrogen, a non-charged group, or at least one moiety selected from the group consisting of amino, secondary amino, tertiary amino, azaaryl, hydroxyaryl, and carboxylic acid group;

R is selected from the group consisting of
—(CH$_2$)$_n$— where n is from 1 to 12,
—(CH$_2$CH—)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each terminates with hydrogen, a non-charged group, or at least one moiety selected from the group consisting of amino, secondary amino, tertiary amino, azaaryl, hydroxyaryl, carboxylic acid or carboxylate, sulfonic acid or sulfonate, and or hydrogen sulfate or sulfate group; and R$_1$ and R$_2$ at each occurrence are independently selected from the group consisting of
hydrogen,
—(CH$_2$)$_n$— where n is from 1 to 12,
—(CH$_2$CH—)$_n$— where n is from 1 to 12,
—(CH$_2$CH$_2$O)$_n$— where n is from 1 to 20, and
—(CH$_2$CH(OH)CH$_2$O)$_n$— where n is from 1 to 20,
wherein each terminates with hydrogen, a non-charged group, or at least moiety selected from the group consisting of amino, secondary amino, tertiary amino, azaaryl, hydroxyaryl, and carboxylic acid group.

2. A method for establishing the shape of a pH gradient between an anode and a cathode across an electrophoretic device in an isoelectric focusing or isoelectric trapping experiment, comprising
(a) introducing one or more pI markers having a known pI value into an electrophoretic device, wherein the one or more pI markers comprises a compound of claim 1; and
(b) applying an electric field sufficient for a period of time sufficient to separate and concentrate the one or more pI markers.

3. The compound of claim 1 selected from the group consisting of: